(12) United States Patent
Jones et al.

(10) Patent No.: US 9,610,099 B2
(45) Date of Patent: Apr. 4, 2017

(54) TISSUE FIXATION DEVICE TO GRASP, RETAIN AND RELEASE TISSUE

(71) Applicants: IMDS LLC, Providence, UT (US); Mikenclaud LLC, Chubbuck, ID (US)

(72) Inventors: Michael Jones, Chubbuck, ID (US); Nathan O. Plowman, Wellsville, UT (US); Nathan Erickson, Beaver Dam, UT (US); Andrew R. Fauth, River Heights, UT (US); Daniel J. Triplett, Providence, UT (US)

(73) Assignees: IMDS LLC, Providence, UT (US); MIKENCLAUD LLC, Chubbuck, ID (US)

( * ) Notice: Subject to any disclaimer, the term of this patent is extended or adjusted under 35 U.S.C. 154(b) by 313 days.

(21) Appl. No.: 14/396,743

(22) PCT Filed: Apr. 26, 2013

(86) PCT No.: PCT/US2013/038512
§ 371 (c)(1),
(2) Date: Oct. 23, 2014

(87) PCT Pub. No.: WO2013/163609
PCT Pub. Date: Oct. 31, 2013

(65) Prior Publication Data
US 2015/0105807 A1  Apr. 16, 2015

Related U.S. Application Data

(63) Continuation of application No. 13/472,297, filed on May 15, 2012, now Pat. No. 9,089,365.
(Continued)

(51) Int. Cl.
*A61B 17/03* (2006.01)
*A61B 17/42* (2006.01)
(Continued)

(52) U.S. Cl.
CPC .......... *A61B 17/4241* (2013.01); *A61B 17/08* (2013.01); *A61B 17/122* (2013.01);
(Continued)

(58) Field of Classification Search
CPC ....... A61B 17/08; A61B 17/122; A61B 17/42; A61B 17/4241; A61B 17/44; A61B 17/442; A61B 2017/4216; A61B 2017/4225
(Continued)

(56) References Cited

U.S. PATENT DOCUMENTS

| 75,158 A | 3/1868 | Hamilton |
|---|---|---|
| 496,711 A | 5/1893 | Thompson |

(Continued)

FOREIGN PATENT DOCUMENTS

| GB | 2305609 | 4/1997 |
|---|---|---|
| WO | WO9729889 | 8/1997 |
| WO | WO2008136024 | 11/2008 |

*Primary Examiner* — Todd J Scherbel
(74) *Attorney, Agent, or Firm* — Maywood IP Law; G. Jo Hays; David W. Meibos

(57) ABSTRACT

Tissue fixation members 18 interact with a housing 12 to hold tissue relative to the housing and allow the orientation and position of the grasped tissue to be manipulated with improved efficacy. The tissue fixation members can be easily and quickly moved between deployed and retracted positions to reversibly grasp and release tissue.

20 Claims, 55 Drawing Sheets

Related U.S. Application Data

(60) Provisional application No. 61/782,266, filed on Mar. 14, 2013, provisional application No. 61/638,979, filed on Apr. 26, 2012.

(51) Int. Cl.
*A61B 17/08* (2006.01)
*A61B 17/122* (2006.01)
*A61B 17/44* (2006.01)
*A61B 17/34* (2006.01)
*A61B 17/00* (2006.01)

(52) U.S. Cl.
CPC .............. *A61B 17/42* (2013.01); *A61B 17/44* (2013.01); *A61B 17/442* (2013.01); *A61B 2017/00349* (2013.01); *A61B 2017/3488* (2013.01); *A61B 2017/4216* (2013.01); *A61B 2017/4225* (2013.01)

(58) Field of Classification Search
USPC .......................................... 606/209; 600/217
See application file for complete search history.

(56) References Cited

U.S. PATENT DOCUMENTS

| | | |
|---|---|---|
| 1,400,616 A | 12/1912 | McCrory |
| 1,462,202 A | 7/1923 | Hopper |
| 1,991,278 A | 2/1935 | Heintz |
| 2,082,782 A | 6/1937 | Allen |
| 2,108,206 A | 2/1938 | Meeker |
| 2,146,472 A | 2/1939 | Heintz |
| 2,482,622 A | 9/1949 | Kahn |
| 2,536,145 A | 1/1951 | Tapke |
| 2,616,421 A | 11/1952 | Greenberg |
| 3,877,433 A | 4/1975 | Librach |
| 4,022,208 A | 5/1977 | Valtchev |
| 4,085,756 A | 4/1978 | Weaver |
| 4,997,419 A | 3/1991 | Lakatos |
| 5,059,198 A | 10/1991 | Gimpelson |
| 5,100,382 A | 3/1992 | Valtchev |
| 5,209,754 A | 5/1993 | Ahluwalia |
| 5,259,836 A | 11/1993 | Thurmond |
| 5,336,228 A | 8/1994 | Cholhan |
| 5,368,598 A | 11/1994 | Hasson |
| 5,382,252 A | 1/1995 | Failla |
| 5,409,496 A | 4/1995 | Rowden |
| 5,445,643 A | 8/1995 | Valtchev |
| 5,464,409 A | 11/1995 | Mohajer |
| 5,520,698 A | 5/1996 | Koh |
| 5,540,700 A | 7/1996 | Rowden |
| 5,562,679 A | 10/1996 | Valtchev |
| 5,562,680 A | 10/1996 | Hasson |
| 5,578,048 A | 11/1996 | Pasqualucci |
| 5,643,285 A | 7/1997 | Rowden |
| 5,662,676 A | 9/1997 | Koninckx |
| 5,697,937 A | 12/1997 | Toma |
| 5,746,750 A | 5/1998 | Prestel |
| 5,833,611 A | 11/1998 | Tepper |
| 5,935,098 A | 8/1999 | Blaisdell |
| 5,980,534 A | 11/1999 | Gimpelson |
| 5,993,461 A | 11/1999 | Abae |
| 6,027,518 A | 2/2000 | Gaber |
| 6,371,973 B1 | 4/2002 | Tepper |
| 6,423,075 B1 | 7/2002 | Singh |
| 6,666,873 B1 | 12/2003 | Cassell |
| 7,175,634 B2 | 2/2007 | Van Heerden |
| 7,294,139 B1 | 11/2007 | Gengler |
| 7,325,546 B2 | 2/2008 | Burbank |
| 7,329,265 B2 | 2/2008 | Burbank |
| 7,479,145 B2 | 1/2009 | Burbank |
| D624,647 S | 9/2010 | Dionisi |
| 8,082,925 B2 | 12/2011 | McCartney |
| D653,338 S | 1/2012 | Mangeshikar |
| 8,162,954 B2 | 4/2012 | George |
| 8,550,088 B1 | 10/2013 | Booher, Sr. |
| 9,089,365 B2 * | 7/2015 | Jones ................. A61B 17/4241 |
| 2001/0021854 A1 | 9/2001 | Donnez |
| 2003/0187334 A1 | 10/2003 | Biswas |
| 2004/0236349 A1 | 11/2004 | Gellman |
| 2005/0080437 A1 | 4/2005 | Wright |
| 2005/0113854 A1 | 5/2005 | Uckele |
| 2005/0125006 A1 | 6/2005 | Nady |
| 2005/0251155 A1 | 11/2005 | Orban |
| 2005/0277948 A1 | 12/2005 | Cedars |
| 2005/0283188 A1 | 12/2005 | Loshakave |
| 2007/0142844 A1 | 6/2007 | Kotmel |
| 2007/0142860 A1 | 6/2007 | Kotmel |
| 2007/0173863 A1 | 7/2007 | Burbank |
| 2007/0260265 A1 | 11/2007 | Walter |
| 2007/0288051 A1 | 12/2007 | Beyer |
| 2008/0058833 A1 | 3/2008 | Rizvi |
| 2008/0109010 A1 | 5/2008 | Feuer |
| 2008/0154244 A1 | 6/2008 | Singh |
| 2008/0188863 A1 | 8/2008 | Chu |
| 2009/0105728 A1 | 4/2009 | Noda |
| 2009/0182329 A1 | 7/2009 | Dycus |
| 2009/0318914 A1 | 12/2009 | Utley |
| 2010/0106163 A1 | 4/2010 | Blair |
| 2010/0256623 A1 | 10/2010 | Nicolas |
| 2010/0274260 A1 | 10/2010 | D'Arpiany |
| 2010/0280524 A1 | 11/2010 | Lopez Zepeda |
| 2010/0305578 A1 | 12/2010 | Auerbach |
| 2011/0106116 A1 | 5/2011 | Ducharme |
| 2012/0029547 A1 | 2/2012 | Shelton |
| 2012/0109014 A1 | 5/2012 | Sherts |
| 2012/0109147 A1 | 5/2012 | Auerbach |
| 2013/0150877 A1 | 6/2013 | Ikeda |

* cited by examiner

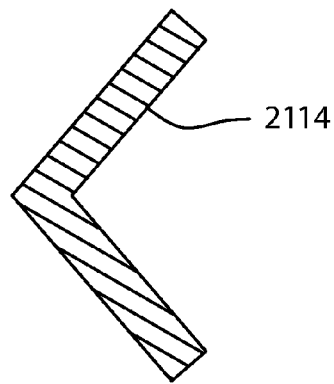
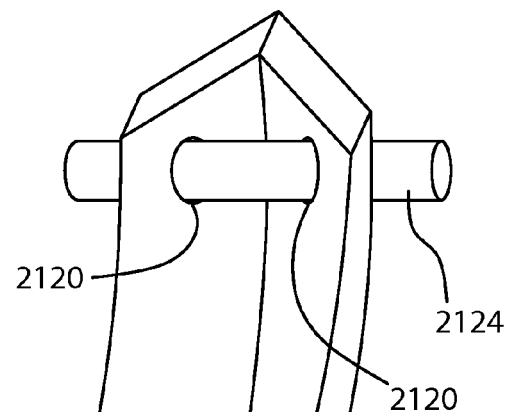
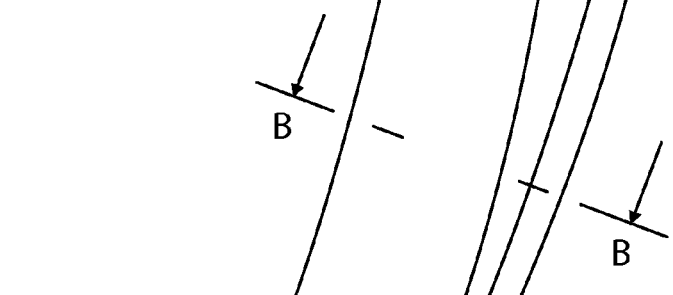
Fig. 49B
Fig. 49A

TISSUE FIXATION DEVICE TO GRASP, RETAIN AND RELEASE TISSUE

BACKGROUND

The present disclosure includes examples of tissue fixation devices. Specifically, the tissue fixation devices described herein may be used with a uterine manipulator to grasp, retain and release cervical tissue. It will be appreciated that the disclosed embodiments may have applications outside of uterine manipulation, and may be used on other bodily tissues.

In some surgical procedures, it is desirable to control the position and orientation of an organ, such as a uterus, to help the surgeon operate on the uterus or on other parts of the body adjacent to the uterus. Uterine manipulator devices can be used to position and orient a uterus during surgery. U.S. Patent Application Publication No. US2012/0109147 discloses an example uterine manipulator system. Typical uterine manipulator systems consist of a bell-housing or cup shaped member that fits around the cervix and a rod member that is inserted through the cervix and into the uterus. The bell housing can be sized and shaped to compress the cervical tissue against the rod member to help the surgeon grasp the cervix and manipulate the position and orientation of the uterus. The bell housing can also provide a cutting guide to facilitate incision placement, for example colpotomy incisions and incisions requiring a safe distance from the ureters and uterine arteries. However, if the cervical tissue fixation within the bell housing is insufficient, a uniform colpotomy incision is difficult to achieve. Furthermore, the risk of damaging surrounding tissues, such as the ureters and uterine arteries, will increase if the tissue fixation is insufficient. The compressive forces imparted to the cervical tissue between the bell housing and the rod member are usually not sufficient enough to tightly grasp the cervix and ensure safe incision placement. Accordingly, it has been known to include a balloon in combination with the rod member which can be inflated inside of the uterus to provide additional pressure on the cervical tissue between the balloon and the bell housing to force the cervical tissue down into the bell housing and increase the gripping force of the bell housing on the cervix. However, the internal balloon may not create optimal tissue fixation, especially in patients with anatomical abnormalities, rigid tissues, scar tissue, and the like. Additionally, the balloon may leak or become accidentally "nicked" by other surgical instruments during the surgical procedure. This may result in loss of tissue fixation that can delay and complicate surgical incisions and/or removal of the uterus through the vagina in the case of a hysterectomy procedure. Moreover, it may not be desirable to use a balloon inside of a uterus containing cancerous cells, because the cancerous cells can be broken loose by the balloon and spread to other parts of the body. Sufficient tissue fixation is typically not achieved with a balloon, as is evidenced by workarounds currently used by many surgeons. For example, surgeons are known to use adjunctive stitches through the cervix which are then tied to the instrument to increase tissue fixation. This workaround adds additional steps to the surgery and further complicates things by making it difficult to quickly remove the bell housing and/or uterine manipulator from the patient if an emergency situation arises, such as the need to defibrillate the patient's heart.

Accordingly, it is desirable to provide a device that achieves reliable tissue fixation, with or without a balloon, that will last throughout the entire surgical procedure and that will not be compromised by rigid tissue, anatomical abnormalities, scar tissue, cancerous tissue, or the like. In some cases, it may also be desirable to generate tissue fixation close to certain incision sites, such as the colpotomy incision site, to increase the control, placement and precision of the incision. It is also desirable to provide a device that employs a simple actuation mechanism to quickly and easily engage and disengage the tissue fixation mechanism during surgery.

An example of the present technology disclosed herein includes a tissue fixation assembly shaped to be attached to a uterine manipulator. The assembly includes a housing, a fixation member carriage with deployable fixation members, and a cap. The fixation member carriage and fixation members are captured between the housing and the cap. In one example, a suture is attached to the fixation member carriage and is actuatable to move the fixation member carriage to deploy or retract the fixation members. The assembly may be inserted into a vagina and receive cervical tissue within the housing. The fixation members may then be deployed inwardly from the housing to grip the cervical tissue. The fixation members may also be locked in the deployed position to maintain the grip on the tissue. The fixation members may also be easily retracted to release the tissue and remove the device as needed.

Those of skill in the art will recognize that the following description is merely illustrative of the principles of the disclosure, which may be applied in various ways to provide many different alternative embodiments and may be applicable outside the fields of surgery or medical devices. While the present disclosure is made in the context of tissue fixation related to the cervix, for the purposes of illustrating the concepts of the design, it is contemplated that the present design and/or variations thereof may be suited to other uses for grasping any bodily tissue. Moreover, the devices and methods set forth herein may be used in open, percutaneous, and/or minimally invasive procedures.

All changes which come within the meaning and range of equivalency of the claims are to be embraced within their scope.

Standard medical planes of reference and descriptive terminology are employed in this specification. A sagittal plane divides a body into right and left portions. A mid-sagittal plane divides the body into equal right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

BRIEF DESCRIPTION OF THE DRAWINGS

Various embodiments of the present disclosure will now be discussed with reference to the appended drawings. It will be appreciated that these drawings depict only typical examples of the present disclosure and are therefore not to be considered limiting of its scope.

FIG. 49A is a side view of a needle; FIG. 49B is a transverse cross section of the needle of FIG. 49A taken along line B-B;

DETAILED DESCRIPTION

Figure 1:
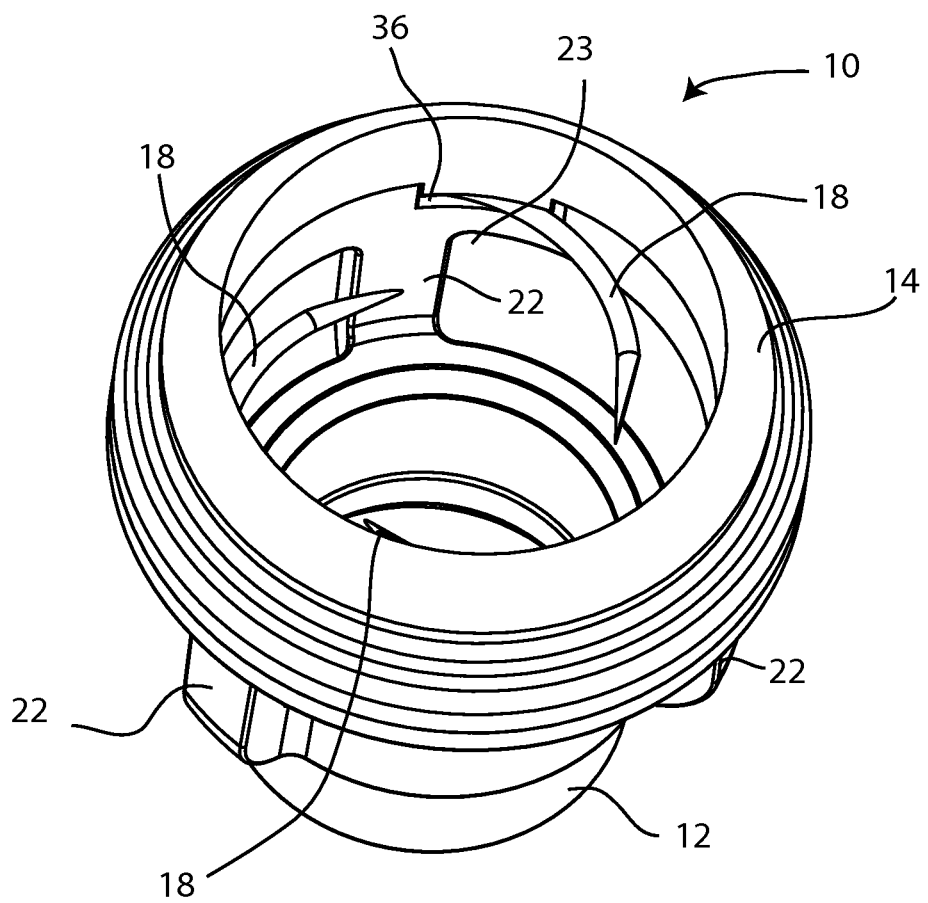
FIG. 1 is a perspective view of a tissue fixation device according to one example of the present disclosure having a housing, a cap, and deployable fixation members.

While certain embodiments are shown and described in detail below by way of illustration only, it will be clear to the person skilled in the art upon reading and understanding this disclosure that changes, modifications, and variations may be made and remain within the scope of the technology described herein. Furthermore, while various features are grouped together in the embodiments for the purpose of streamlining the disclosure, it is appreciated that features from different embodiments may be combined to form additional embodiments which are all contemplated within the scope of the disclosed technology.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to: titanium, titanium alloys, commercially pure titanium grade 2, ASTM F67, Nitinol, cobalt chrome, stainless steel, UHMWPE, PEEK, and biodegradable materials, among others. Different materials may be used within a single part. The devices disclosed herein may also encompass a variety of surface treatments or additives, including but not limited to: anti-microbial additives, analgesics, anti-inflammatories, etc. Any device disclosed herein may include a radiographic marker for imaging purposes. Any device disclosed herein may be color-coded or otherwise marked to make it easier for the surgeon to identify the type and size of the device.

In a first aspect of the disclosure, a tissue fixation device includes a housing having an inner space configured to receive tissue therein and an enclosed section, wherein the enclosed section completely encloses at least one planar surface; and at least one fixation member movable between a retracted configuration and a deployed configuration, wherein when the at least one fixation member is in the deployed configuration, the at least one fixation member protrudes into the inner space, and wherein when the at least one fixation member is in the retracted configuration, the at least one fixation member is retracted relative to the inner space. Various embodiments of the tissue fixation device can include one or more of the following attributes:

In an embodiment, the tissue fixation device can further include a fixation member carriage engaged with the at least one fixation member and configured to move the at least one fixation member between the deployed configuration and the retracted configuration.

In an embodiment, the housing and the fixation member carriage are substantially circular, and rotational movement of the fixation member carriage along a circle defined by the housing moves the at least one fixation member between the retracted and deployed configurations.

In an embodiment, the at least one fixation member is curved, and the diameter of the curvature of the at least one fixation member is less than the diameter of the circle.

In an embodiment, the tissue fixation device can further include a cap detachable from the housing, wherein the fixation member carriage is captured between the cap and the housing.

In an embodiment, the tissue fixation device can further include a plurality of tabs and a plurality of slots, wherein the tabs are received in the slots to attach the cap to the housing.

In an embodiment, the tissue fixation device can further include a first line and a second line, the first and second lines connected to the fixation member carriage, wherein pulling the first line moves the fixation member carriage in a first direction to deploy the at least one fixation member, and wherein pulling the second line moves the fixation member carriage in a second direction to retract the at least one fixation member.

In an embodiment, the at least one fixation member is deployed inwardly toward a lengthwise central axis of the housing in a plane substantially perpendicular to the lengthwise central axis.

In an embodiment, the at least one fixation member has a sharp point capable of piercing tissue.

In an embodiment, the at least one fixation member is curved with an arch shape that substantially lies in a single plane.

In an embodiment, the at least one fixation member is connected to the fixation member carriage by a hinge type connection, about which the fixation member pivots.

In an embodiment, the at least one fixation member is deflected by the cap as it moves to the deployed configuration.

In an embodiment, the tissue fixation device includes three fixation members, each of the three fixation members being substantially coplanar with each other.

In an embodiment, the at least one fixation member is helically shaped.

In an embodiment, the housing is frustoconical in shape.

FIGS. 1-8 illustrate one example of a tissue fixation device 10. The tissue fixation device 10 can include a housing 12, a cap 14, and a fixation member carriage assembly 16 (shown first in FIG. 4) which carries at least one fixation member 18. In some examples, the fixation member 18 may be a needle. The fixation member carriage assembly 16 can be captured between the housing 12 and cap 14, and may be rotatable within a track 26 (FIG. 4) formed in the housing 12 and/or the cap 14. It is appreciated that in other embodiments, the cap 14 may be integral with the housing 12 and not formed as a separate element.

The cap 14 and housing 12 may be referred to as a bell cap or a bell housing, as they may form a bell shape in some examples. In some examples, the housing 12 can have at least one enclosed section that completely encloses at least one planar surface. The at least one planar surface can be defined by a cross-sectional plane through the housing that results in a planar surface that is completely enclosed or surrounded by a portion of the housing. In other words, the planar surface is an empty plane that is completely bounded by the housing 12. For example, with reference to FIG. 2, if a cross section of the housing 12 is taken perpendicular to the longitudinal central axis 35 and through the top portion of the housing, or the cap 14, a circular planar surface would be created which lies within the opening, or inner space 33 of the housing 12 and which is completely bounded by or surrounded by the housing 12 or cap 14. On the other hand, if the perpendicular cross-sectional plane were moved lower on the housing to where it crosses the struts 22, housing inner space 33, and windows 23, then this would result in a planar surface that is not completely bounded on all sides, or surrounded by the housing 12 because the windows 23 are open.

In other examples, the housing 12 may not have at least one enclosed section. In these examples there may be discontinuities or breaks in the housing (not shown) of any size or shape. In these examples, the at least one fixation member can be deployed away from an inner surface 42 of the housing and into the opening, or inner space 33 to grip tissue. The at least one fixation member can be also be retracted away from the opening toward an inner surface of the housing to release the tissue.

Figure 2:
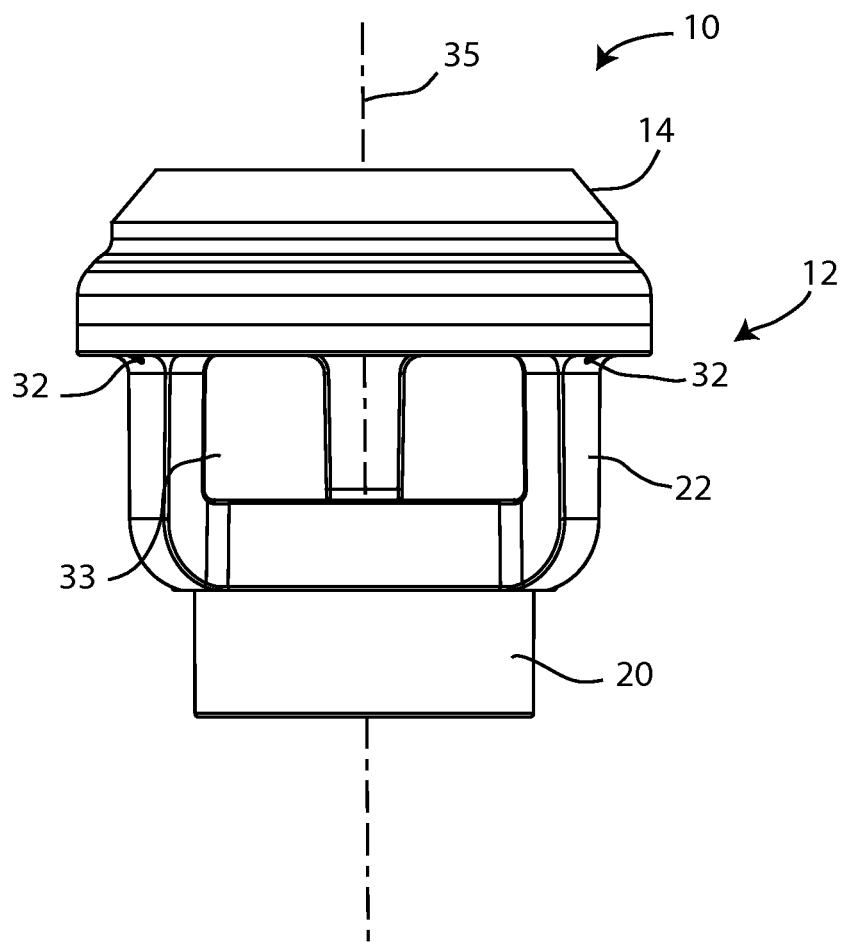
FIG. 2 is a side view of the tissue fixation device of FIG. 1.
Figure 3A:
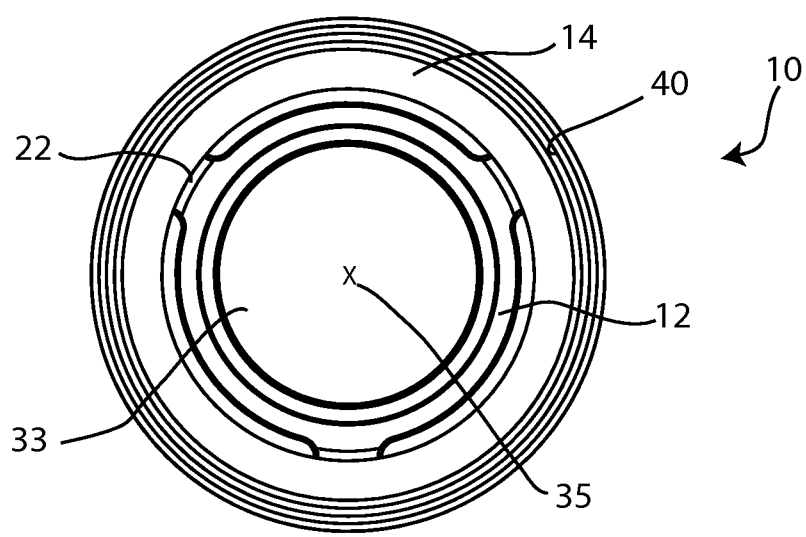
FIG. 3A is a top view of the tissue fixation device of FIG. 1 with the fixation members in a retracted position.
Figure 3B:
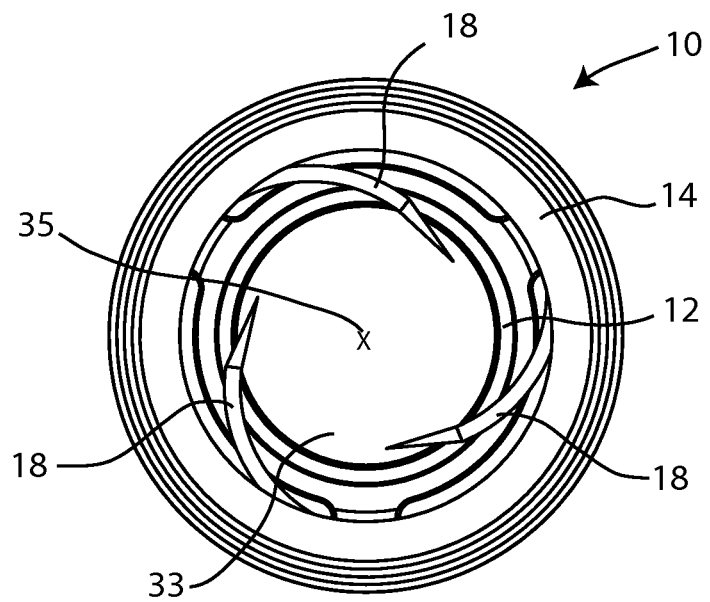
FIG. 3B is a top view of the tissue fixation device of FIG. 1 with the fixation members in a deployed position.

Referring to FIGS. 3A and 3B, the device can be actuable between a fixation member 18 retracted configuration, and a fixation member 18 deployed configuration. From the top or bottom perspective, the device can be radially symmetric. The embodiment shown in FIGS. 1-8 includes three curved fixation members 18. It will be appreciated that other embodiments may include more or fewer fixation members 18.

Figure 4:
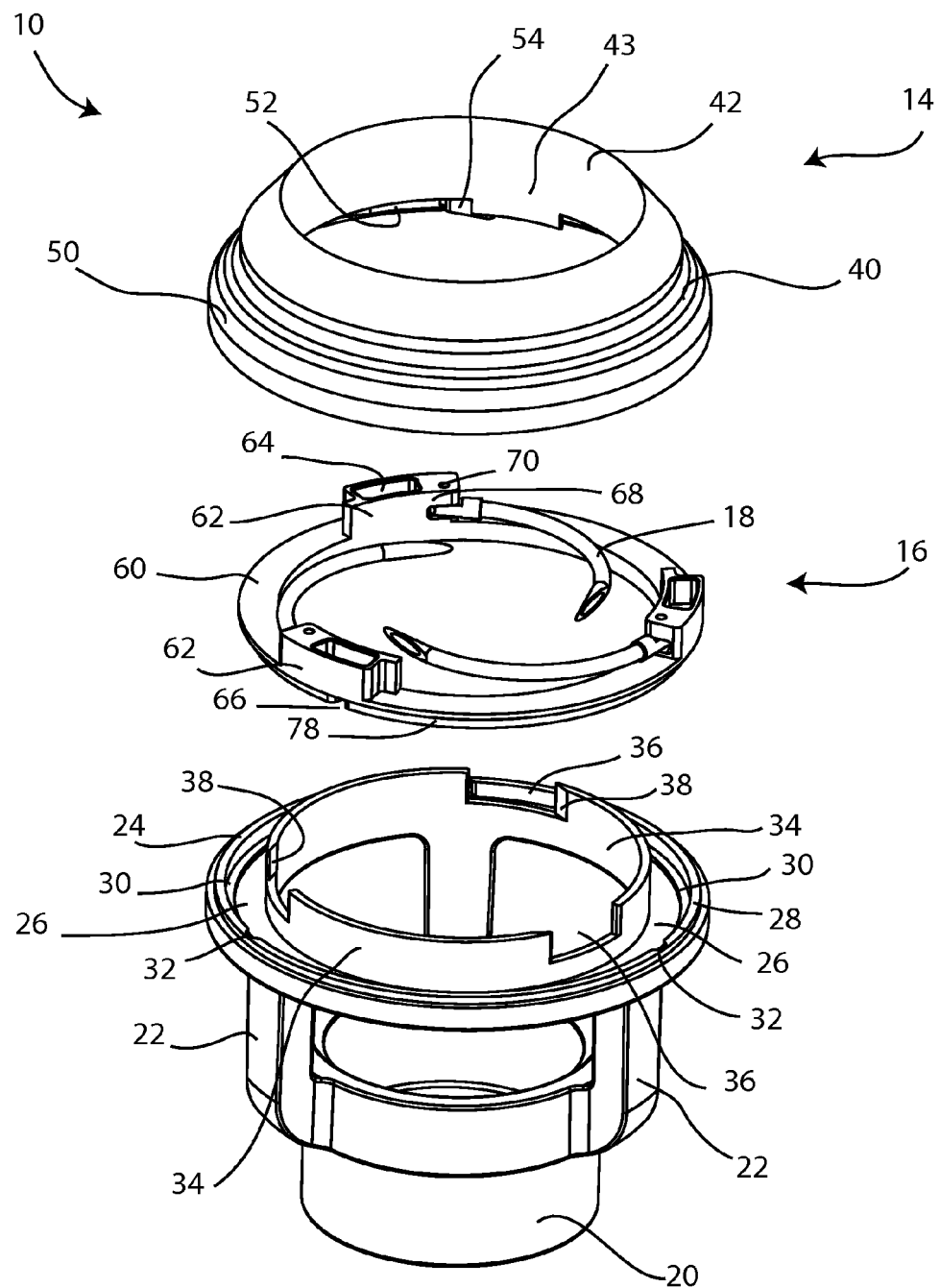
FIG. 4 is an exploded view of the tissue fixation device of FIG. 1.
Figure 5:
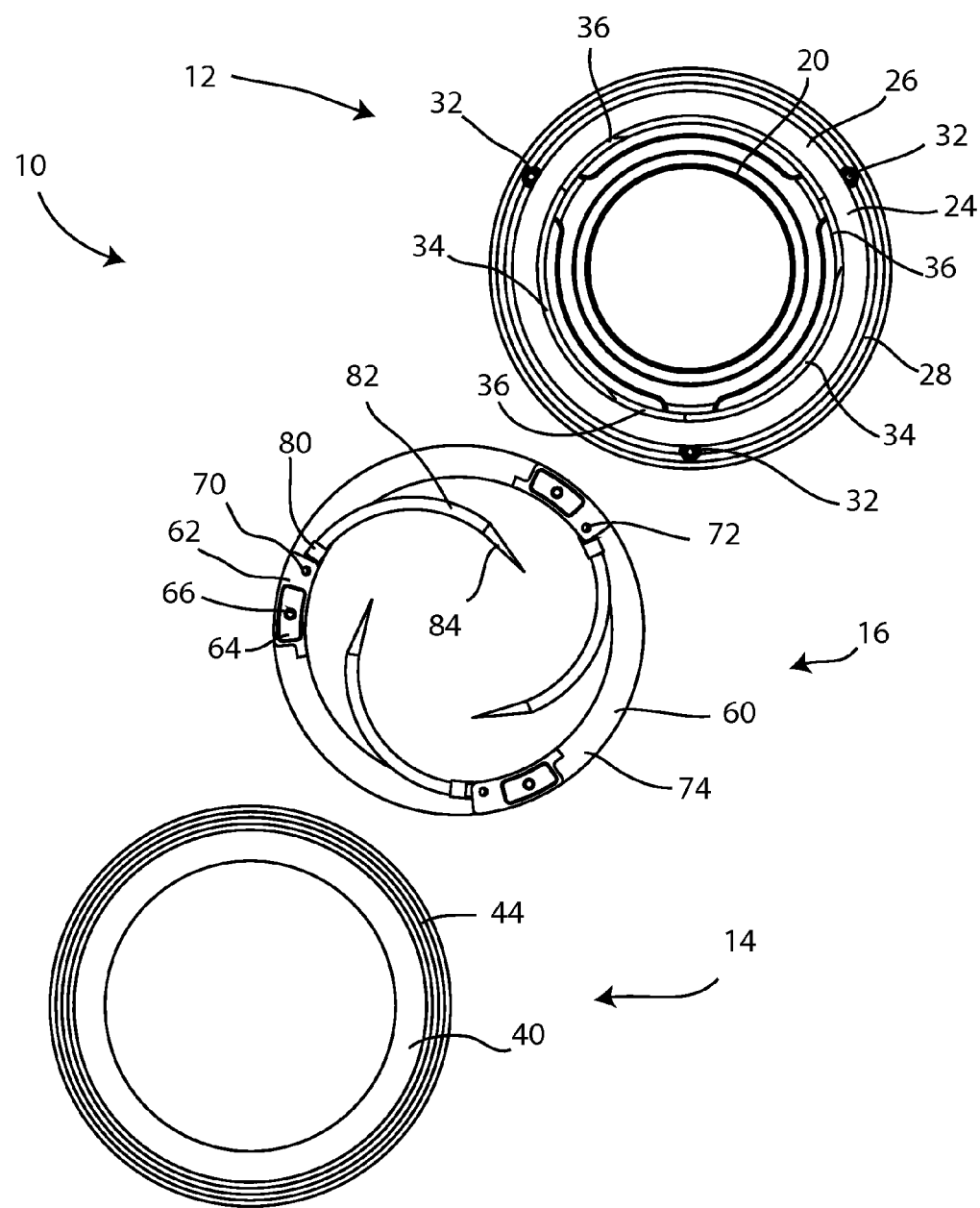
FIG. 5 is a top exploded view of the tissue fixation device of FIG. 1.

Referring to FIGS. 4 and 5, housing 12 can be substantially circular or cylindrical in shape. However, the housing 12 can also be conical, frustoconical, funnel, ovoid, or polygonal in shape, or any combination of shapes thereof. The shape of the housing is not as important as the ability of the housing to enclose tissue to be grabbed by one or more fixation members, as will be apparent from the present disclosure. Continuing with FIGS. 4 and 5, housing 12 may include an attachment portion 20 which may be shaped to connect to a uterine manipulator (not shown). A plurality of struts 22 can project superiorly from the attachment portion 20 and terminate at a carriage support 24. Windows 23 may be interspersed between the struts 22. However, in other embodiments, the housing may not include struts 22 or windows 23. The carriage support 24 can be ring-shaped, and include a carriage track 26, which may be substantially circular. An outer rim 28 can circumscribe the outer diameter of carriage track 26, and a step 30 may be formed intermediate the track 26 and the outer rim 28. One or more apertures 32 can open through the carriage support 24, and may pass through at least a portion of the outer rim 28 and step 30. A housing inner wall 34 can circumscribe the inner diameter of the carriage track 26, and may include a plurality of discontinuations, or wall gaps 36. At least one edge 38 of each wall gap 36 may be beveled. When operatively assembled, the fixation members 18 are deployable through the wall gaps 36; the beveled edges 38 may promote smooth deployment of the fixation members 18 and prevent the fixation members 18 from hanging up or being caught in the wall gaps 36.

Housing 12 may be generally stepped in outer profile, wherein the carriage support 24 has the widest outer diameter, struts 22 form a circle of intermediate diameter, and attachment portion 20 has the narrowest outer diameter (FIG. 2). The inner wall 34, struts 22, and attachment portion 20, may surround and define a housing inner space 33. A lengthwise central axis 35 may extend through the housing inner space 33, also defined by the inner wall 34, struts 22, and attachment portion 20. The number and width of struts 22 and windows 23 may vary, and in some embodiments the housing 12 may be formed as a continuous piece extending between the attachment portion 20 and the carriage support 24, with no struts 22 or windows 23 present. The embodiment depicted in FIGS. 1-8 is generally bell shaped; however in other embodiments the housing 12 and/or the device 10 may have a cylindrical shape and may include a tapered portion at either end. In other embodiments the device 10 may be cup or bowl shaped, or polygonal.

Figure 6:
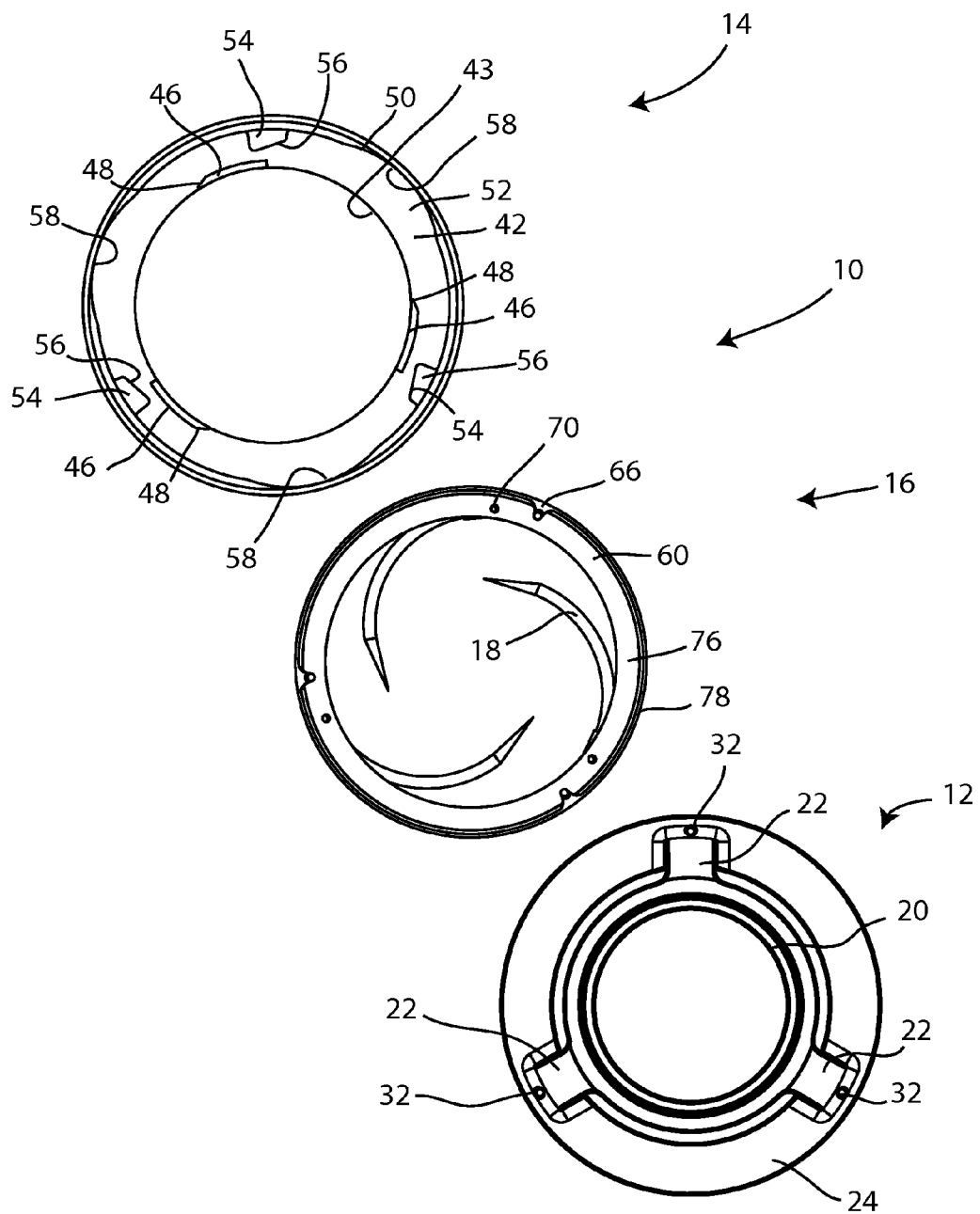
FIG. 6 is a bottom exploded view of the tissue fixation device of FIG. 1.

Cap 14 may have a ring-shape, and may include an outer side 40 opposite an inner side 42. An outer surface 44 (FIG. 5) of the outer side 40 may be positioned as an upper surface, and may include a plurality of steps, ridges and/or grooves which may facilitate gripping and manipulating the cap 14. As seen in FIG. 6, the inner side 42 may have circular outer and inner diameters. A cap inner wall 43 forms the inside diameter of the cap 14, and may include a plurality of tabs 46 which project inferiorly from the inner wall 43. Each tab 46 may include at least one beveled edge 48. A cap outer wall 50 may extend inferiorly, intermediate to and adjoining cap inner wall 43 and cap outer wall 50 and form a track cover 52. A plurality of cap bosses 54 can project inwardly from the cap outer wall 50. Each cap boss 54 may include a ramp feature 56 which urges the fixation member 18 inward as it is deployed. The cap 14 can also have beveled edges 48 which can also help urge the fixation member 18 inward as it is deployed. Cap outer wall 50 can include a plurality of recessed alcoves 58 which allow space for the curved fixation members 18 to be retained within the cap outer wall 50 when the fixation members 18 are in the retracted position. Housing 12 and cap 14 may be formed of plastic, or other materials listed herein.

Fixation carriage assembly 16 can include a generally circular fixation carriage 60. A plurality of mounting features 62 can project superiorly from the fixation carriage 60. Each mounting feature 62 may include a recess 64 through which an opening 66 is formed. Openings 66 can be sized to allow passage of a suture 90. Each mounting feature 62 can further include a fixation member mount 68. In the embodiment shown, fixation member mount 68 includes two pin holes 70 through which a mounting pin 72 passes. Fixation member carriage 60 can have a first or superior side 74 and a second or inferior side 76. A circular setback or groove 78 can be formed on the inferior side 76, and be sized to receive a suture.

Figure 7A:
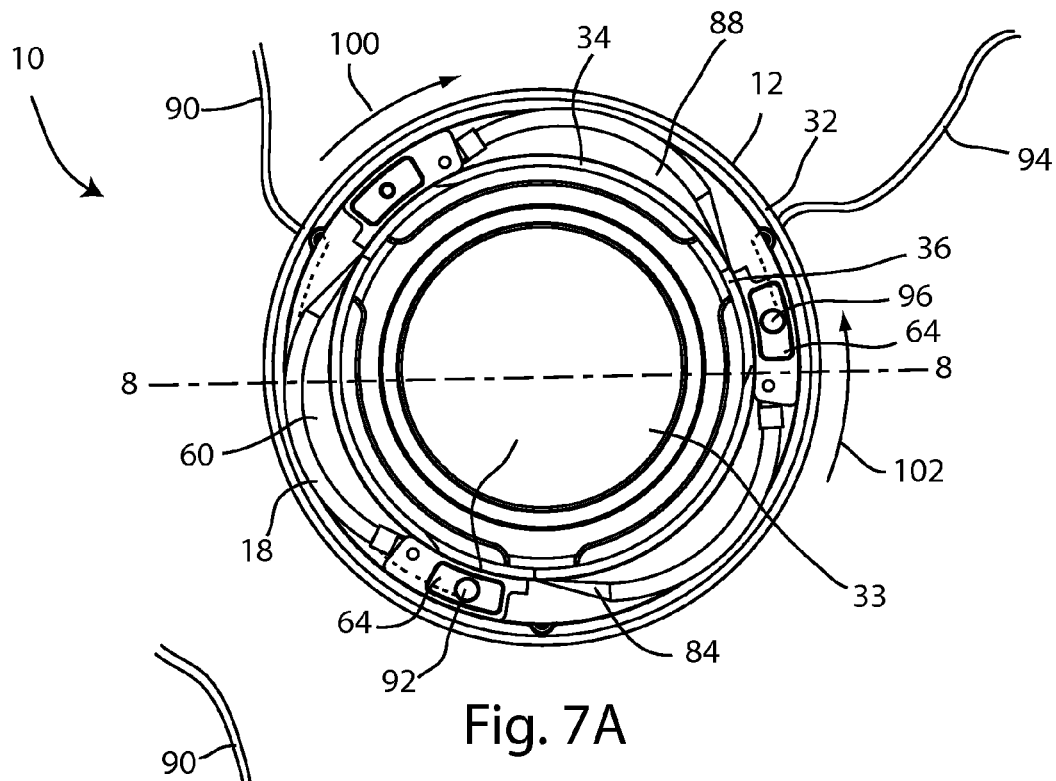
FIG. 7A is a top view of the housing and fixation member carriage assembly of the tissue fixation device of FIG. 1 with the fixation members in a retracted position and dashed lines indicating suture paths under the fixation member carriage assembly.

Each fixation member 18 can be curved, rigid, and may terminate at a beveled point. The rigid fixation members may be formed of stainless steel, or other materials disclosed herein. Other embodiments may include flexible fixation members, which may be straight or curved, and may be made of Nitinol, for example. The fixation member curvature may be non-concentric with the curvature of the carriage track 26, for example the fixation member curvature may have a smaller diameter than the diameter of the carriage track (FIG. 7A). Each fixation member 18 may include a base portion 80, a shaft 82, and a point 84, which may also be referred to as a tip. The point 84 may be sharpened and/or serrated in order to reduce the forces necessary to pierce the tissue, or deploy the fixation member. Any of the fixation members disclosed herein may also include a sharp tip or point for the same purpose. The fixation member 18 may have an arch shape that lies substantially in a single plane in some examples, in other examples, the fixation member can be substantially straight. In yet further examples, the fixation member can have a curved shape in multiple planes or in an infinite number of planes. When assembled into the fixation member carriage assembly 16, base portion 80 is received in fixation member mount 68, and a mounting pin 72 may pass through the fixation member mount 68 and base portion 80 to form a hinge type connection, about which the fixation member 18 may pivot.

Figure 7B:
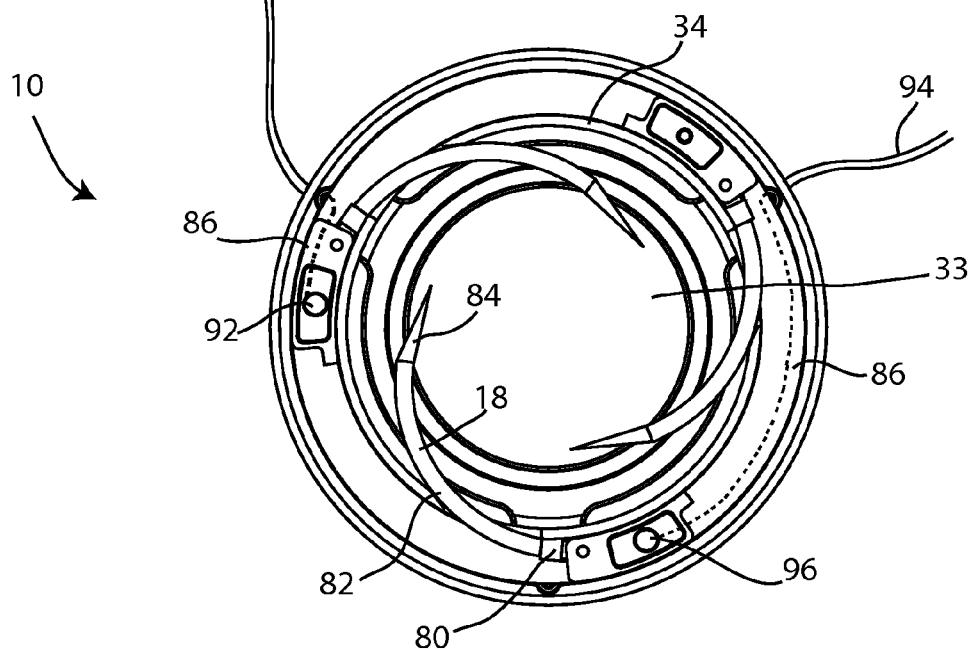
FIG. 7B is a top view of the housing and fixation member carriage assembly of the tissue fixation device of FIG. 1 with the fixation member in a deployed position.
Figure 8:
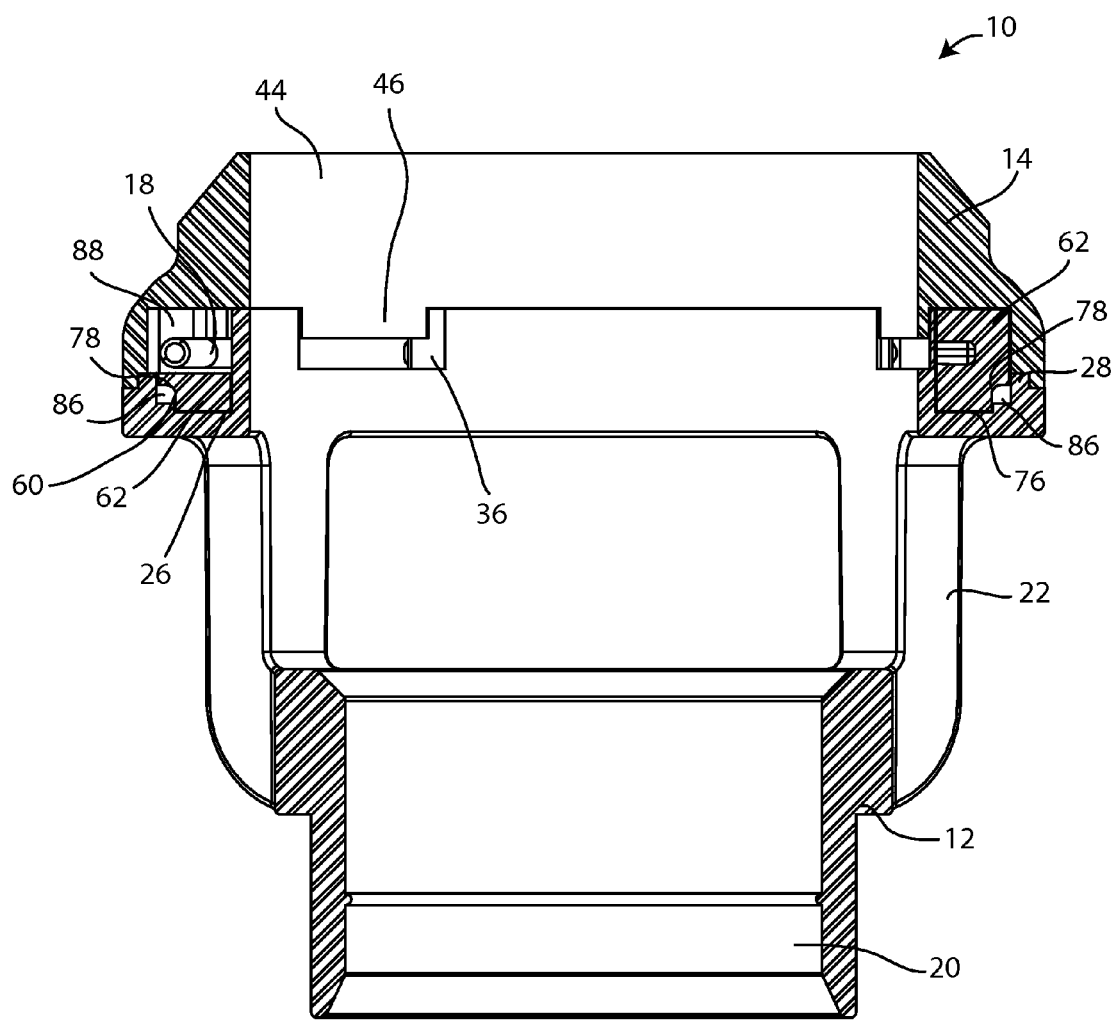
FIG. 8 is a side cross-sectional view of the tissue fixation device of FIG. 1 with the fixation members in a retracted position, taken along section line 8-8 in FIG. 7A.

Referring to FIGS. 7A, 7B, and 8, fixation member carriage assembly 16 may be mounted in the upper portion of housing 12, such that fixation member carriage 60 is received in carriage track 26. A line passage or suture passage 86 may be formed between the groove 78 and outer rim 28. A first line, or suture 90 may be threaded through one opening 66, along suture passage 86 in a first direction 100 and through one aperture 32. A knot 92 may be formed in the suture end remaining at opening 66, the knot residing in recess 64 immediately adjacent opening 66, and the knot preventing withdrawal of the first suture through the opening 66. A second suture 94 may be threaded through a second opening 66, along suture passage 86 in a second direction 102 opposite the first direction, and through another aperture 32. The second suture 94 may also be knotted, forming knot 96 to prevent withdrawal. In another example, the first line 90 and/or second line 94 may be secured in one or more crimp tubes which reside in openings 66, the crimp tube(s) preventing withdrawal of the first and/or second suture through the corresponding opening 66. When the first and second sutures are thus placed, pulling on the first suture 90 will pull the fixation member carriage assembly 16 in the first direction 100, and pulling on the second suture will pull the fixation member carriage assembly 16 in the second, or opposite, direction 102. The sutures 90, 94 may be replaced by another type of line, flexible member, rigid member, filament, braid, yarn, cable, wire, chain, strap, lacing, or the like.

In an alternative threading embodiment, a single suture can be used. A first end of the suture is passed down through one opening 66, along suture passage 86 and out one aperture 32. The first end is then passed partially around the housing 12, up into a second aperture 32, along suture passage 86 and up through a second opening 66. The suture is knotted at both of the openings 66, and a length of suture is left along the housing 12, between the two openings 32. With this threading, pulling on the first end of the length of suture will pull the fixation member carriage assembly 16 in one direction, and pulling on the second end of the length of suture will pull the fixation member carriage assembly 16 in the opposite direction.

The sutures or portions of the sutures may be color-coded. For example, the first suture may be colored green and the second suture may be colored red; of course any color scheme may be used so long as the sutures are visually distinct. Similarly, if one suture is used, different portions of the one suture may be color coded differently. In one example, the green color may be used to indicate that pulling on the green suture (or green portion) will deploy the fixation members and the red color may be used to indicate that pulling on the red suture (or red portion) will retract the fixation members. Also, portions of the suture(s) may be colored to a specific length in order to be used as visual indicators to show when the fixation members are fully deployed or retracted. For example, if all the red color is hidden because it has been drawn into the suture passage 86, that may provide indication that the fixation members are fully deployed. In some examples, only one suture, or one portion thereof, may be colored, a second portion or a second suture retaining its natural color.

In other embodiments, one or more sliding tabs, levers or other actuation features may be used instead of the sutures to move the fixation member carriage and/or deploy the one or more fixation members. The actuation features may push, pull, twist, or otherwise urge movement of the fixation member carriage and/or fixation members.

When the cap 14 is fitted to the housing 12, tabs 46 may fit into wall gaps 36, although inferior to each tab 46 an open portion of each gap can remain, the open portion sized to permit passage of the fixation member tip 84 and shaft 82. Fixation member carriage assembly 16 can thus be captured in an enclosure formed between the carriage track 26 and track cover 52. When the tissue fixation device 10 is in the retracted configuration, each fixation member 18 is substantially contained in a fixation member retention space 88 bounded by fixation member carriage 60, track cover 52, housing inner wall 34 and cap outer wall 50. In this configuration, each fixation member tip 84 is adjacent to, but not extending beyond, a wall gap 36. To move the device 10 into the deployed configuration, the appropriate suture is pulled, for example suture 90, and fixation member carriage assembly 16 will be pulled along carriage track 26 in direction 100. As the carriage assembly 16 travels along the circle defined by the housing, carrying fixation members 18, fixation member tips 84 will encounter ramp features 56 of bosses 54 and be forced, or deflected, through the open portions of wall gaps 36, thus being inwardly deployed. It is appreciated that a single movement, for example, pulling the suture 90, may deploy some or all of the fixation members simultaneously. The deployment paths of fixation members 18 may be coplanar in some embodiments, and the fixation members 18 may be deployed along a plane perpendicular to a lengthwise central axis 35 of the housing 12. The plane may also be described as transverse to the lengthwise central axis 35. The plane may also be coplanar with or parallel to the planar surface which is completely enclosed by the housing. When the fixation members 18 are deployed into tissue along paths transverse to the lengthwise central axis 35, this can advantageously result in fixing the position of the tissue within the housing 12, and preventing the tissue from subsequently translating relative to the device 10 along the lengthwise central axis. In other words, gripping the tissue from a lateral or transverse direction can prevent the tissue from moving longitudinally within, or even out of, the housing inner space 33.

In other embodiments, the fixation members 18 may move up and/or down out of a plane perpendicular to a lengthwise central axis 35 of the housing 12. In these embodiments, the deployment paths of the fixation members 18 may be parallel to the central housing axis, or at an acute angle to the axis; the paths themselves may be nonlinear, curved, helical, or the like.

The fixation members 18 may pierce tissue, such as cervical tissue, positioned in the housing inner space 33. Deployment can stop when the fixation member bases 80 become wedged between housing inner wall 34 and cap ramp feature 56. Another stop to the carriage motion may be formed when mounting feature 62 of the carriage assembly 16 encounters cap boss 54. Because of the wedging engagement of the fixation member bases between the housing 12 and cap 14, the deployed fixation members can be locked in the deployed configuration and remain deployed until they are intentionally retracted.

The fixation member tips 84 can be shaped similar to a hypodermic needle such that, minimum penetration force is needed to deploy the fixation members 18 into the tissue. Furthermore, in this example, when the three fixation members 18 are fully deployed, the fixation members 18 can engage with over 280 degrees of tissue, creating strong tissue fixation. Moreover, this embodiment allows the fixation members 18 to be close to the outer surface 44 of cap 14 which may serve as a cutting guide during colpotomy incisions. This allows the tissue fixation members to be less than about 0.25 inches from the cutting guide and the interiorly located fixation members 18 will not impinge on the cutting path. It will be appreciated that other size cutting guide tip designs can be made to adjust the distance and orientation of the cutting guide to achieve different incision placements as desired.

To move the device 10 into the retracted configuration, the second suture 92 is pulled. The fixation member bases 80 will be disengaged from the inner wall 34 and ramp feature 56, and fixation member carriage assembly 16 will be pulled in the opposite direction, or direction 102. As the carriage moves, the inner curved side of the shaft 82 of each fixation member will be forced outward as it encounters inner wall 34, and fixation members 18 will be retracted in through wall gaps 36.

Figure 9:
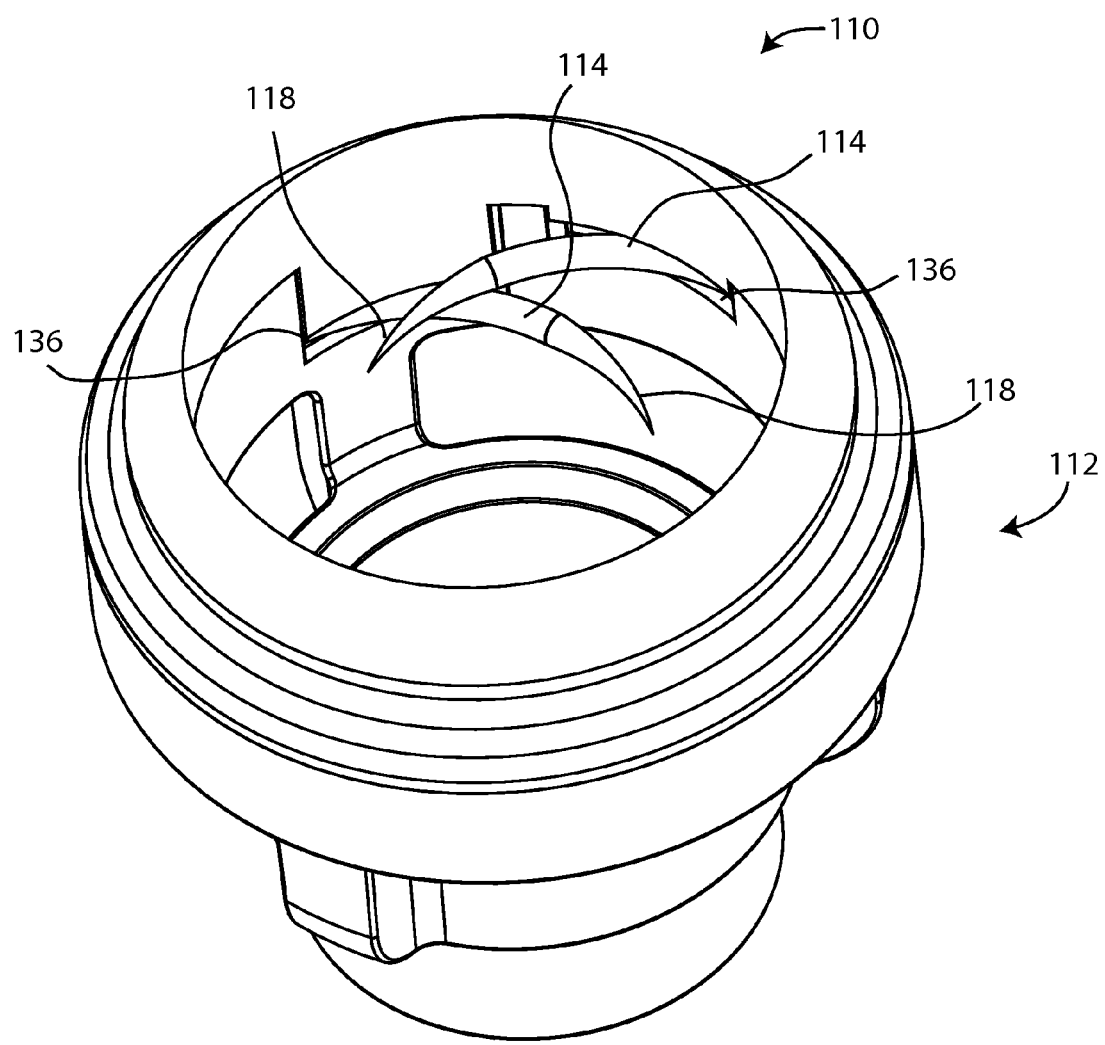
FIG. 9 is a perspective view of another tissue fixation device in accordance with the present disclosure with the tissue fixation members in the deployed configuration.
Figure 10:
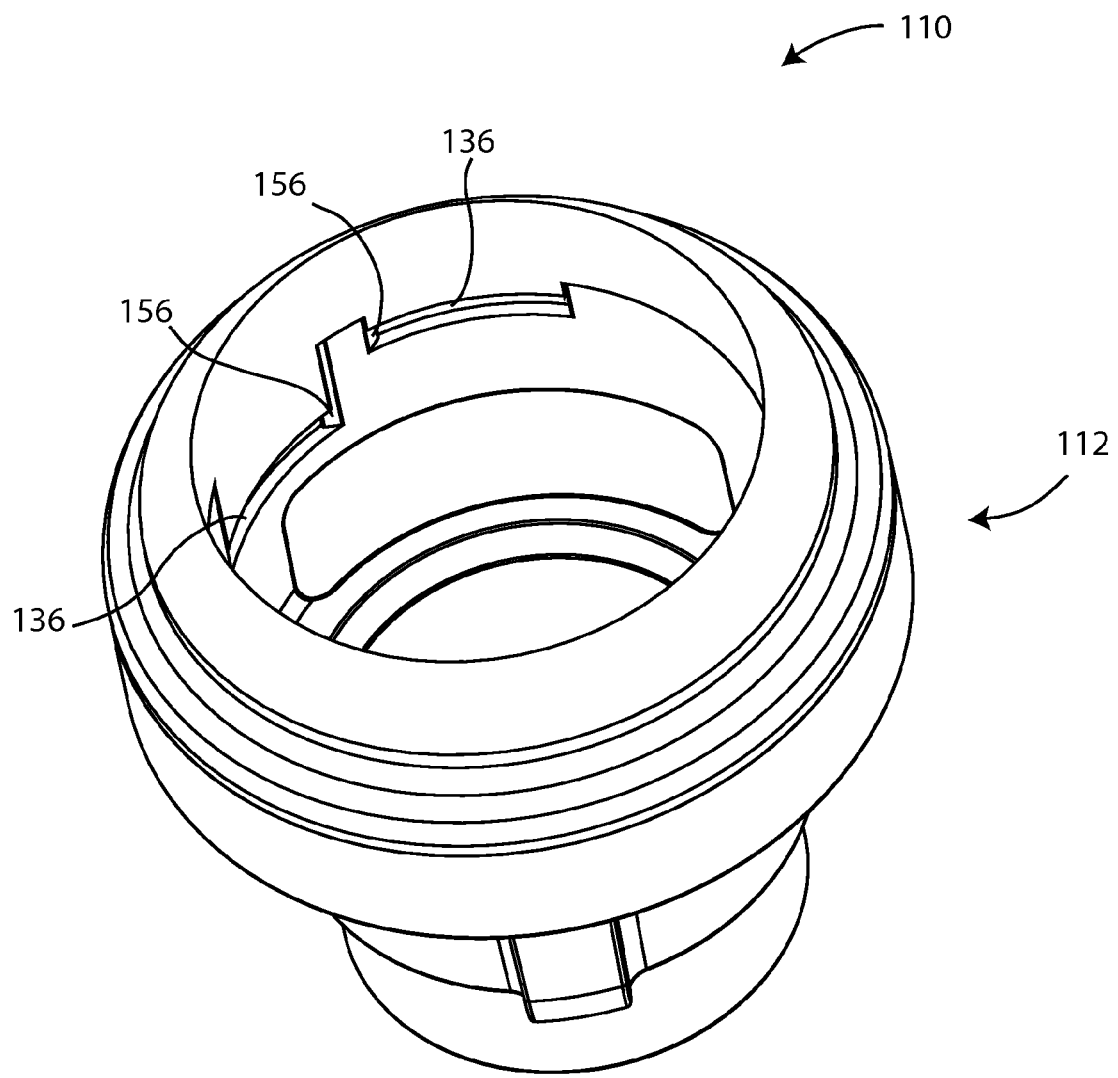
FIG. 10 is a perspective view of the tissue fixation device of FIG. 9 with the tissue fixation members in the retracted configuration.
Figure 11:
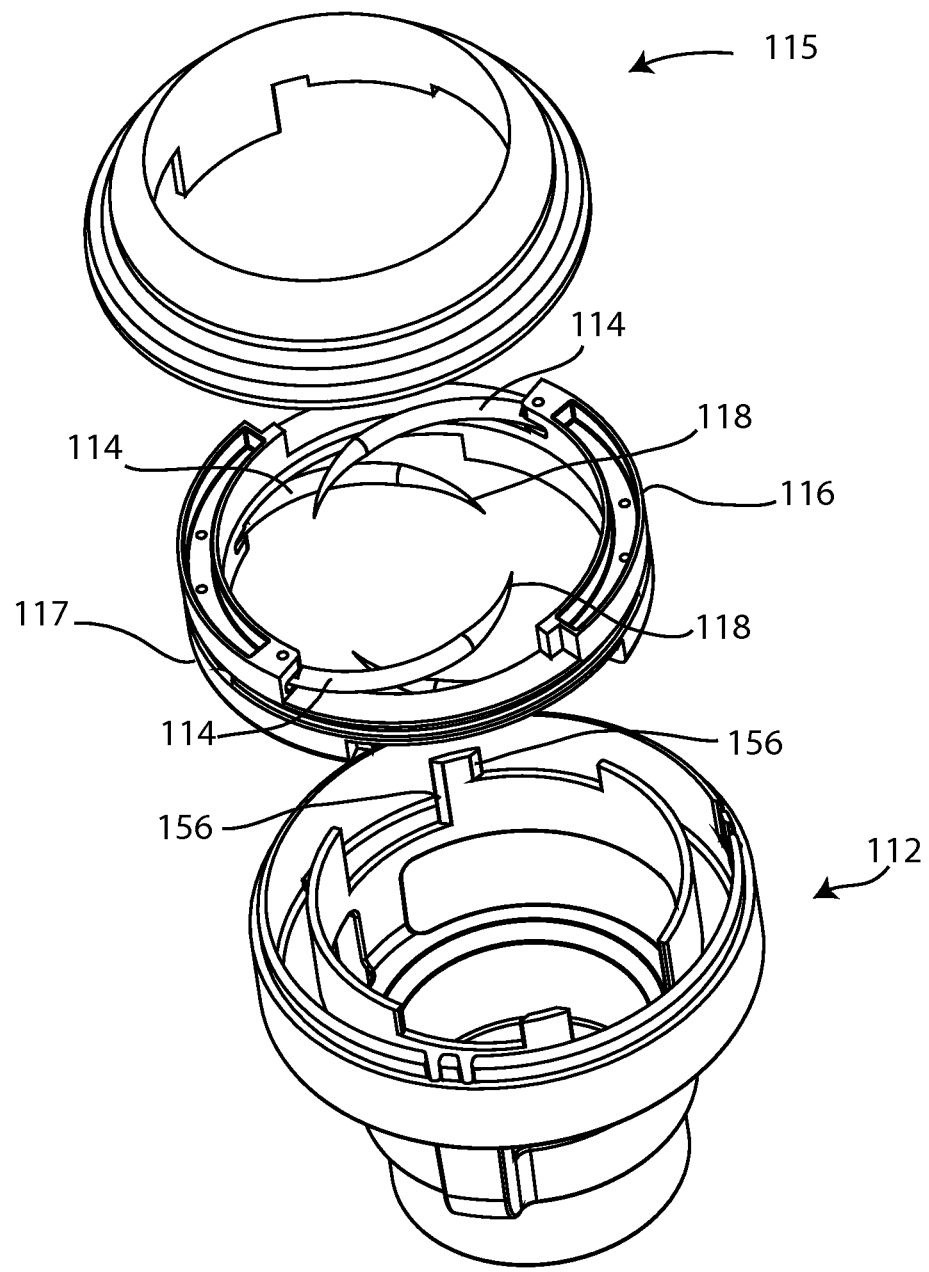
FIG. 11 is an exploded view of the tissue fixation device of FIG. 9.

FIGS. 9-20 show alternative embodiments of tissue fixation devices. FIGS. 9-11 show a tissue fixation device 110 having a housing 112, a cap 115, fixation member carriage 116 and at least two fixation members 114 which rotate into the deployed position in opposite directions. In this example, tissue fixation device 110 has four fixation members 114. Two of the fixation members rotate into the deployed position in the same direction and the other two fixation members rotate into the deployed position in the opposite direction; the second set of fixation members is also axially offset from the first set of fixation members. However, it will be understood that more or less fixation members 114 can be used in other embodiments without departing from the spirit or scope of the present disclosure. Similar to the example of FIGS. 1-8, the fixation members 114 can have beveled tips 118 which interact with ramp features (not shown) to force the fixation members inward toward the tissue as the fixation members 114 rotate into the deployed position, similar to other embodiments disclosed herein. The cap 115 can also have beveled edges 156 which may also help urge the fixation member 18 inward as it is deployed.

Operation of this tissue fixation device can be similar to that described above with reference to FIGS. 1-8, except that multiple fixation member carriages 116, 117 can be stacked on top of each other, with each of the fixation member carriages 116, 117 being free to rotate in opposite directions. In this example, two fixation member carriages 116, 117 are used. However, in other embodiments, more than two fixation member carriages can be used. Actuation of the fixation members 114 into the deployed position can be accomplished by any mechanical means disclosed herein. In one embodiment, a first suture (not shown) with one end split into two suture portions, or limbs, can be used with one of the split ends connected to the first fixation member carriage 116 in a first direction and the other split end connected to the second fixation member carriage 117 in a second direction. When the first suture is pulled, the two fixation member carriages 116, 117 will rotate in opposite directions relative to each other. A second suture (not shown) with one end split into two suture portions can be used to reverse the rotation of the two fixation member carriages with the split ends of the second suture connected to the fixation member carriages 116, 117 in opposite directions relative to the split ends of the first suture. Thus, when the second suture is pulled, this causes the two fixation member carriages to rotate in opposite directions relative to pulling the first suture.

Figure 12:
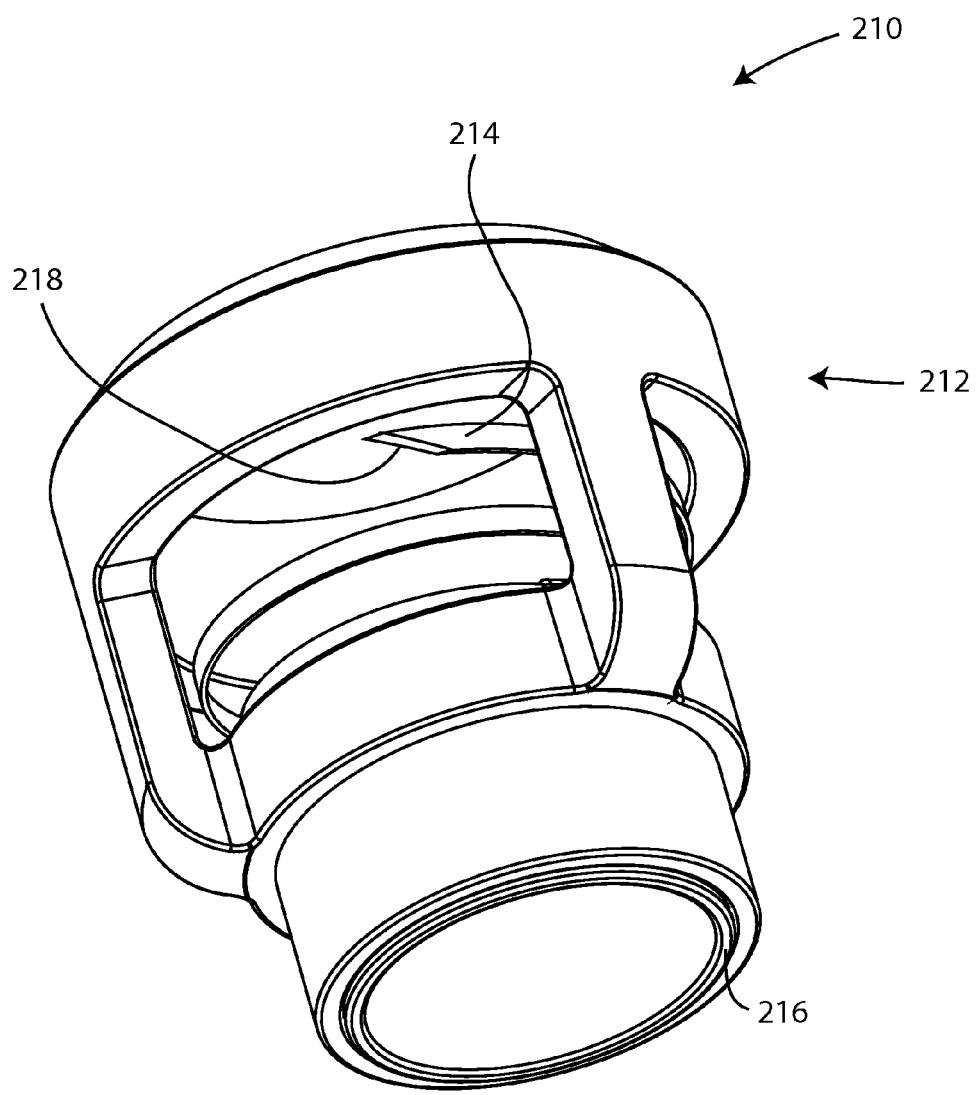
FIG. 12 is a perspective view of another tissue fixation device in accordance with the present disclosure with the tissue fixation member in the deployed configuration.
Figure 13:
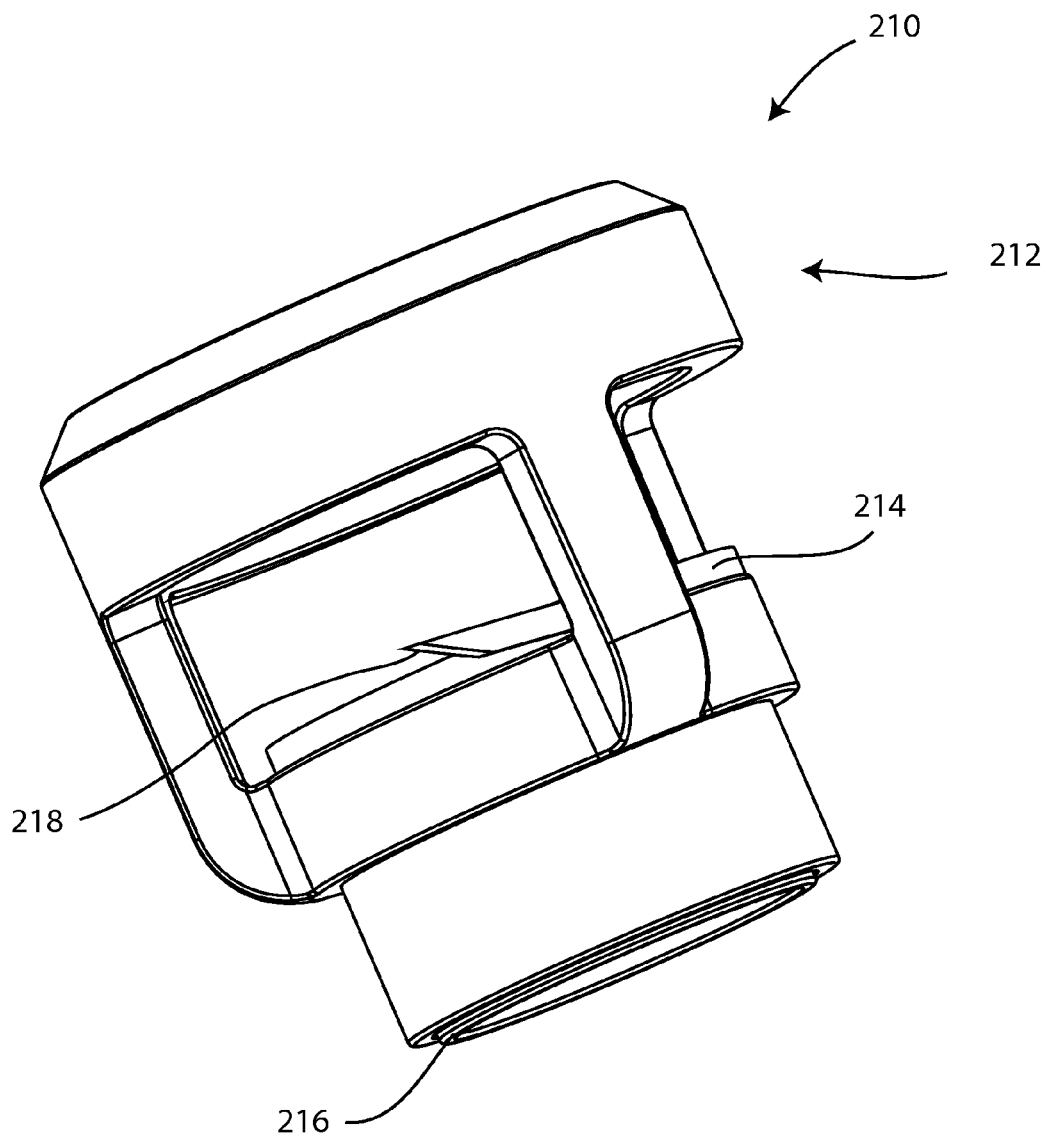
FIG. 13 is a perspective view of the tissue fixation device of FIG. 12 with the tissue fixation member in the retracted configuration.

FIGS. 12-13 show a tissue fixation device 210 having a housing 212, and a helical fixation member 214 which may be formed of a material such as Nitinol. FIG. 12 shows the helical fixation member 214 in the deployed position, and FIG. 13 shows the helical fixation member 214 in the retracted position. The helical fixation member 214 can be engaged with a rotatable carriage member 216. The helical fixation member can have a sharp beveled tip 218 that is angled upward toward the inserted tissue to help draw the fixation member 214 into the tissue as the fixation member is rotated into the deployed position.

In use, tissue may be received within housing 212, and the helical fixation member 214 can be rotatably advanced into the tissue by rotating carriage member 216 to engage and hold the tissue relative to the housing 212. It will be appreciated that helical fixation member 214 advances along a deployment path which includes a rotational component and an axial component relative to the center housing axis.

Figure 14:
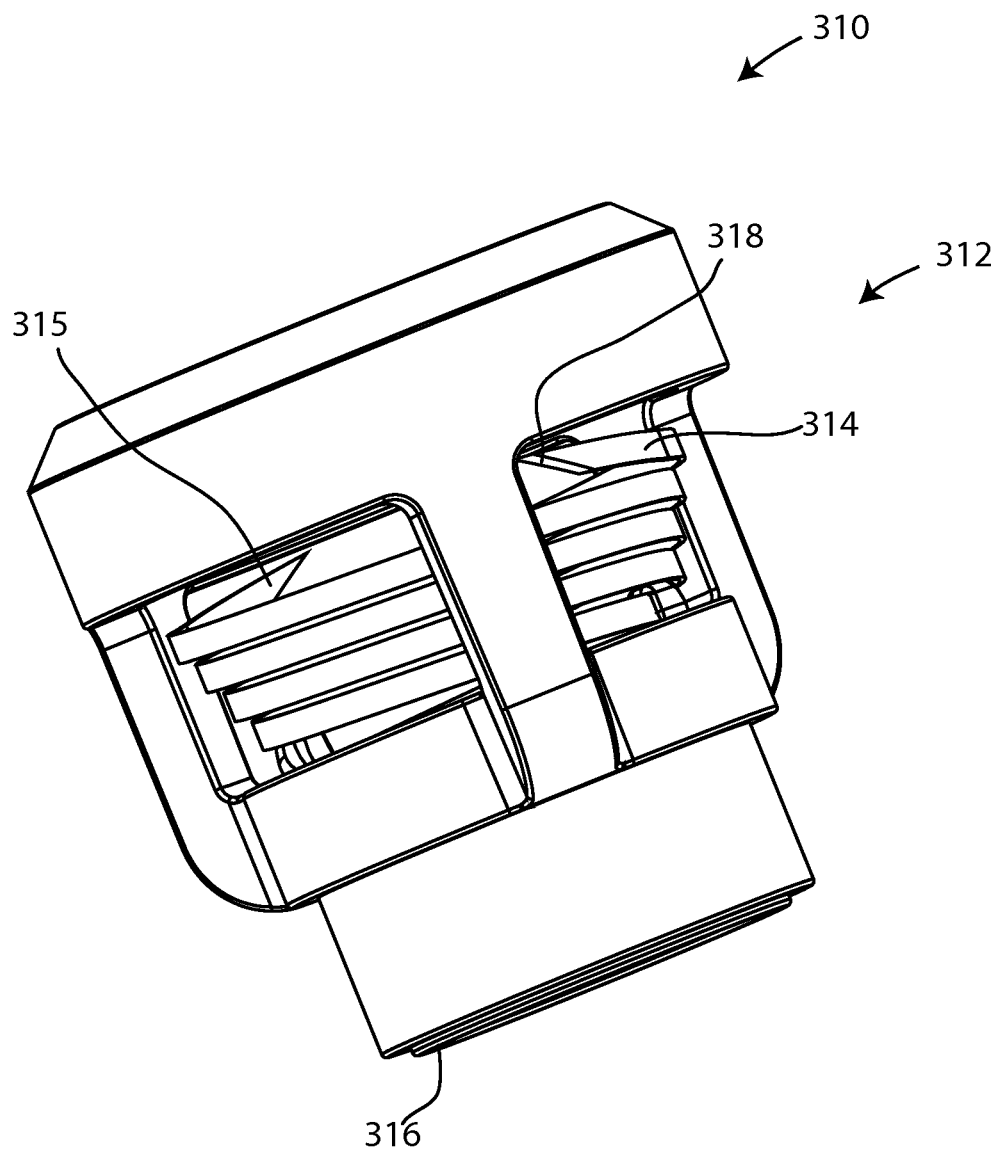
FIG. 14 is a perspective view of another tissue fixation device in accordance with the present disclosure with the tissue fixation members in the deployed configuration.
Figure 15:
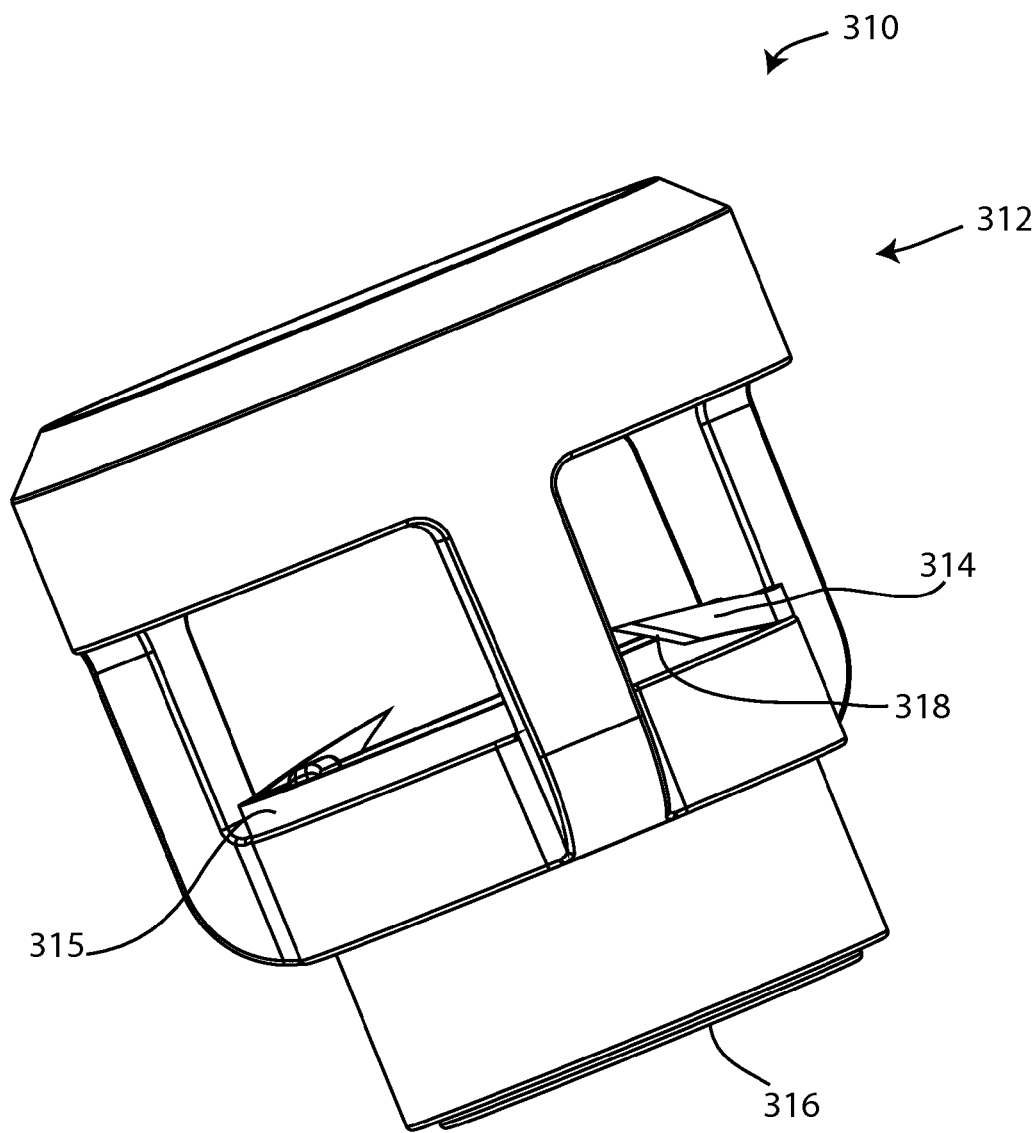
FIG. 15 is a perspective view of the tissue fixation device of FIG. 14 with the tissue fixation members in the retracted configuration.

FIGS. 14-15 show a tissue fixation device 310 having a housing 312, and multiple helical fixation members 314, 315 which may be formed of a material such as Nitinol. FIG. 14 shows the helical fixation members 314, 315 in the deployed position, and FIG. 15 shows the helical fixation members 314, 315 in the retracted position. The helical fixation members 314, 315 can be engaged with a rotatable carriage member 316. The helical fixation members 314, 315 can have sharp beveled tips 318 that are angled upward toward the inserted tissue to help draw the fixation members 314, 315 into the tissue as the fixation members 314, 315 are rotated into the deployed position. The sharp beveled tips 318 of each of the helical fixation members 314, 315 can be positioned out of phase with each other by 180 degrees.

In use, tissue may be received within housing 312, and the helical fixation members 314, 315 can be rotatably advanced into the tissue by rotating carriage member 316 to engage and hold the tissue relative to the housing 312. It will be appreciated that helical fixation members 314, 315 advance along a deployment path which includes a rotational component and an axial component relative to the center housing axis. It will be appreciated that other embodiments may include more than two helical fixation members without departing from the spirit or scope of the present disclosure.

Figure 16:
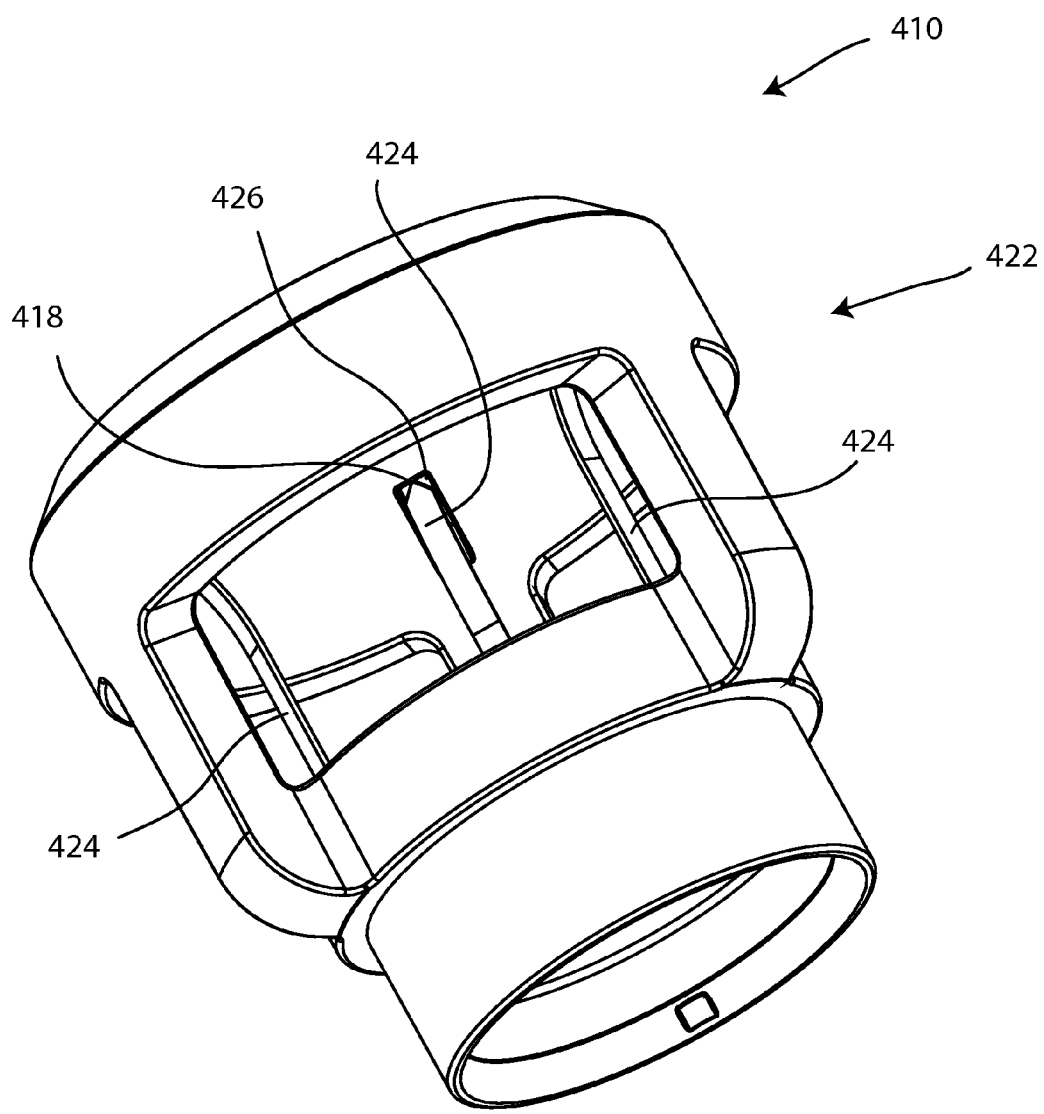
FIG. 16 is a perspective view of another tissue fixation device in accordance with the present disclosure with the tissue fixation members in the deployed configuration.
Figure 17:
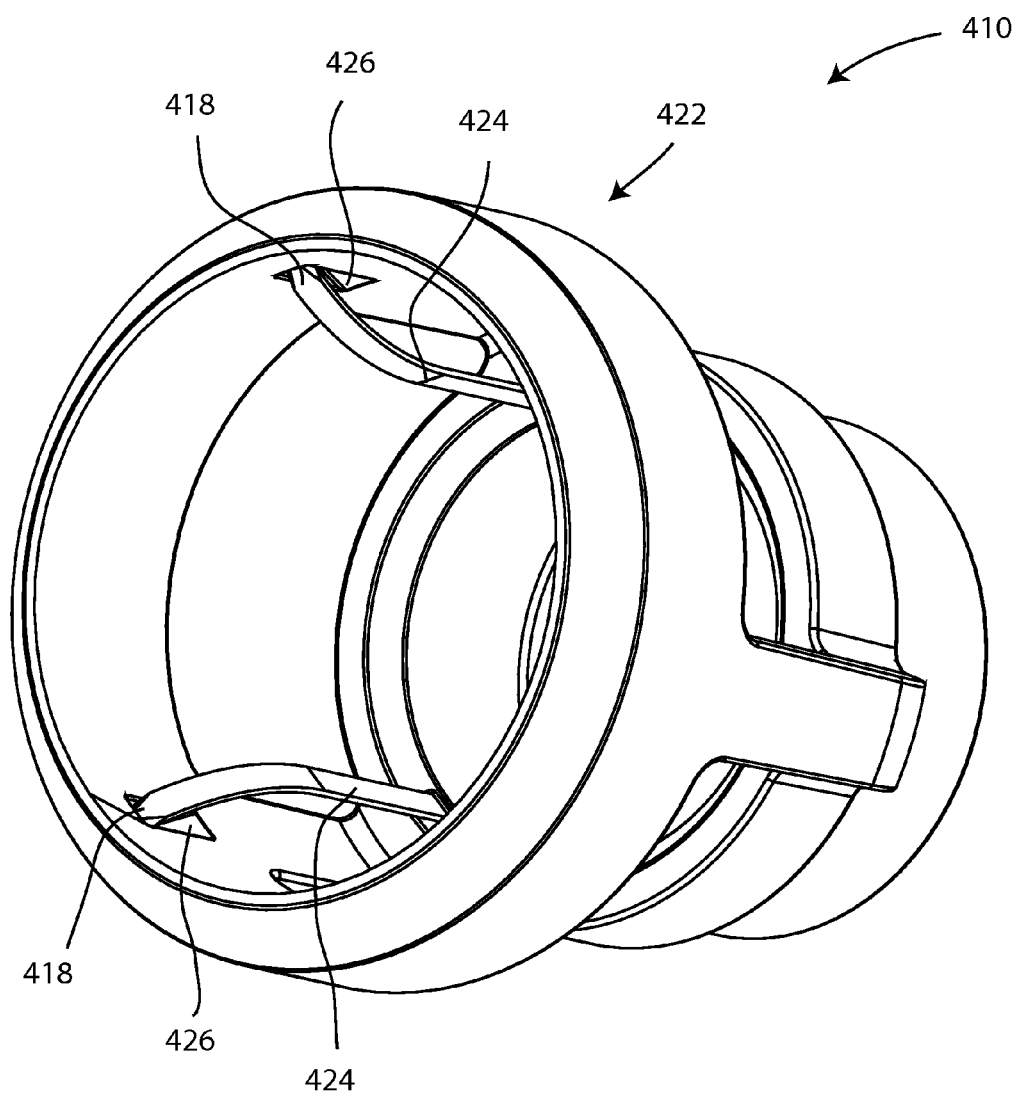
FIG. 17 is another perspective view of the tissue fixation device of FIG. 16 with the tissue fixation members in the deployed configuration.
Figure 18:
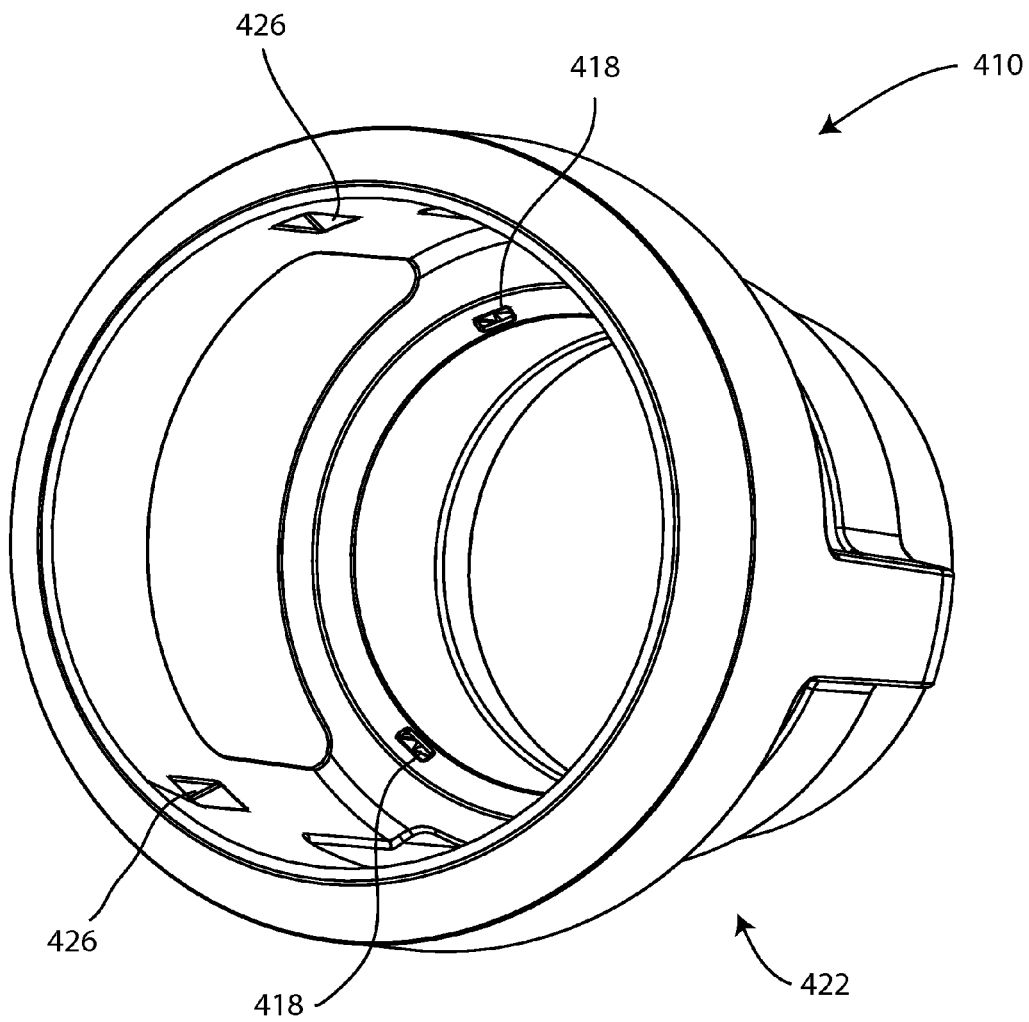
FIG. 18 is a perspective view of the tissue fixation device of FIG. 16 with the tissue fixation members in the retracted configuration.

FIGS. 16-18 show a tissue fixation device 420 having a housing 422 and at least one curved fixation member 424. In this embodiment there are three curved fixation members 424, however, other embodiments may include more or fewer curved fixation members 424. FIGS. 16 and 17 show the curved fixation members 424 in the deployed position and FIG. 18 shows the curved fixation members 424 in the retracted position. The curved fixation members 424 may be flexible, semi-flexible, or rigid. The curved fixation members 424 may be advanced upward from the housing 422, through tissue, and the tips 418 of the curved fixation members 424 may then be received in capture features 426 formed in the housing 422 to hold the tissue relative to the housing 422. Other embodiments may reverse the deployment direction of the curved fixation members 424. For example, the curved fixation members 424 may be advanced downward from the housing 422, through tissue, such that the tips 418 of the curved fixation members 424 are received in capture features 426 formed in the lower portion of the housing 422. In this embodiment, the position of the apertures where the curved fixation members 424 exit the housing and the capture features 426 are reversed. In other embodiments, the curved fixation members 424 may be advanced sideways from the housing 422 and into capture features 426 formed on the sides of the housing 422 such that the apertures where the curved fixation members 424 exit the housing and the capture features 426 lie in a plane substantially perpendicular to the lengthwise central axis of the housing 422.

Figure 19:
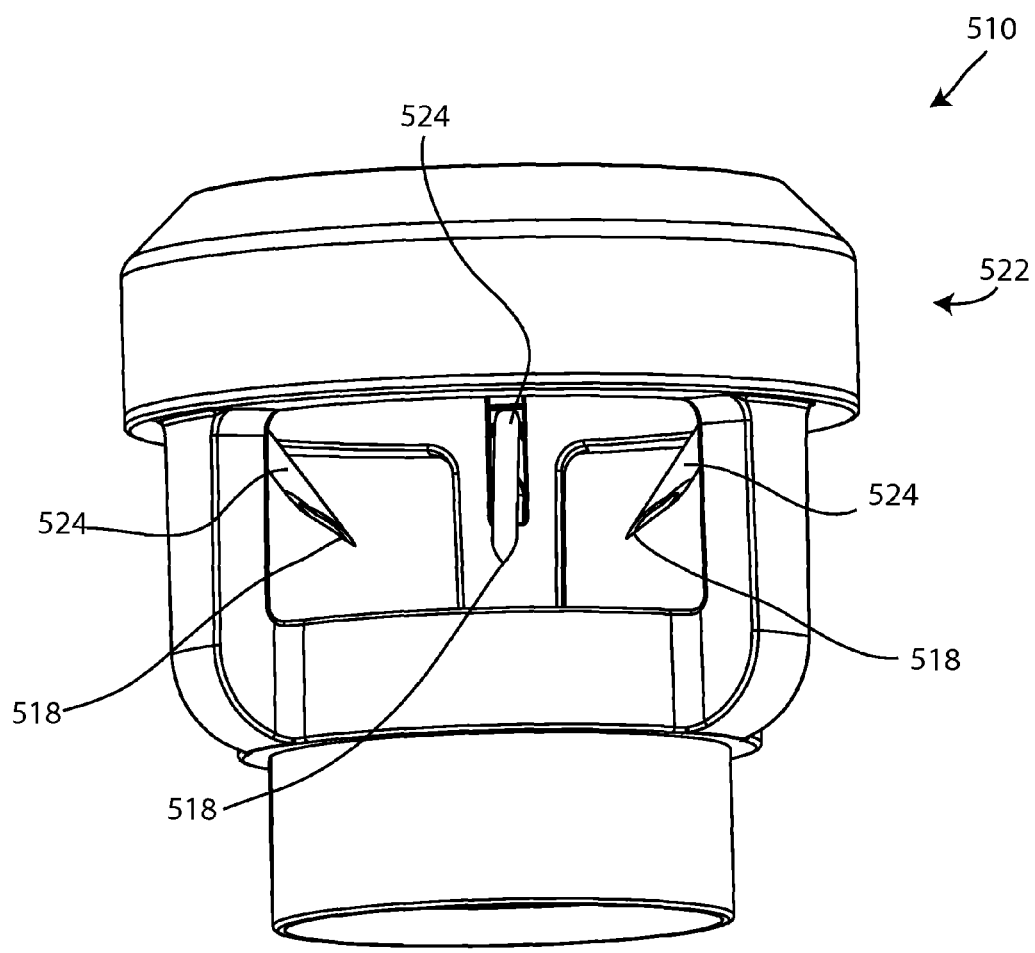
FIG. 19 is a perspective view of another tissue fixation device in accordance with the present disclosure with the tissue fixation members in the deployed configuration.
Figure 20:
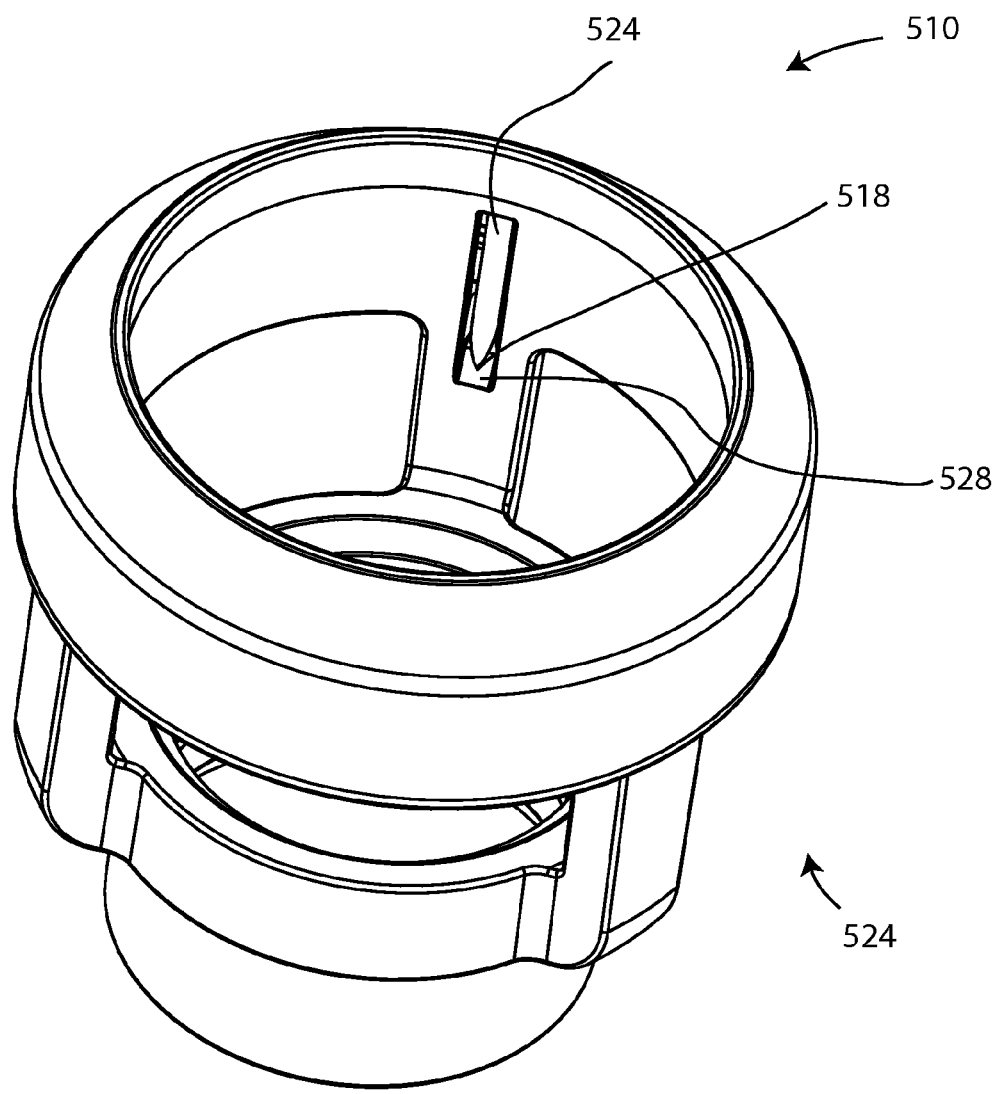
FIG. 20 is a perspective view of the tissue fixation device of FIG. 19 with the tissue fixation members in the retracted configuration.
Figure 21:
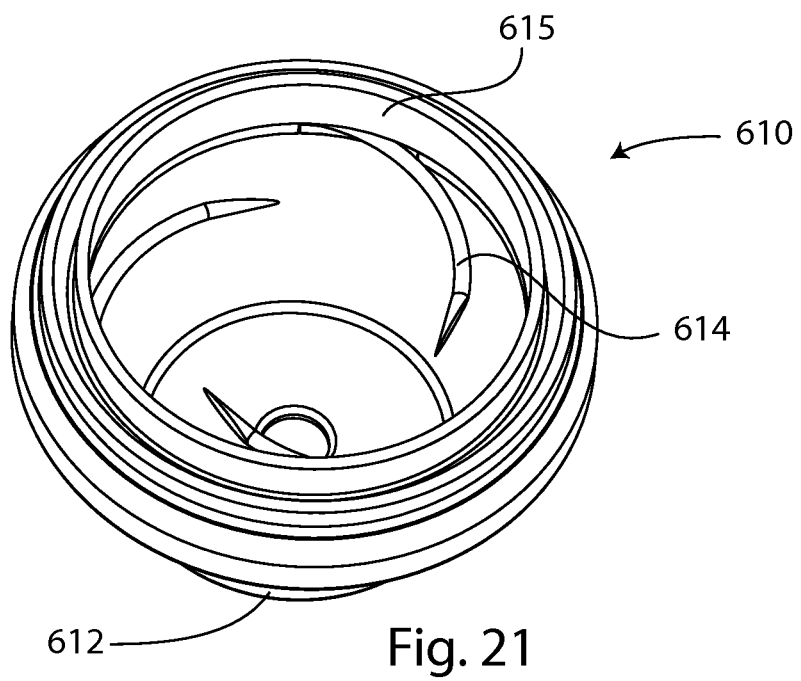
FIG. 21 is a perspective view of a tissue fixation device having a cap attached by a snap fit, the device in a deployed configuration.
Figure 22:
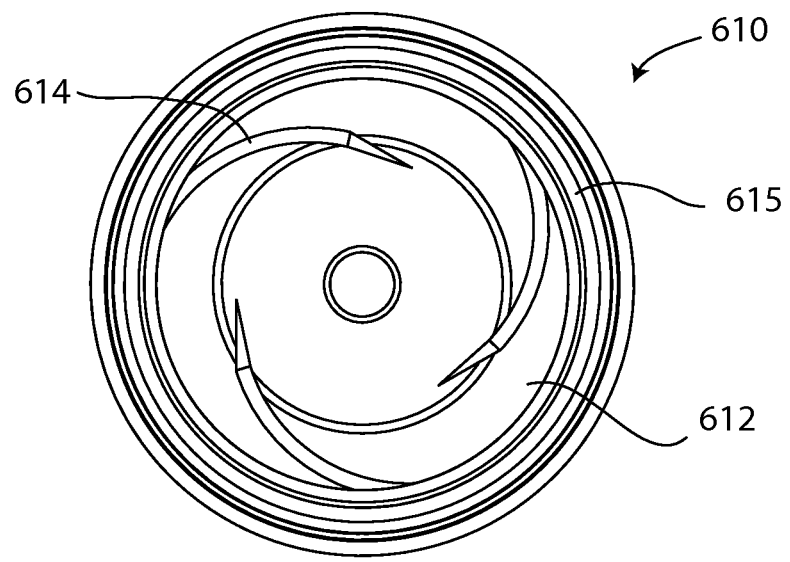
FIG. 22 is a top-down view of the tissue fixation device of FIG. 21.
Figure 23:
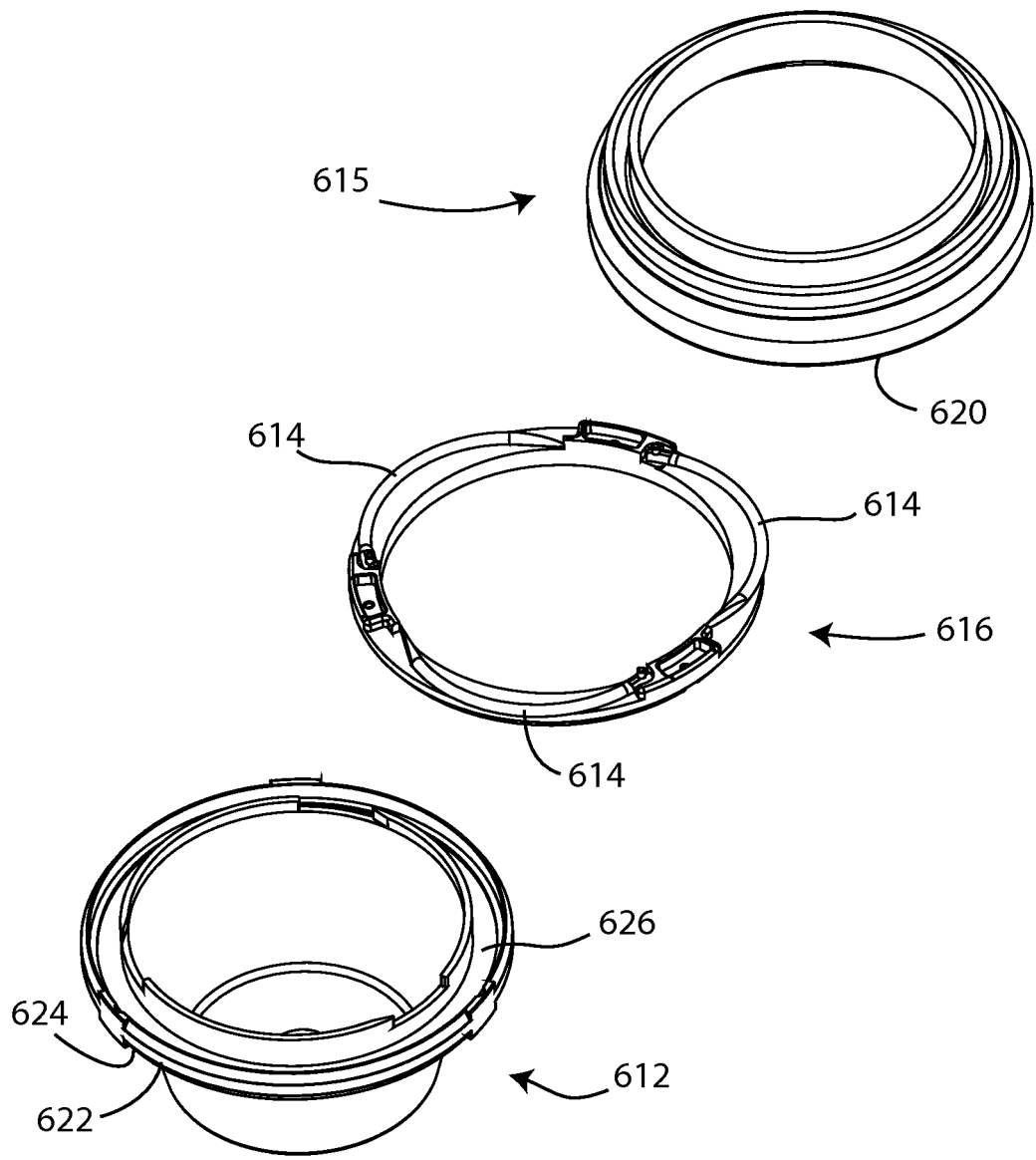
FIG. 23 is an exploded view of the tissue fixation device of FIG. 21 showing a housing, fixation member carriage, fixation members, and cap of the device.
Figure 24:
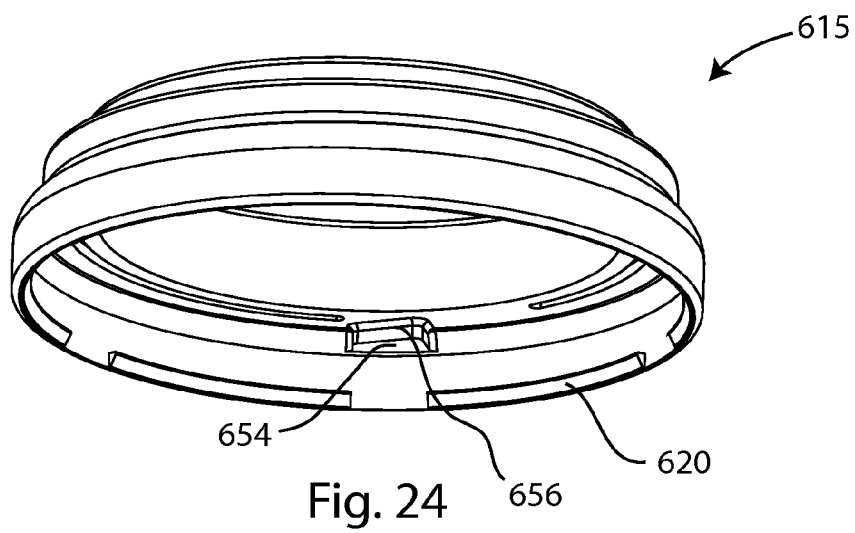
FIG. 24 is a perspective view of the cap of FIG. 23.
Figure 25:
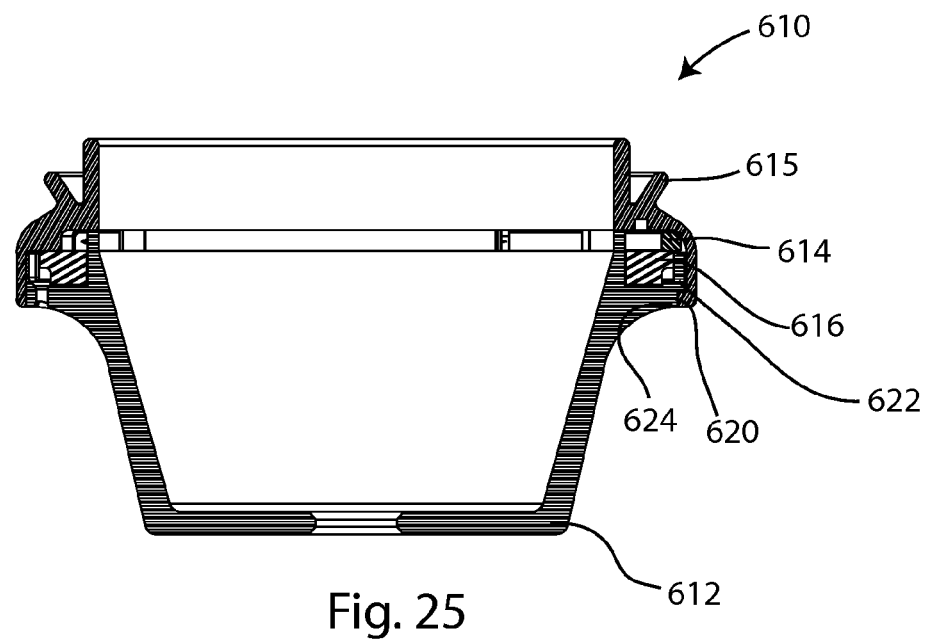
FIG. 25 is a side cross-sectional view of the tissue fixation device of FIG. 21.
Figure 26:
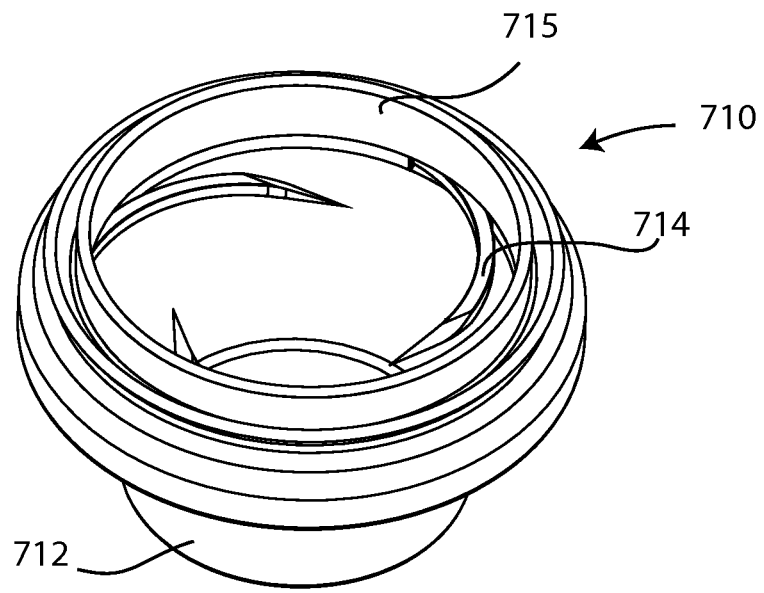
FIG. 26 is a perspective view of a tissue fixation device having a cap attached by a twisting fit, the device in a deployed configuration.
Figure 27:
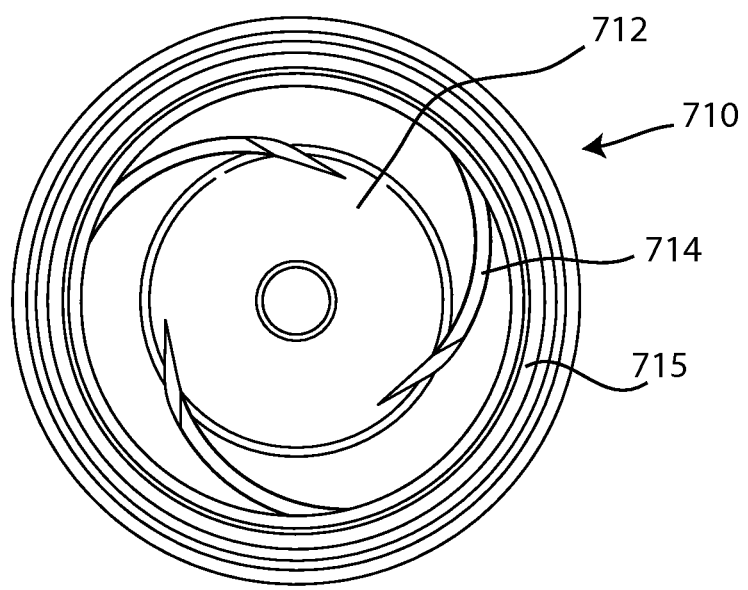
FIG. 27 is a top-down view of the tissue fixation device of FIG. 26.
Figure 28:
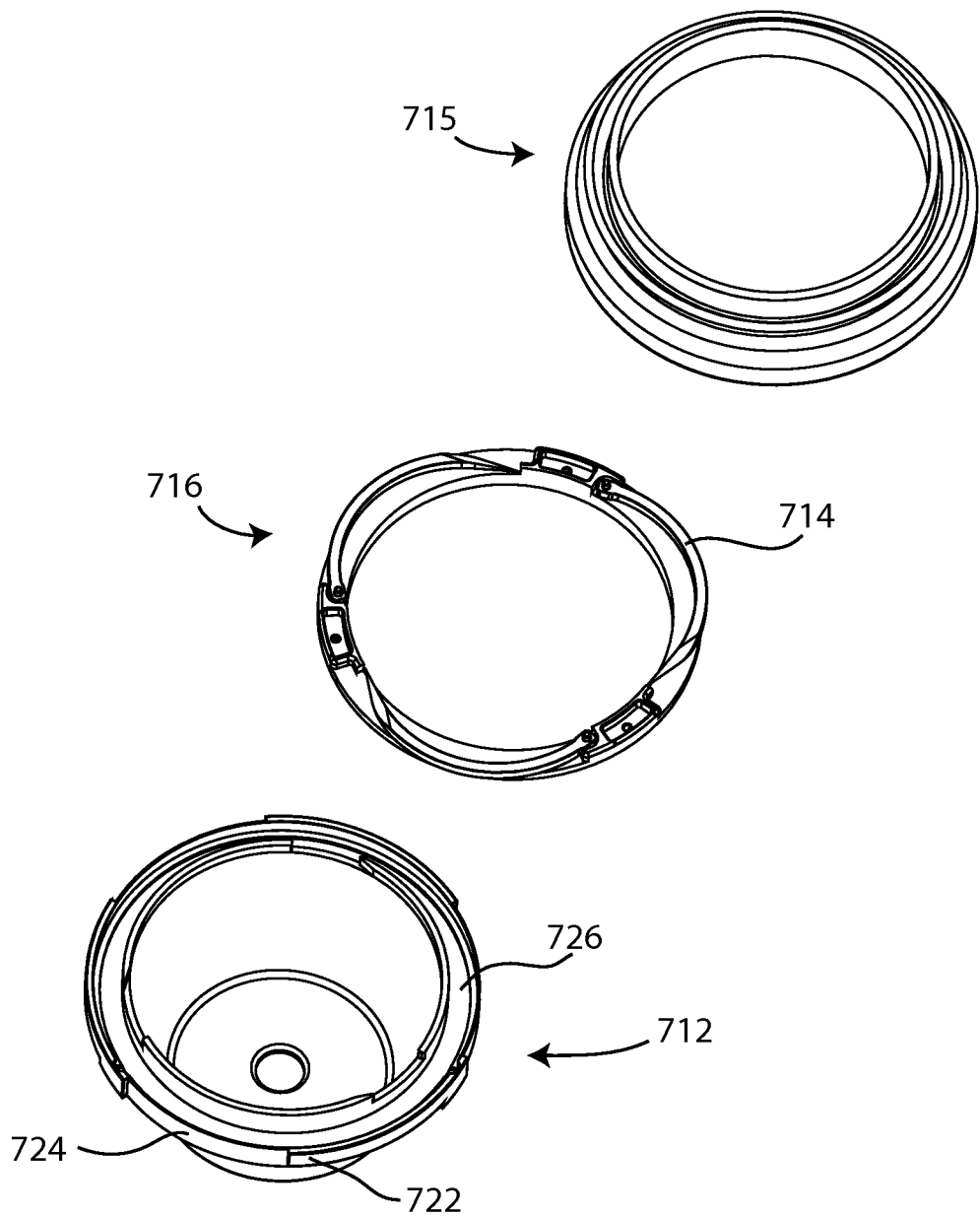
FIG. 28 is an exploded view of the tissue fixation device of FIG. 27 showing a housing, fixation member carriage, fixation members, and cap of the device.
Figure 29:
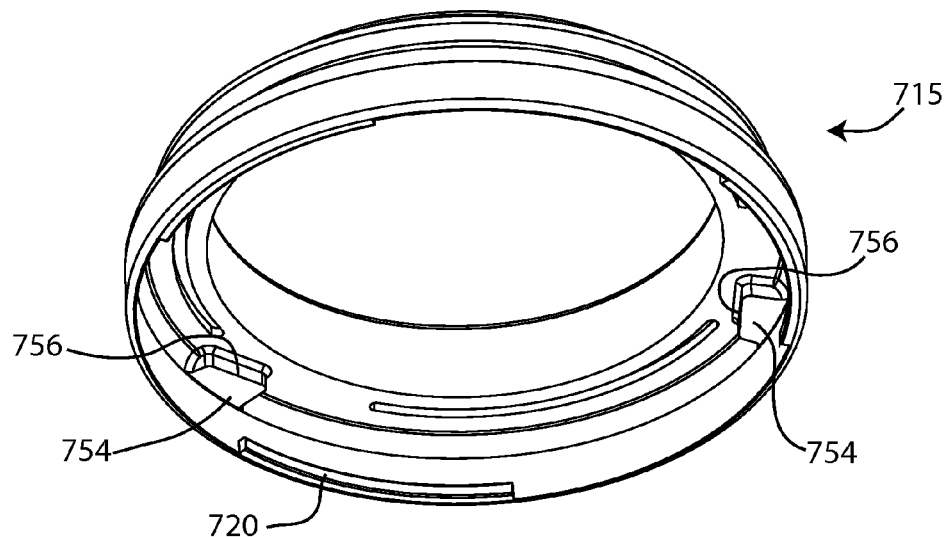
FIG. 29 is a perspective view of the cap of FIG. 28.
Figure 30:
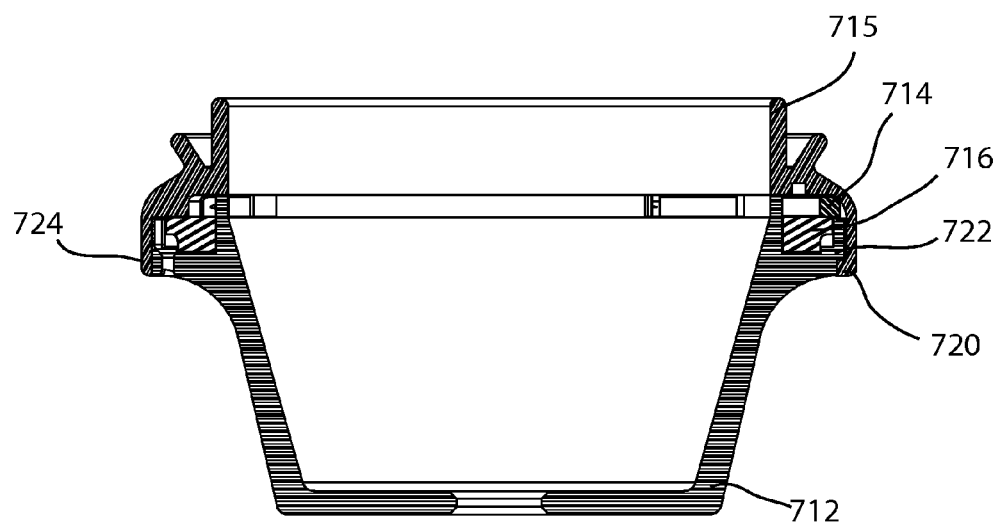
FIG. 30 is a side cross-sectional view of the tissue fixation device of FIG. 26.
Figure 31A:
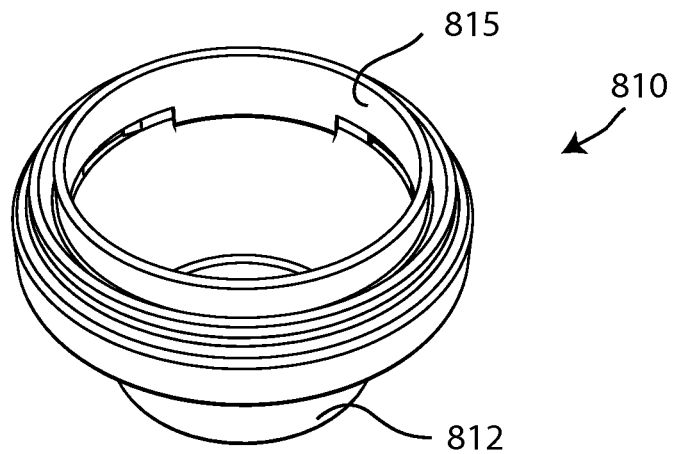
FIG. 31A is a perspective view of another embodiment of a tissue fixation device having a housing, a fixation member carriage assembly and a cap, with tissue fixation members in a retracted configuration.
Figure 31B:
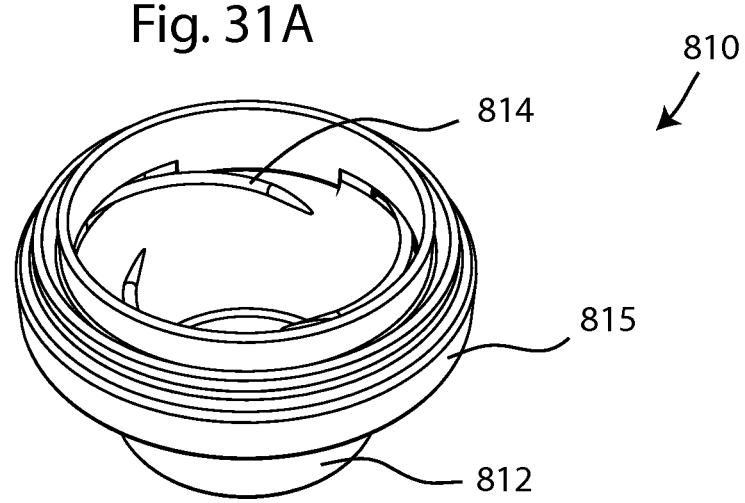
FIG. 31B is a perspective view of the device of FIG. 31B with the tissue fixation members in a deployed configuration.
Figure 31C:
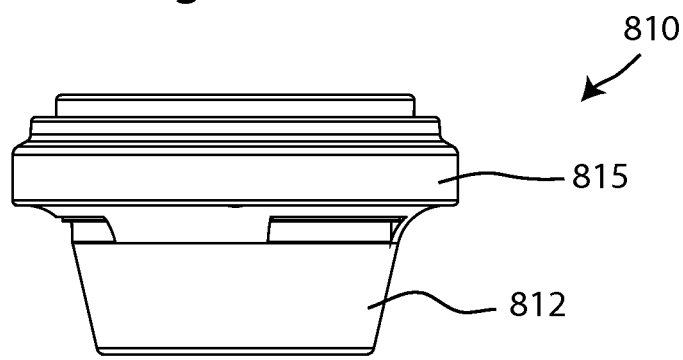
FIG. 31C is a side view of the device of FIG. 31A.

FIGS. 19-20 show a tissue fixation device 510 having a housing 522 and one or more fixation members 524. In this example there are three fixation members, however in other examples there may be more or fewer fixation members 524. FIG. 19 shows the tissue fixation device 510 with the fixation members 524 in the deployed position. FIG. 20 shows the tissue fixation device 510 with the fixation members 524 in the retracted configuration. The housing can have angled ramps 528 formed near the beveled tips 518 of the fixation members 524 which force the fixation members toward the center of the tissue fixation device 510 and into the tissue as the fixation members 524 are moved into the deployed position. The fixation members 524 can be moved between the deployed and retracted positions by means discussed herein including sutures, levers, sliding tabs, translating members or any other suitable mechanical means.

FIGS. 21-25 illustrate an alternative embodiment of a tissue fixation device 610. The tissue fixation device 610 includes a housing 612, a cap 615, and a fixation member carriage assembly 616 which carries at least one fixation member 614. In the example, the fixation members 614 are needles formed from round stock and have pointed tips. In some embodiments, the needles may be hypodermic needles. The fixation member carriage assembly 616 is captured between the housing 612 and cap 615, and is rotatable within a track 626 formed in the housing 612 and/or the cap 615 to deploy and retract the fixation members, in the same manner as described for device 10. The housing may be referred to as a bell housing. The fixation members 614 are movable between a deployed configuration seen in FIGS. 21 and 22 and a retracted configuration seen in FIGS. 23 and 24. The cap 615 attaches to the housing 612 via an interference fit which is a snap fit. To provide the interference fit, at least one flange 620 on the cap 615 engages with a shoulder 622 and recess 624 on the housing 612. During assembly, the cap 615 is aligned with housing 612 with flange 620 adjacent shoulder 622. The cap is pushed against the housing so that flange 620 moves past shoulder 622 and snaps into the recess 624 immediately below the shoulder 622. Cap 615 includes one or more bosses 654 with ramps 656 which deflect portions of the fixation members out of the track and housing when the carriage assembly 616 is rotated.

FIGS. 26-30 illustrate an alternative embodiment of a tissue fixation device 710. The tissue fixation device 710 includes a housing 712, a cap 715, and a fixation member carriage assembly 716 which carries at least one fixation member 714. In the example shown, the fixation members 714 are needles stamped from flat stock, and have pointed tips. The fixation member carriage assembly 716 is captured between the housing 712 and cap 715, and is rotatable within a track 726 formed in the housing 712 and/or the cap 715 to deploy and retract the fixation members, in the same manner as described for device 10. The housing may be referred to as a bell housing. The fixation members 714 are movable between a deployed configuration seen in FIGS. 26 and 27 and a retracted configuration seen in FIGS. 28 and 30. The cap 715 attaches to the housing 712 via an interference fit which is a twisting fit. To provide the interference fit, at least one flange 720 on the cap 715 engages with shoulders 722 and recesses 724 on the housing 712. The shoulders 722 may alternate with the recesses 724. During assembly, the cap 715 is aligned with housing 712 with flanges 720 fitting into recesses 724. The cap 715 is twisted so that upon rotation, each flange 720 moves out of its respective recess 724 and is captured under shoulder 722. If the cap is twisted the opposite direction, the flanges are released from under the shoulders and the cap may be detached. Cap 715 includes one or more bosses 754 with ramps 756 which deflect portions of the fixation members out of the track and housing when the carriage assembly 716 is rotated.

A method of use may be the same for devices 610 and 710. In a method of use of device 710, tissue is positioned in a central opening 708 of housing 712. Carriage 716 is rotated in a first direction to deploy fixation members 714. One or more sutures 90, 94 or other lines may be used to rotate the carriage and deploy the needles, as described herein with regard to device 10 and FIGS. 7A and 7B. Fixation members 714 deflect circumferentially inward of the housing 712 and pierce the tissue, capturing the tissue and fixing it relative to the device 710. At this point, the device 710 may be moved to manipulate the tissue as desired. After desired tissue movement has been carried out, the carriage 716 is rotated in a second direction to retract the fixation members 714. The needles are pulled out of the tissue and back into the needle track 726, and the tissue is released from capture.

In some examples of use, the tissue is cervical tissue. The method of use may further include inserting a rod, tube or other elongated member (not shown) through the opening in the bottom of the housing, and into the cervix, with a portion of the elongated member extending out of the opening. After the needles are deployed, and the tissue is fixed relative to the device 610 or 710, the portion of the elongated member extending out of the opening may be manipulated to move the attached device and cervical tissue.

FIGS. 31A-36B illustrate another embodiment of a tissue fixation device. Device 810 can include a housing 812, a cap 815, and a fixation member carriage assembly 816 which carries at least one fixation member 814. In some examples, the fixation member 814 may be a needle. The fixation member carriage assembly 816 can be captured between the housing 812 and cap 815, and may be rotatable within a track 826 formed in the housing 812 and/or the cap 815. It is appreciated that many of the features and characteristics described for device 10 are found on and also apply to device 810.

The cap 815 and housing 812 may be referred to as a bell cap or a bell housing, respectively, as they may form a bell shape in some examples. The housing 812 includes at least one enclosed section that completely encloses at least one planar surface. The at least one planar surface can be defined by a cross-sectional plane through the housing that results in a planar surface that is completely enclosed or surrounded by a portion of the housing. In other words, the planar surface is an empty plane that is completely bounded by the housing 812. For example, with reference to FIG. 31C, if a cross section of the housing 812 is taken perpendicular to the longitudinal central axis 35 and through the top portion of the housing, or the cap 815, a circular planar surface would be created which lies within the opening, or inner space 33 of the housing 812 and which is completely bounded by or surrounded by the housing 812 or cap 815.

Figure 32:
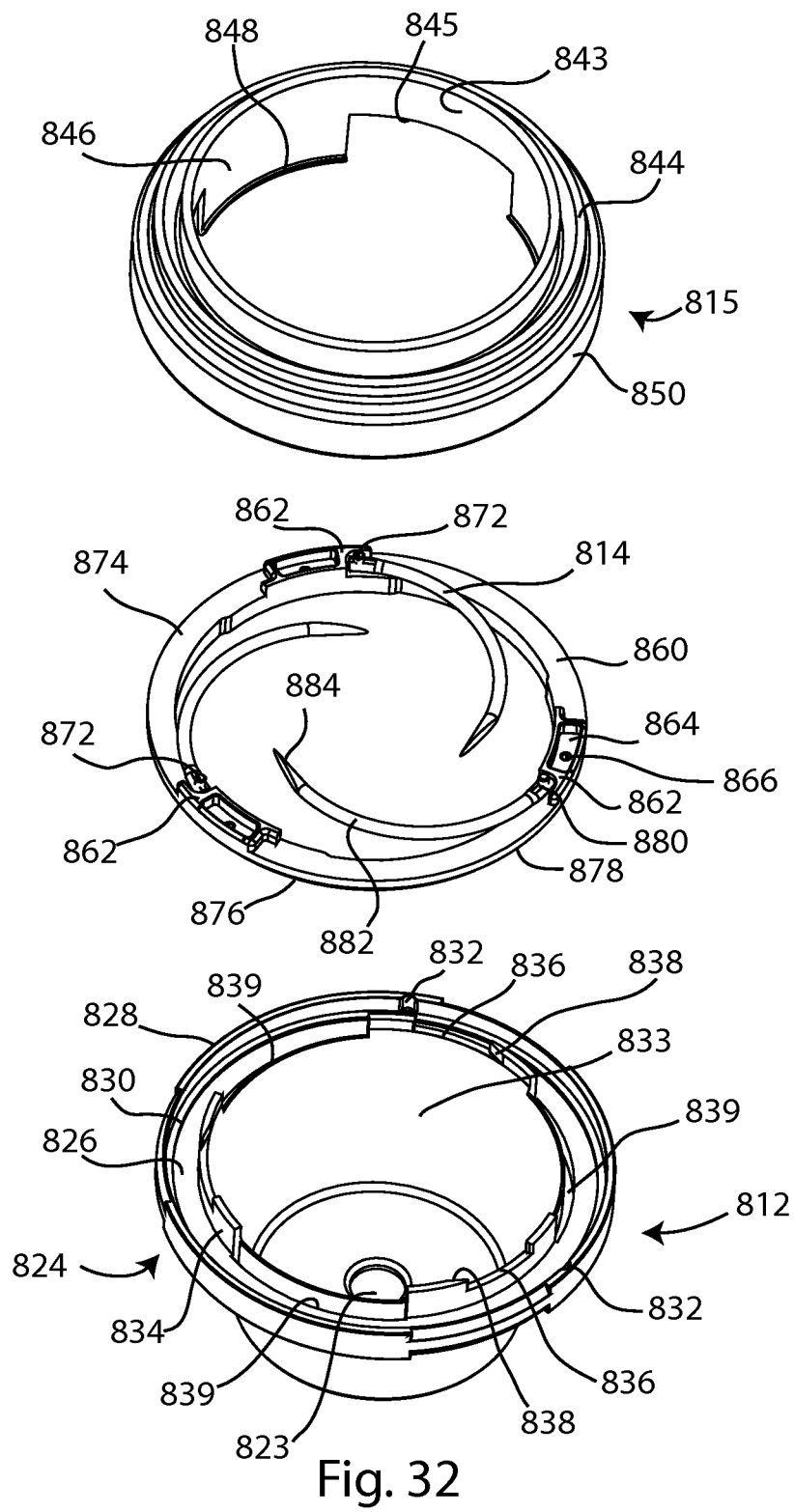
FIG. 32 is an exploded view of the device of FIG. 31A.
Figure 33:
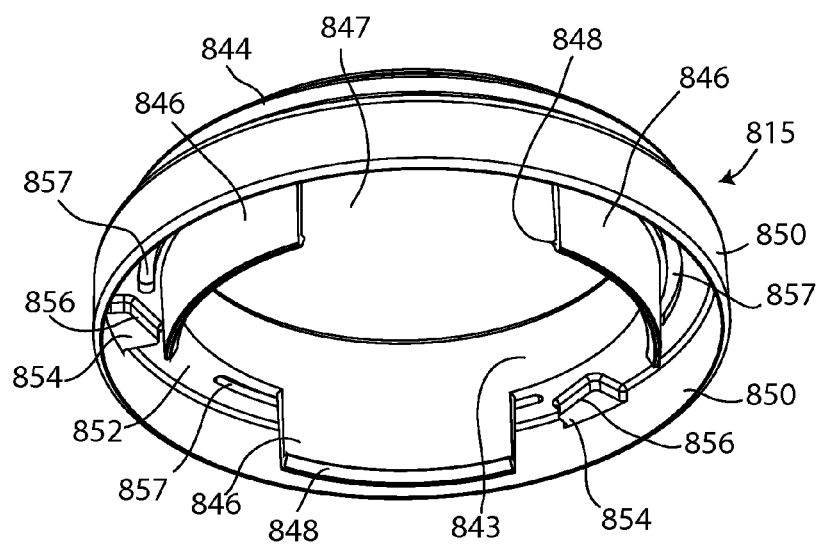
FIG. 33 is a perspective view of a cap of the device of FIG. 31A.
Figure 34:
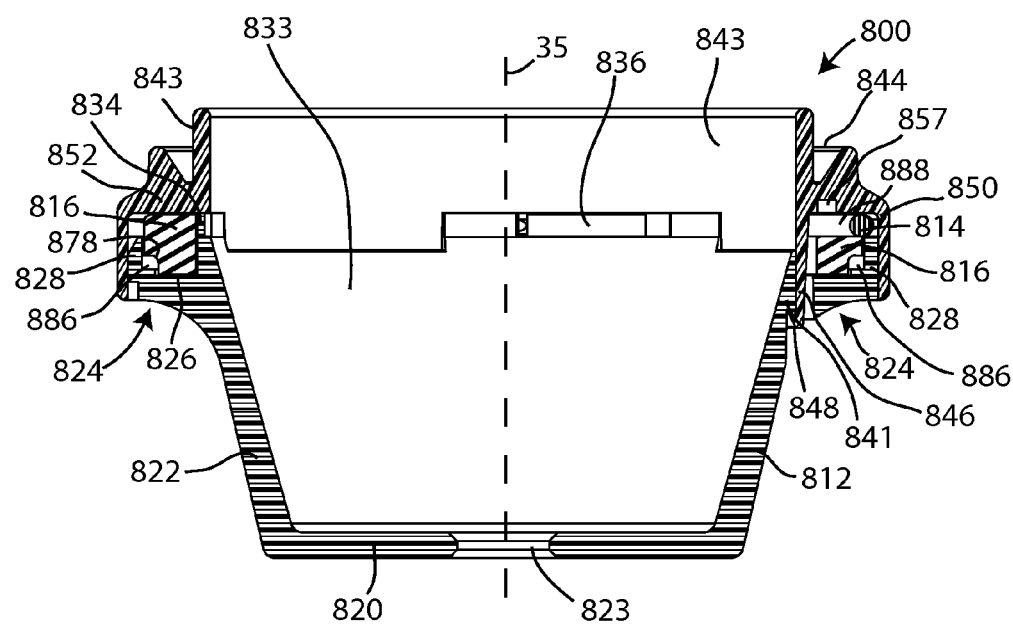
FIG. 34 is a side cross-sectional view of the tissue fixation device of FIG. 31A.
Figure 35A:
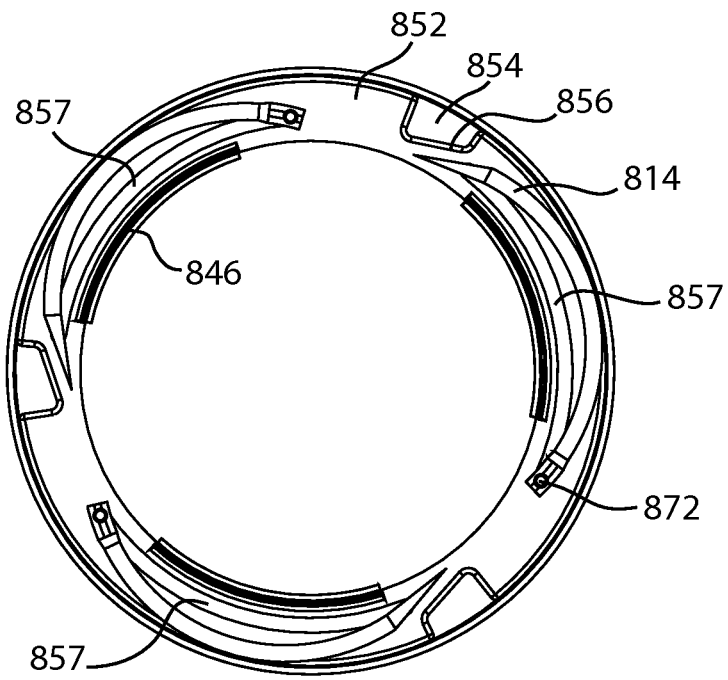
FIG. 35A is an inferior view of the cap and fixation members of the device of FIG. 31A.
Figure 35B:
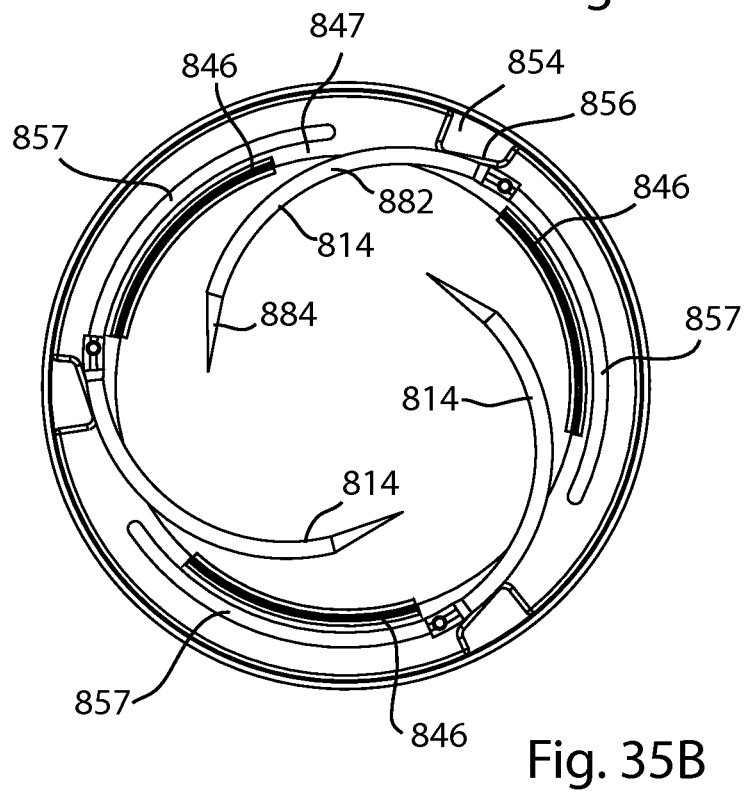
FIG. 35B is an inferior view of the cap and fixation members of the device in the configuration of FIG. 32A.

Referring to FIGS. 32 and 34, housing 812 is substantially frustoconical and circular in shape. However, the housing 812 can also be conical, cylindrical, funnel, ovoid, or polygonal in shape, or any combination of shapes thereof. The housing may include a base 822 which may be circular, and a peripheral support wall 822 which terminates at a carriage support 824. In the example shown, the base 822 has the narrowest diameter of the housing, and the housing slopes outward to a widest diameter at the carriage support 824. Housing 812 may include an opening 823 which may be shaped to engage with uterine manipulator (not shown). The peripheral wall 834 and base 822 may surround and define a housing inner space 833. The lengthwise central axis 35 may extend through the housing inner space 833, also defined by the peripheral wall 834 and base 822.

The carriage support 824 can be ring-shaped, and include a carriage track 826, which may be substantially circular. An outer rim 828 circumscribes the outer diameter of carriage track 826, and a step 830 may be formed intermediate the track 826 and the outer rim 828. One or more apertures 832 can open through the carriage support 824, and may pass through at least a portion of the outer rim 828 and step 830. A housing inner wall 834 can circumscribe the inner diameter of the carriage track 826, and may include a plurality of discontinuations, or wall gaps 836. At least one edge 838 of each wall gap 836 may be beveled. When operatively assembled, the fixation members 814 are deployable through the wall gaps 836; the beveled edges 838 may promote smooth deployment of the fixation members 814 and prevent the fixation members 814 from hanging up or being caught in the wall gaps 836. Several slots 839 are formed in the housing 812 near the juncture of the peripheral support wall 822 and carriage support 824. The slots 839 receive tabs 846 on the cap 815 to lock the cap to the housing 812. Adjacent each slot 839 is a housing lip 841 formed along a portion of the peripheral wall 822.

Cap 815 may be annular, and may include an outer wall 50 generally opposite an inner wall 843. An outer surface 844 of the cap 815 may be positioned as an upper surface, and may include a plurality of steps, ridges and/or grooves which may facilitate gripping and manipulating the cap 815. The cap 815 may have circular outer and inner diameters, formed by the outer wall 850 and inner wall 843 respectively. The cap inner wall 843 includes a plurality of tabs 846 which project inferiorly from the inner wall 843, alternating with a plurality of gaps 847. Each tab 846 may include a cap lip 848 projecting from the tab. Tabs 846 and lips 848 may be semicircular to follow the outer shaped of the peripheral wall 822. The cap outer surface 844 may extend between cap inner wall 43 and cap outer wall 50 and form a track cover 852. A plurality of cap bosses 854 can project inwardly from the cap outer wall 850. Each cap boss 854 may include a ramp feature 856 which urges one of the fixation members 814 inward as it is deployed. The cap track cover 852 includes one or more cap grooves 857, which may be semicircular, and which guide the path of fixation members 814 as they are deployed and retracted. Housing 812 and cap 815 may be formed of plastic, or other materials listed herein.

Fixation carriage assembly 816 can include a substantially circular fixation carriage 860. Fixation member carriage 860 can have a first or superior side 874 and a second or inferior side 876. A plurality of mounting features 862 can project superiorly from the fixation carriage 860. Each mounting feature 862 may include a recess 864 through which an opening 866 is formed. Openings 866 can be sized to allow passage of a suture 90, but may also be small enough to retain a knotted suture, not permitting the knot to pass through the opening. A circular setback or groove 878 can be formed on the inferior side 876 similar to groove 78 of device 10, and be sized to receive a suture.

Figure 36A:
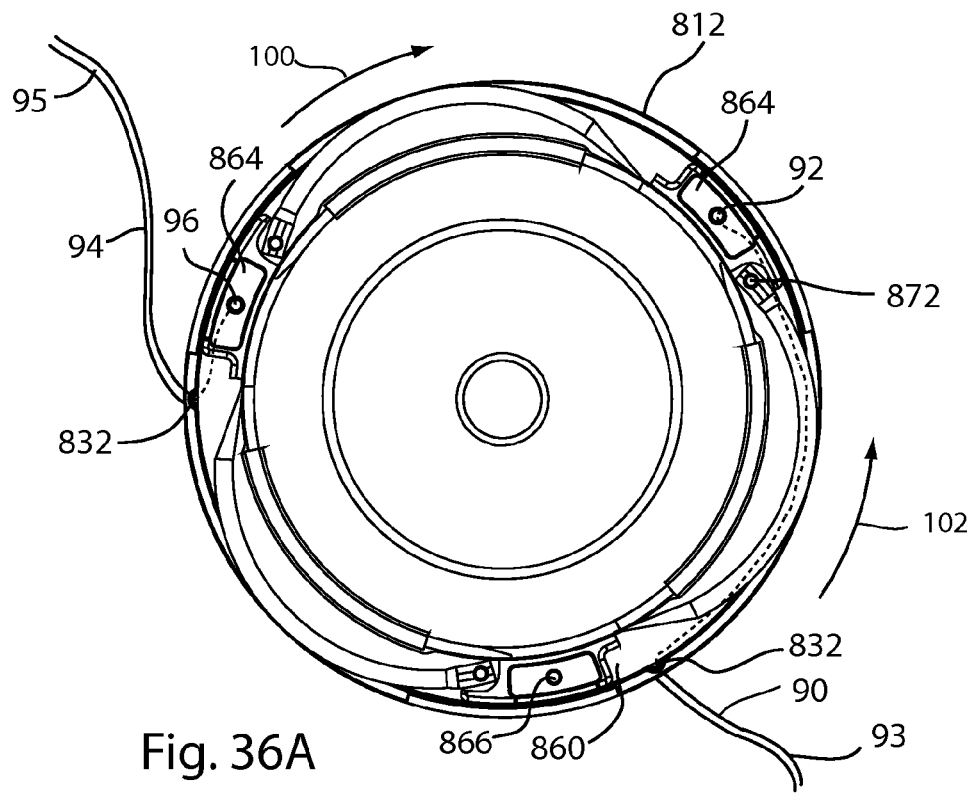
FIG. 36A is a superior view of a housing, carriage assembly and sutures of the device of FIG. 31A.

Each fixation member 814 can be curved, rigid, and may terminate at a beveled point. The rigid fixation members may be formed of stainless steel, or other materials disclosed herein. Other embodiments may include flexible fixation members, which may be straight or curved, and may be made of Nitinol, for example. The fixation member curvature may be non-concentric with the curvature of the carriage track 826, for example the fixation member curvature may have a smaller diameter than the diameter of the carriage track (FIG. 36A). Each fixation member 814 may include a base portion 880, a shaft 882, and a point 884, which may also be referred to as a tip. The point 884 may be sharpened and/or serrated in order to reduce the forces necessary to pierce the tissue, or deploy the fixation member. Any of the fixation members disclosed herein may also include a sharp tip or point for the same purpose. The fixation member may have an arch shape that lies substantially in a single plane in some examples; in other examples, the fixation member can be substantially straight. In yet further examples, the fixation member can have a curved shape in multiple planes or in an infinite number of planes. When assembled into the fixation member carriage assembly 816, a mounting pin 872 may pass through the fixation member base portion 880 and through carriage 860 to form a hinge type connection, about which the fixation member 814 may pivot.

Cap 815 may be operatively assembled to housing 812 by insertion of cap tabs 846 into housing slots 839. When the tabs 846 are fully inserted into the slots 839, each cap lip 848 may snap over and positively engage a housing lip 841 to lock the cap 815 to the housing 812. Fixation member carriage 816 and the attached fixation members 814 may be captured between the housing and the cap. In the example shown in FIG. 34, cap tabs 846 are exterior to housing peripheral wall 822. In another embodiment, the tabs 846 may be interior to the peripheral wall. Attachment of the cap 815 to the housing 812 encloses a fixation member retention space 888 bounded by fixation member carriage 816, track cover 852, housing inner wall 834 and cap outer wall 850. The mounting pins 872 project superiorly to the fixation carriage assembly 816 and are captured in the cap grooves 857.

A line passage or suture passage 886 may be formed between the groove 878 and outer rim 828. Suture 90 may be threaded through one opening 866, along suture passage 886 in the first direction 100 and through one aperture 832. A knot 92 may be formed in the suture end remaining at opening 866, the knot residing in recess 864 immediately adjacent opening 866, and the knot preventing withdrawal of the first suture through the opening 866. A free end 93 of suture 90 remains outside of the device 810. The second suture 94 may be threaded through a second opening 866, along suture passage 886 in the second direction 102 opposite the first direction, and through another aperture 832. The second suture 94 may also be knotted, forming knot 96 to prevent withdrawal. In another example, the first line 90 and/or second line 94 may be secured in one or more crimp tubes which reside in openings 866, the crimp tube(s) preventing withdrawal of the first and/or second suture through the corresponding opening 866. A free end 95 of suture 94 remains outside of the device 810. When the first and second sutures are thus placed, pulling on the first suture free end 93 will rotate the fixation member carriage assembly 816 in the first direction 100, and pulling on the second suture free end 95 will rotate the fixation member carriage assembly 816 in the second, or opposite, direction 102.

Figure 36B:
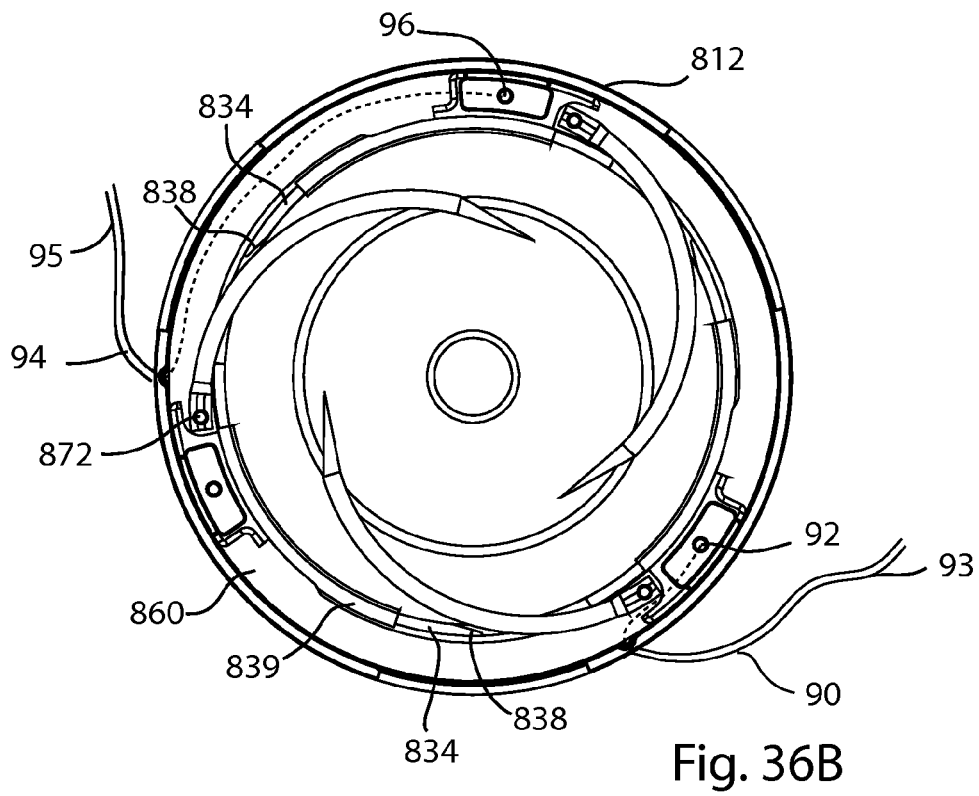
FIG. 36B is a superior view of the housing, carriage assembly and sutures in the deployed configuration of FIG. 32A; dashed lines indicate the approximate paths of the sutures in a passage between the carriage assembly and the housing.

With reference to FIGS. 36A and 36B, device 810 may be deployed in the same manner as device 10. The device may be place in the retracted configuration, with the fixation members 814 retracted into the fixation member retention space 888. Device 810 may be positioned so that tissue, for example cervical tissue, is received in housing inner space 833, with cap 815 and housing peripheral wall 822 enclosing the tissue. The free end 93 of suture 90 may then be pulled, rotating fixation member carriage assembly 816 in first direction 100. As the fixation member carriage assembly 816 rotates, the fixation member tips 884 will encounter the ramps 856 on the cap 815, and be deflected and forced inward through wall gaps 836 to protrude into the housing inner space 833, thus attaining the deployed configuration. Pins 872 translate in grooves 857, further guiding the fixation member deployment. The deployment paths of fixation members 814 may be coplanar in some embodiments, and the fixation members 814 may be deployed along a plane perpendicular to the lengthwise central axis 35 of the housing 812. The plane may also be described as transverse to the lengthwise central axis 35. The plane may also be coplanar with or parallel to the planar surface which is completely enclosed by the housing. The fixation members 814 may pierce and grip the tissue captured in the housing inner space 833. As described for device 10, this can advantageously result in fixing the position of the tissue within the housing 812, and preventing the tissue from subsequently translating relative to the device 810 along the lengthwise central axis. A stylus, tubular member, rod, or other elongated member (not shown) may be inserted into device 810 through housing opening 823 and pass through the tissue, and may pass out of device 810 through cap 815, leaving a free end of the elongated member exterior to the housing end 820. For example, an elongated tubular member may pass through housing opening 823 and into a cervix captured in housing inner space 833. The elongated tubular member free end may be manipulated to move the device 810 and the tissue gripped within. Instruments, bodily tissues, or fluids may be passed through the elongated tubular member into or out of the tissue. When desired, free end 95 of suture 94 may be pulled to rotate the fixation member assembly 816 in the second direction 102 and withdrawing the fixation members 814 from the tissue and back into the retracted configuration.

FIGS. 37-60 disclose embodiments of fixation members, fixation member carriages and carriage assemblies which may be used in tissue fixation devices 10, 110, 210, 310, 410, 510, 610, 710, 810 or other tissue fixation devices. For example, a fixation member carriage and the fixation members carried thereon can be substituted for fixation member assembly 816 in device 810, or substituted for fixation member assembly 16 in device 10. In each example, the fixation member(s) are deployable between a retracted configuration in which they are retracted and the tissue fixation device may be positioned relative to tissue to be captured, and a deployed configuration in which the fixation members are deployed to contact and capture the tissue, and subsequent movement of the device will move or manipulate the captured tissue. The fixation members may be needles. It is understood that each fixation member disclosed herein may have a sharp tip for piercing and/or engaging tissue such as cervical tissue. Each fixation member disclosed herein may be curved. The fixation members disclosed herein may be stamped, formed from round stock, formed from rod stock, or manufactured from materials and methods known in the art for making needles.

Figures 37A, 37B:
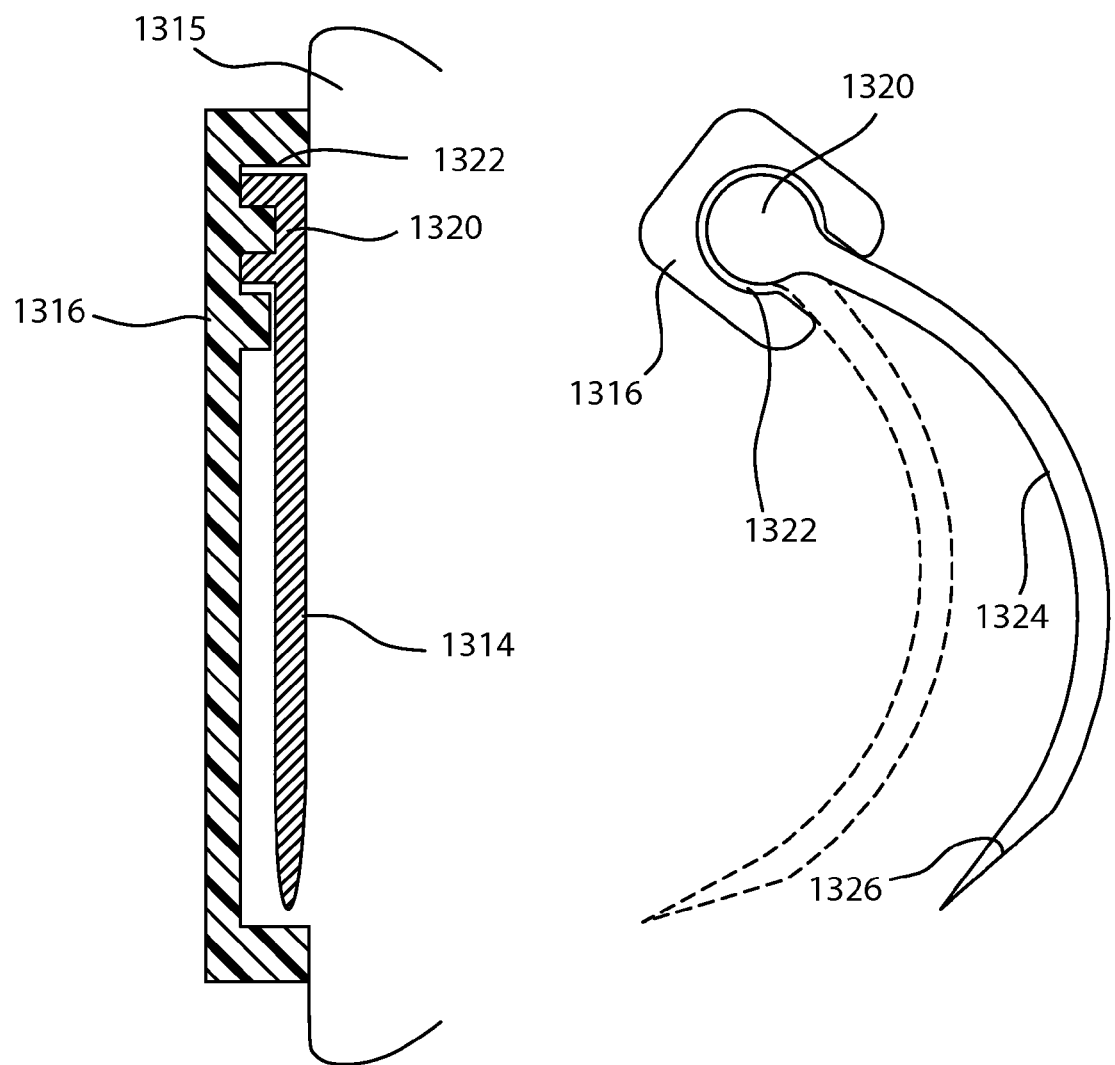
FIG. 37A is a top-down view of a fixation member captured in a fixation member carriage.
FIG. 37B is a partial side cross sectional view of the fixation member carriage and fixation member of FIG. 37A and the cap of FIG. 31A.

FIGS. 37A and 37B show a fixation member or needle 1314 mounted in a carriage 1316. A cap 1315 can capture needle 1314 in carriage 1316. Fixation member 1314 includes a convex attachment feature 1320 shaped as a portion of a circle, which is received in a concave capture feature 1322 to form a ball joint. The ball joint allows polyaxial movement of the fixation member 1314. Fixation member 1314 has a sharp tip 1326.

Figure 38A:
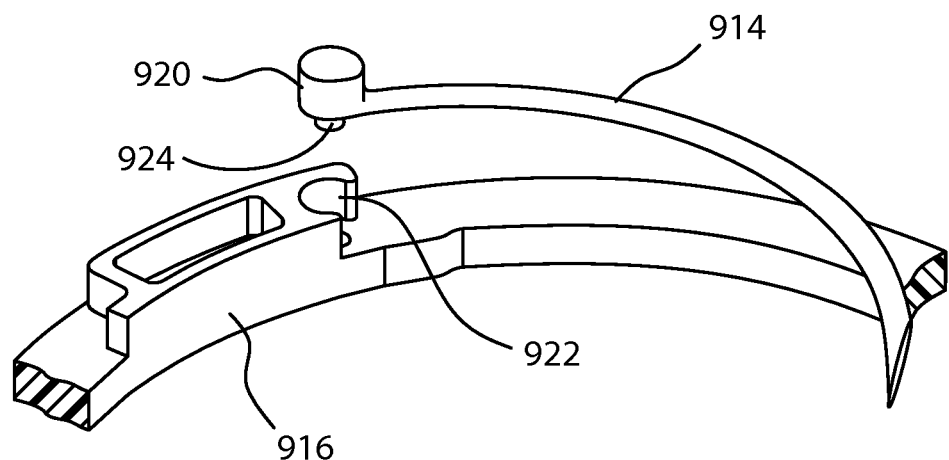
FIG. 38A is a perspective partial view of a fixation member carriage with a capture feature.
Figure 38B:
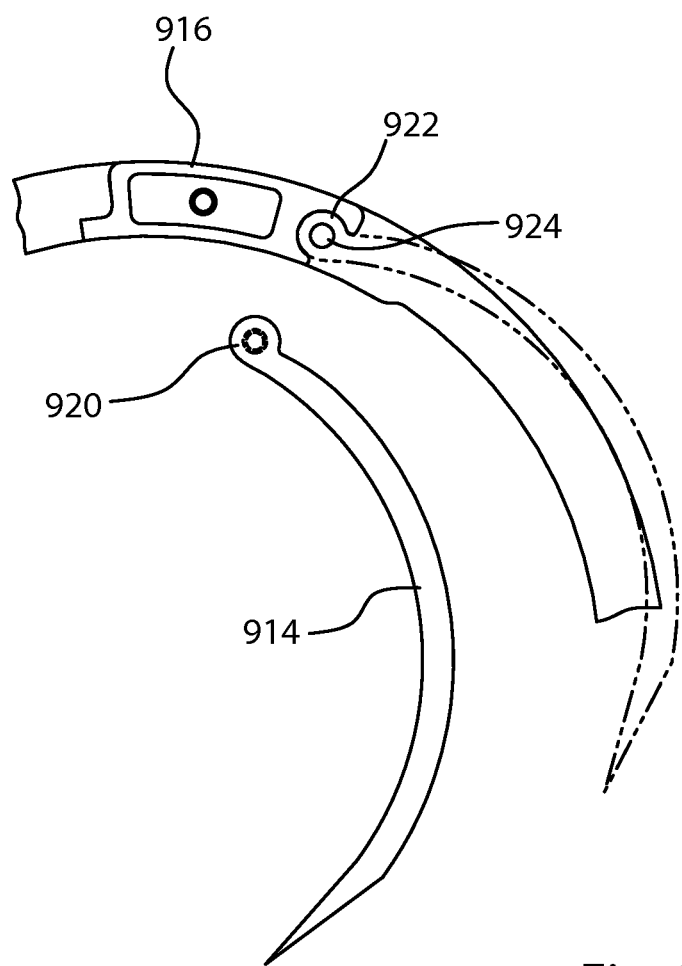
FIG. 38B is an exploded view of the fixation member and the fixation member carriage of FIG. 38A.

FIGS. 38A and 38B show a fixation member or needle 914 mounted in a carriage 916. An attachment feature 920 on the needle 914 is shaped as a cylinder. A pin 924 within a capture feature 922 on carriage 916 receives the needle 914. When captured as shown, needle 914 can rotate about a single axis. Pin 924 may be molded into carriage 916. In other embodiments, pin 924 and other pins disclosed herein may be molded, press fit, glued, or welded.

Figure 39:
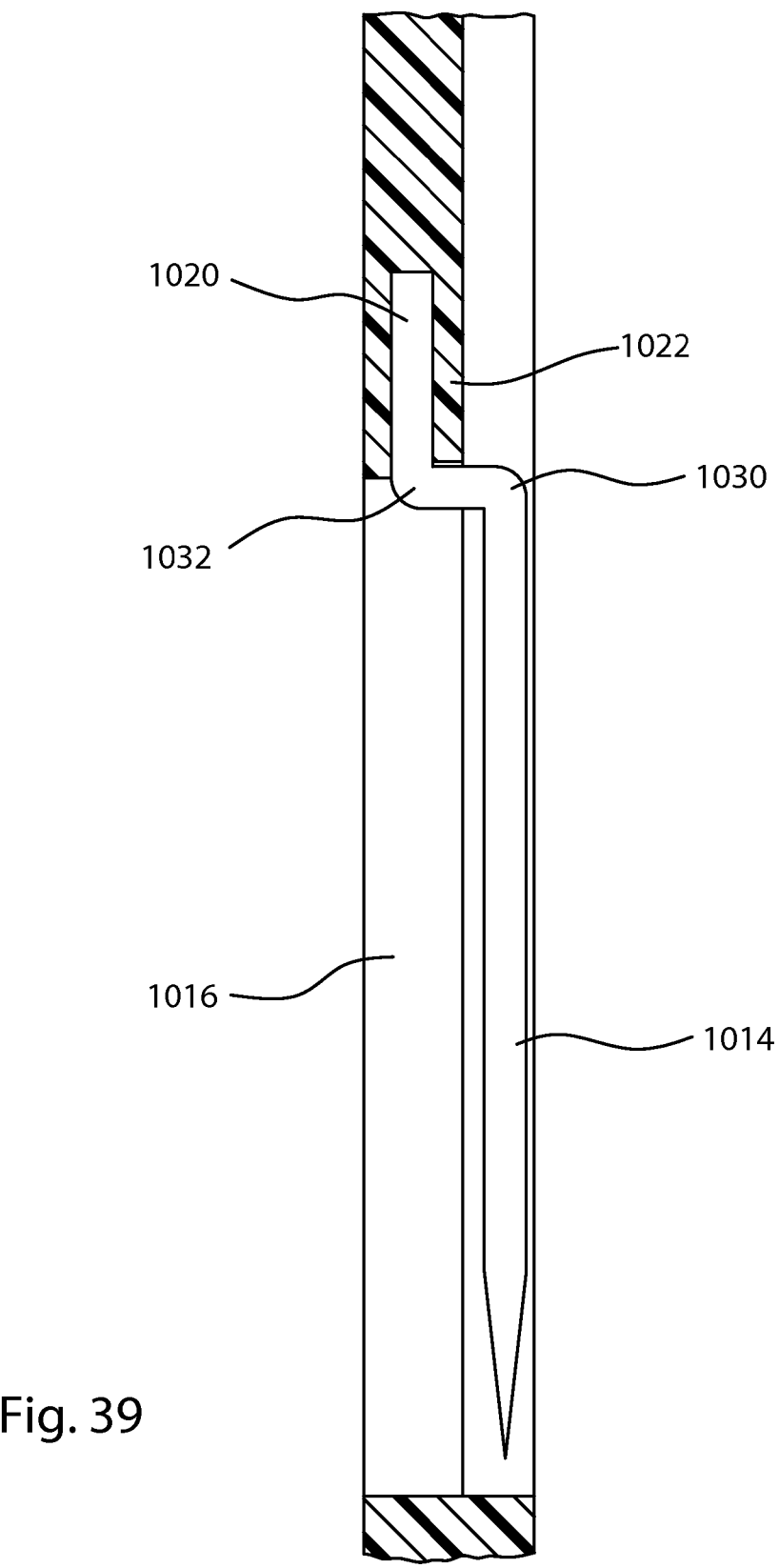
FIG. 39 is a side partial cross sectional view of a fixation member captured in a fixation member carriage.

FIG. 39 shows a needle 1014 mounted on a carriage 1016 in a capture feature 1022. The needle 1014 is pre-formed with bends 1030, 1032 and attachment feature 1020 folded into the needle. As carriage 1016 is rotated, attachment feature 1020 swings to allow the needle to deploy and retract. A cap (not shown) may hold needle 1014 in capture feature 1022.

Figure 40A:
FIG. 40A is a side view of a needle, the needle curving into the page.
Figure 40B:
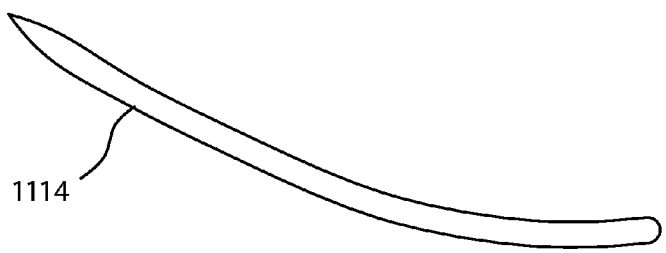
FIG. 40B is a top view of the needle of FIG. 40A.
Figure 40C:
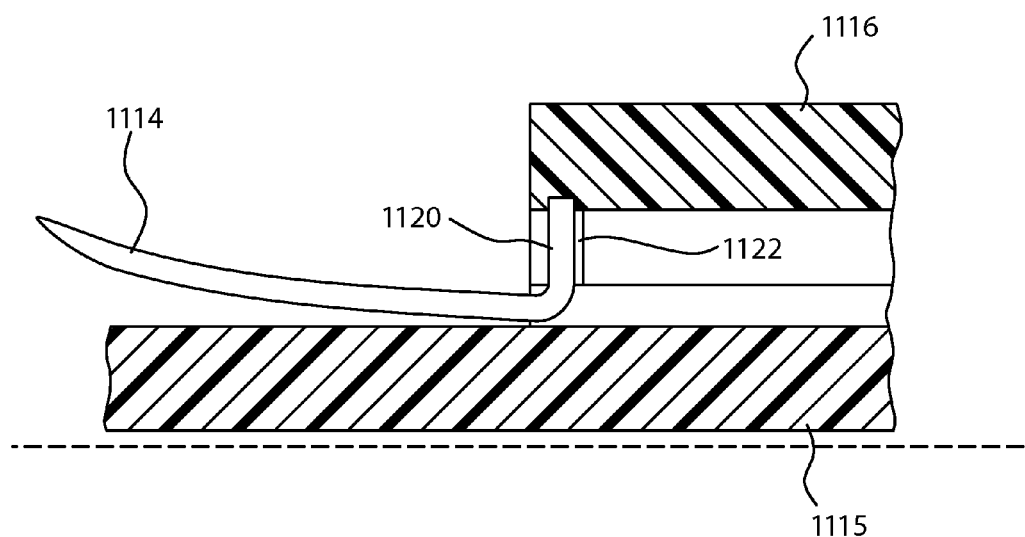
FIG. 40C is a side cross-sectional view of the needle of FIG. 40A captured in a needle carriage.

FIGS. 40A-40C show a needle 1114, cap 1115 and carriage 1116. In FIG. 40C, the needle 1114 is captured in between the cap 1115 and carriage 1116. The needle 1114 includes an attachment feature 1120 wherein the needle end is bent approximately 90° to allow capture in a capture feature 1122. When captured, needle 1114 can rotate about at least one axis. Needle 1114 may be formed from stainless steel round stock, and sharpened.

Figure 41:
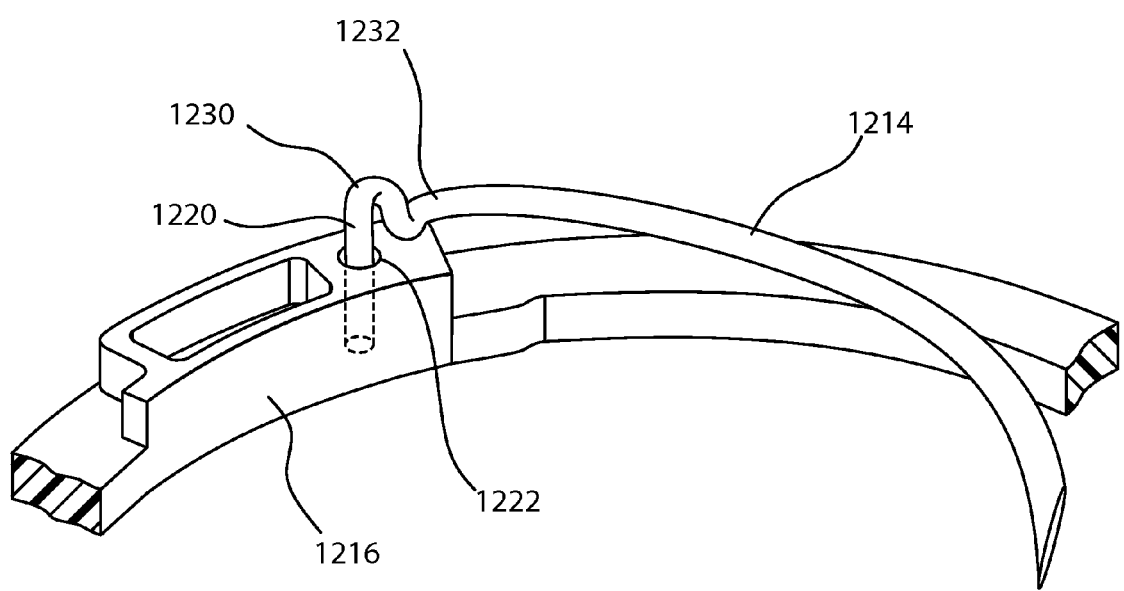
FIG. 41 is a partial perspective view of a needle captured in a needle carriage.
Figure 42A:
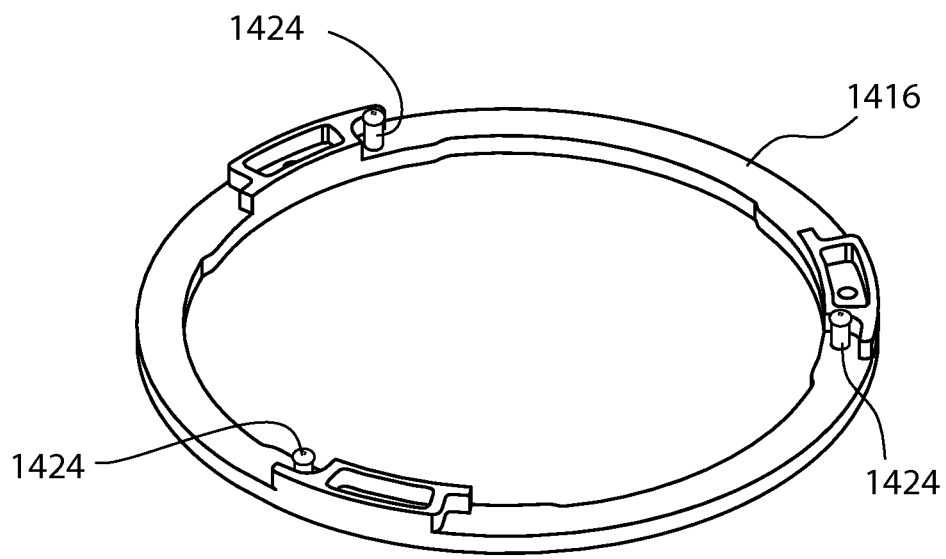
FIG. 42A is a perspective view of a needle carriage having several pins.
Figure 42B:
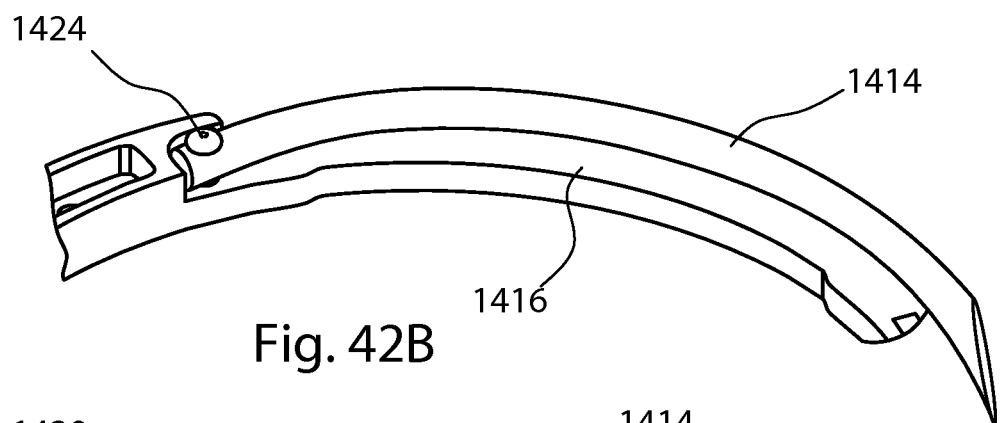
FIG. 42B is a partial view of a needle mounted to the carriage of FIG. 42A.
Figure 42C:
FIG. 42C is a top view of the needle of FIG. 42B.
Figure 42D:
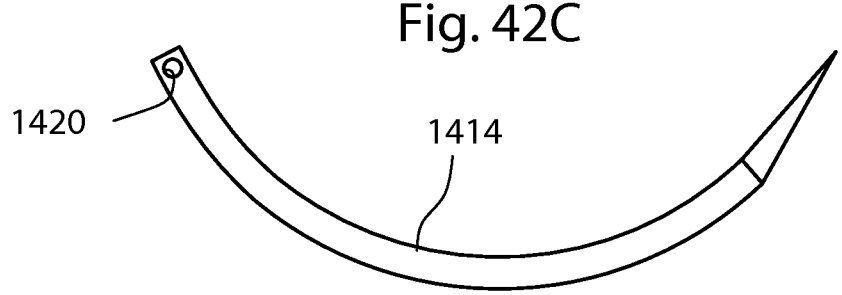
FIG. 42D is a side view of the needle of FIG. 42B.

FIG. 41 shows a needle 1214 mounted on a carriage 1216 in a capture feature 1222. The needle 1214 is pre-formed with bends 1230, 1232 and attachment feature 1220 folded into the needle. As carriage 1216 is rotated, attachment feature 1220 swings within capture feature 1222 to allow the needle to deploy and retract. A cap (not shown) may hold needle 1214 in capture feature 1222.

FIGS. 42A-42D show a metal carriage 1416 with pins 1424 press fit or welded to the carriage. One or more needles 1414 include an attachment feature 1420 which is a hole shaped to receive pin 1424. One end of pin 1424 may be deformed to retain the needle. The metal carriage 1416 may be stamped or machined.

Figure 43A:
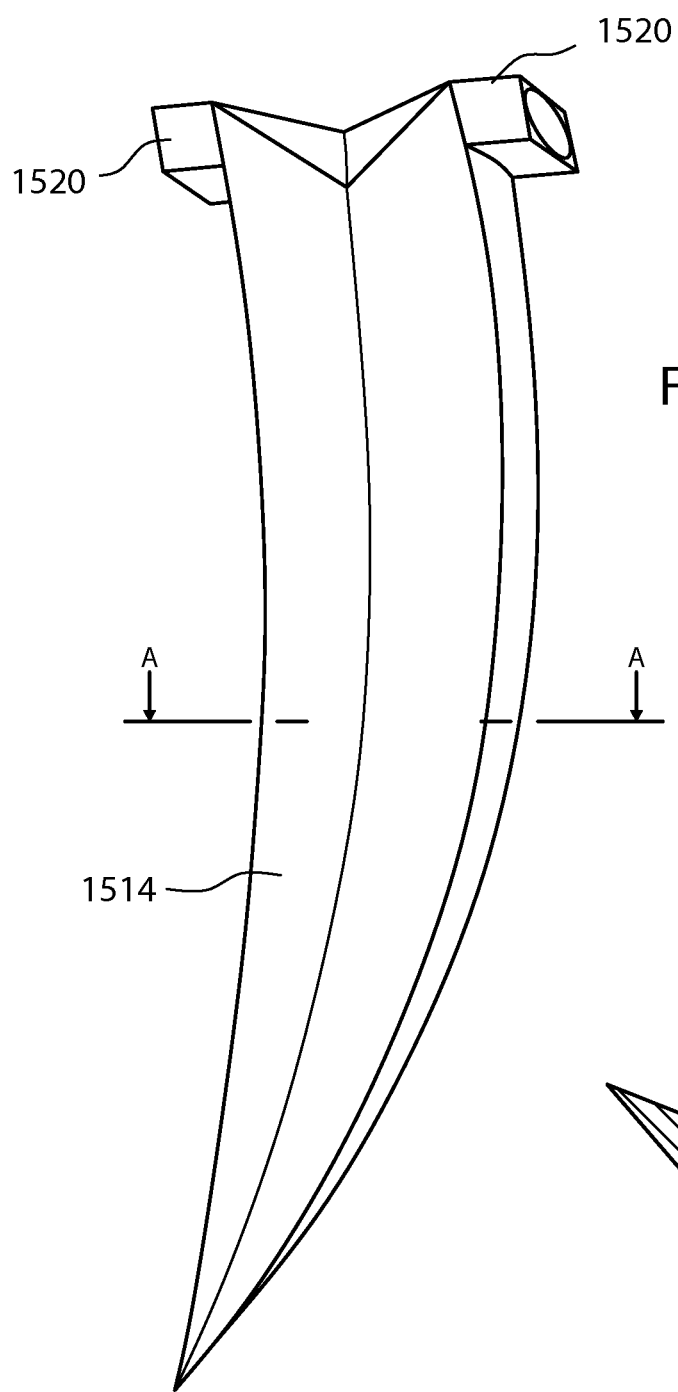
FIG. 43A is a side view of a needle.
Figure 43B:
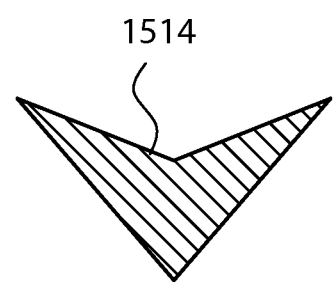
FIG. 43B is a transverse cross section of the needle of FIG. 43A taken along line A-A

FIGS. 43A and 43B show a needle 1514 which may be created by stamping out of flat stock. The needle 1514 may then be bent or folded to create the V-shape seen in the cross-section of FIG. 20B. The needle 1520 may include one or more attachment features 1520, which may be shaped as pegs or posts, to attach to a carriage and/or cap as disclosed elsewhere herein. The needle 1514 may be described as a stylet.

Figure 44:
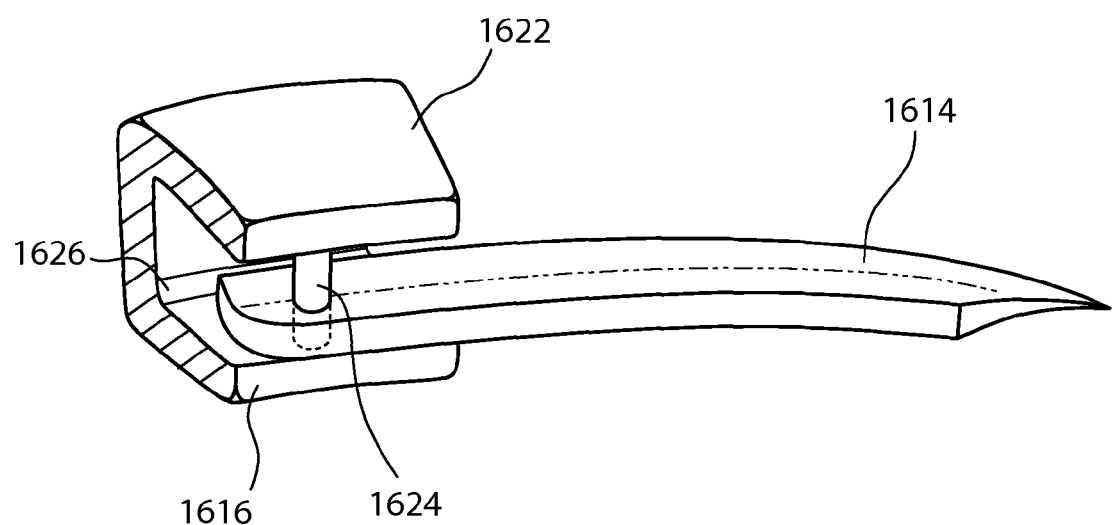
FIG. 44 is a partial side view of a needle captured in a carriage.

FIG. 44 shows a needle 1614 mounted on a carriage 1616. Carriage 1616 includes a capture feature 1622 formed as a tab which extends over the carriage 1616 to capture a pin 1624. Needle 1614 includes an attachment feature shaped to receive the pin 1624 so that when mounted, the needle 1614 is captured on the pin 1624, between the carriage 1616 and the capture feature 1622. In an embodiment formed from steel, capture feature 1622 may be connected to the carriage 1616 at a hinge 1626. In an embodiment formed from plastic, capture feature 1624 may be folded over and/or formed around a mold, and welded to carriage 1616. Needle 1614 may be a stylet, sharing the same features as needle 1514.

Figure 45A:
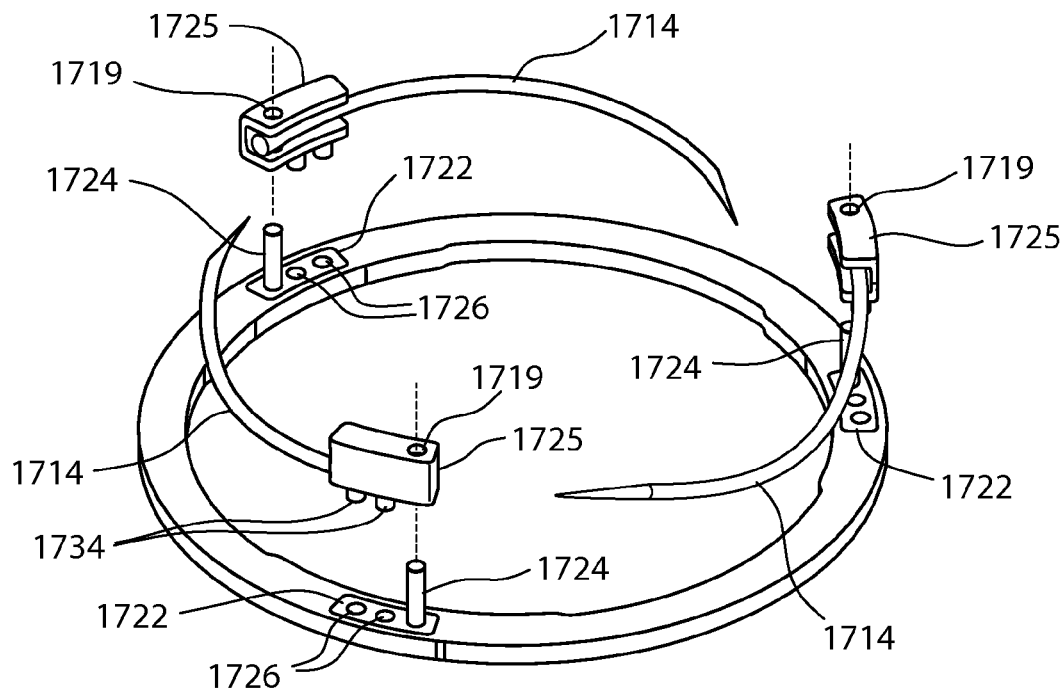
FIG. 45A is a top view of a carriage with a plurality of needles and capture features.
Figure 45B:
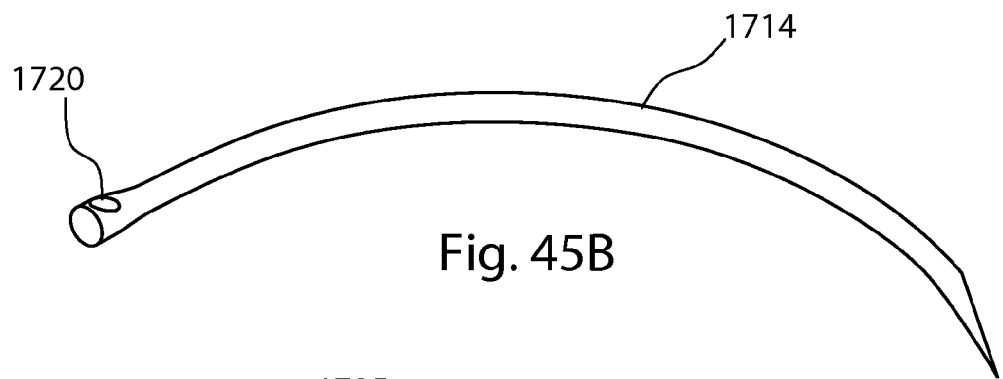
FIG. 45B is a top view of a needle of FIG. 45A.
Figure 45C:
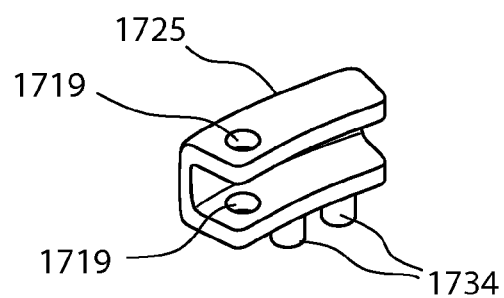
FIG. 45C is a perspective view of a retention block.

FIGS. 45A-45C show a carriage 1716 with capture features 1722 and a needle 1714 having a hole 1720. A cap is not shown, but includes a number of retention blocks 1725 equal to the number of capture features 1722 on the carriage 1716. Each capture feature 1722 includes a pin 1724 and two holes 1726. Each retention block 1725 includes two pins 1734 and one hole 1717, plus a bore 1719. When assembled, needle 1714 is captured between carriage 1716 and cap 1715, with pin 1724 extending from carriage 1716 through needle hole 1720 and bore 1719. Retention block pins 1724 extend into holes 1726. In another embodiment, the retention block 1725 may be part of the carriage 1716 instead of the cap 1715.

Figure 46A:
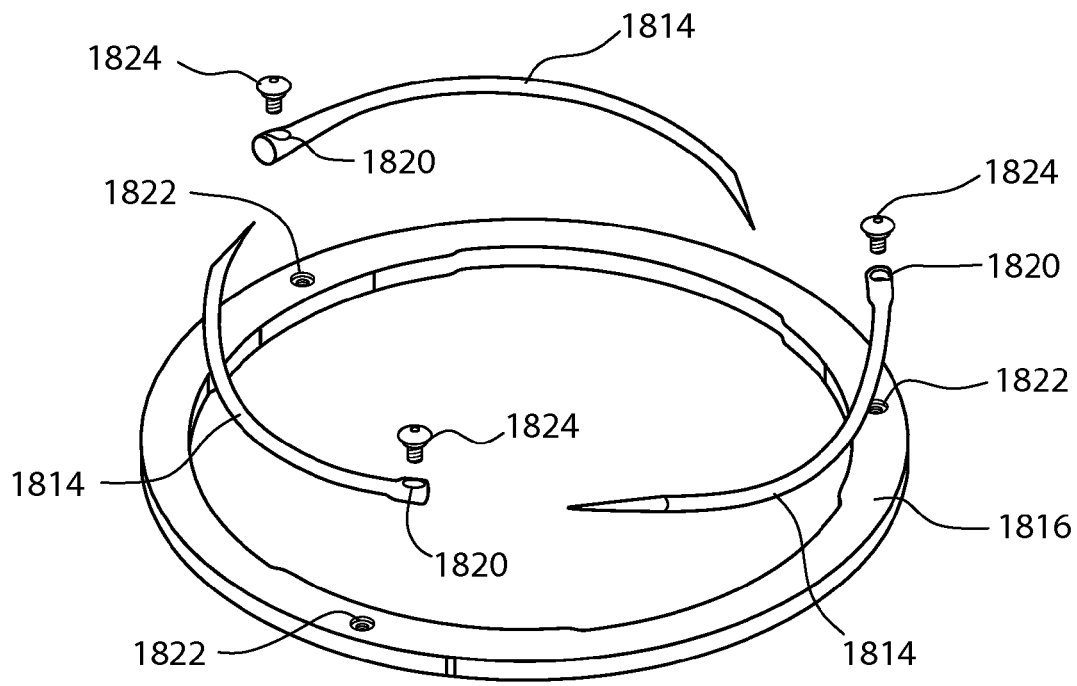
FIG. 46A is a perspective exploded view of a needle carriage assembly.
Figure 46B:
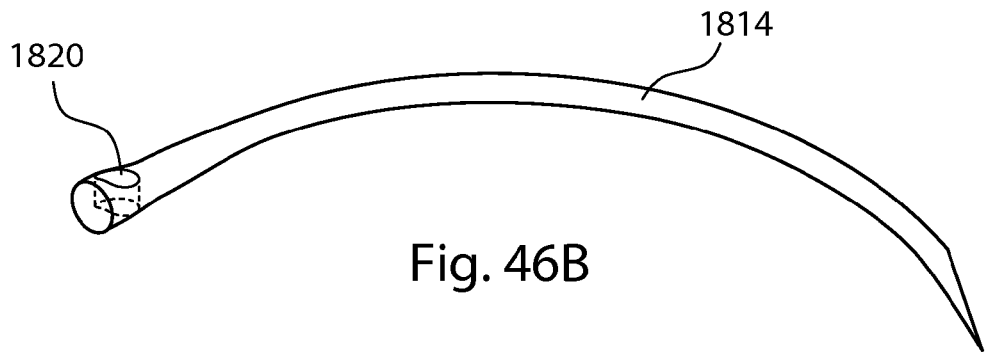
FIG. 46B is a top view of the needle of FIG. 46A.
Figure 46C:
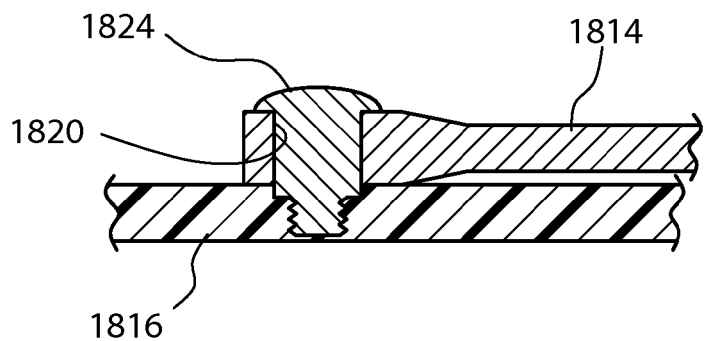
FIG. 46C is a partial side cross-sectional view of the needle carriage assembly of FIG. 46A.

FIGS. 46A-46C show an embodiment including a stamped carriage 1816, a needle 1814 and a pin 1824. Pin 1824 includes a head 1826 and a shoulder 1828. Needle 1814 includes an attachment feature which is a hole 1820. Pin 1824 may be received in hole 1820 to mount needle 1814 to carriage 1816; head 1826 retains the needle 1814 on the pin 1824. The carriage 1816 include capture features 1822 which may be holes to receive pins 1824.

Figure 47A:
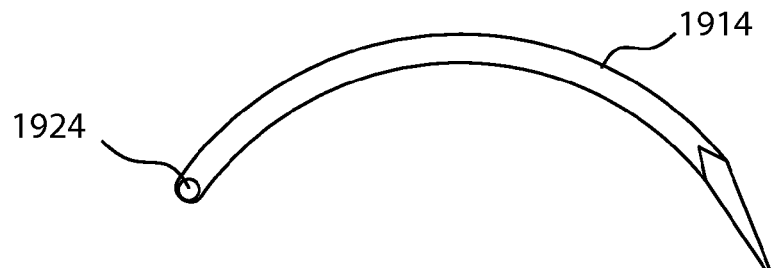
FIG. 47A is a top view of a needle.
Figure 47B:
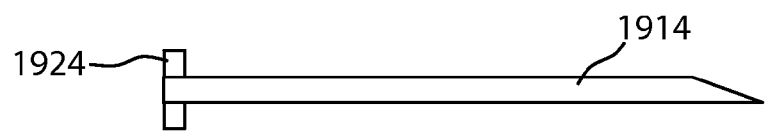
FIG. 47B is a side view of the needle of FIG. 47A.
Figure 47C:
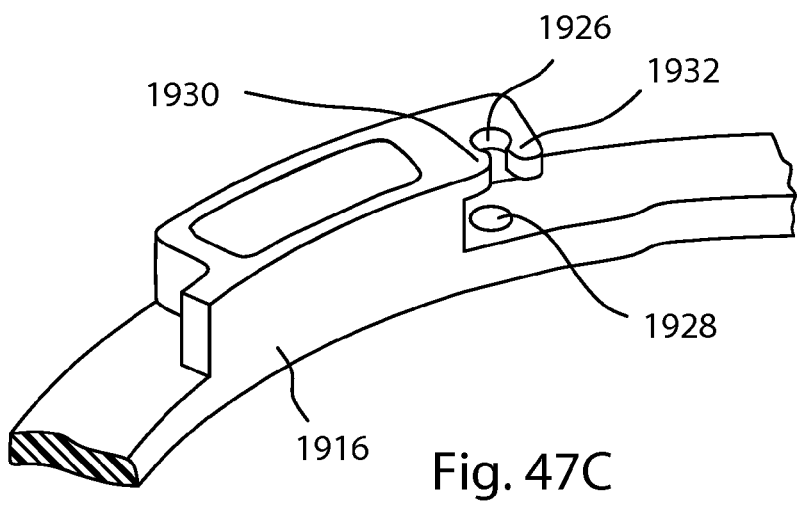
FIG. 47C is a perspective view of a needle carriage having a capture feature.
Figure 47D:
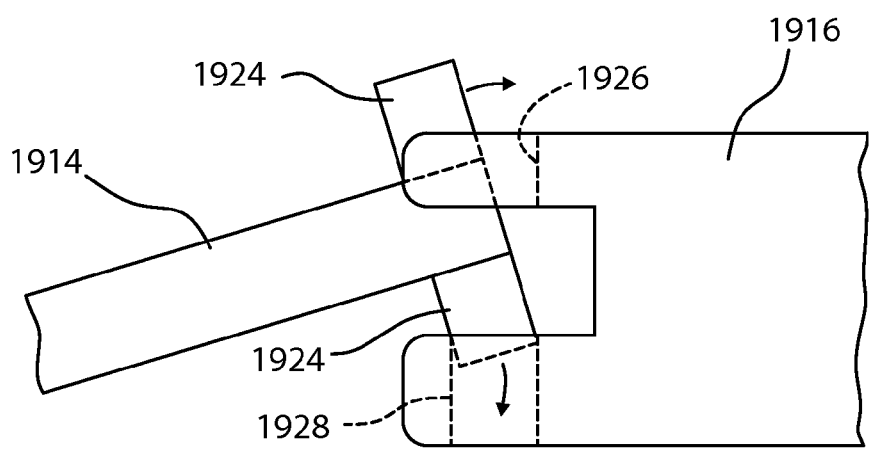
FIG. 47D is a partial view of the needle of 47A mounted to the carriage of FIG. 47C by a pin.
Figure 48A:
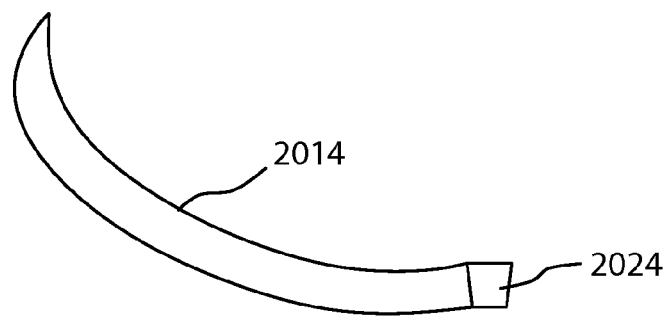
FIGS. 48A, 48B and 48C are various views of a needle.
Figure 48B:
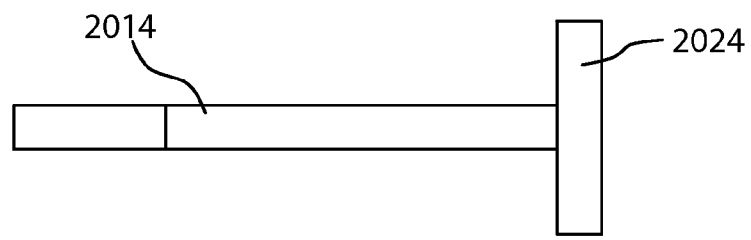
Figure 48C:
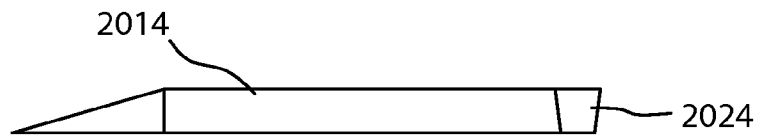
Figure 48D:
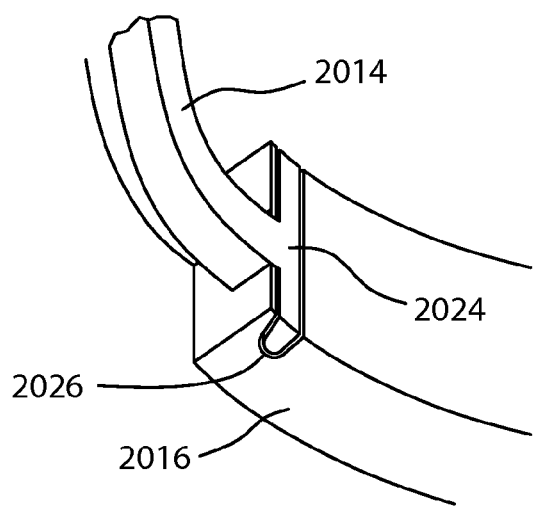
FIG. 48D is a perspective view of the needle of FIG. 48A-48C captured in a carriage.

FIGS. 47A-47C show an embodiment including a carriage 1916 and a needle 1914, the needle having an attachment features which is a pin 1924. A capture feature 1922 on the carriage 1916 includes a slot 1926 and a hole 1928. The needle can be snapped or rocked into the capture feature 1922, with pin 1924 moving through slot 1926 into hole 1928. The edges 1930, 1932 of the slot 1926 may deform slightly as the pin 1924 is pushed in, then act as interference to keep the pin 1924 in place in the capture feature.

FIGS. 48A-48D shows an embodiment similar to FIGS. 47A-47C. A needle 2014 includes a pin 2024 for attachment. Carriage 2016 includes a capture feature 2022 having a slot 2026. The pin 2024 is captured in the slot 2026 as shown. Not shown, a cap 2015 includes an inner wall 2017 which holds the pin 2024 in the slot 2026.

FIGS. 49A and 49B show an embodiment similar to FIGS. 43A and 43B. Needle 2114 includes an attachment feature 2120. A separate pin 2124 can attach the needle to a carriage. Needle 2114 may be formed in the same way as described for needle 1514.

Figure 50:
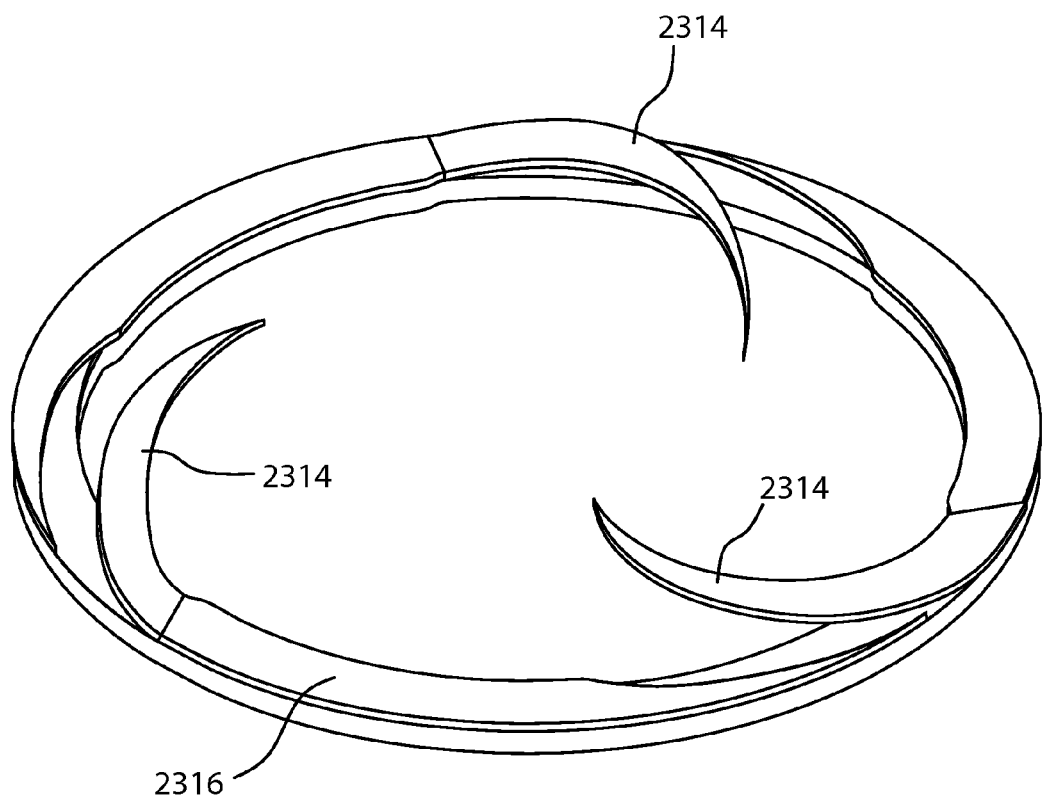
FIG. 50 is a perspective view of another carriage and needles stamped from a single piece of material.

FIG. 50 shows another carriage and needle assembly stamped from a single piece of stock. The assembly includes carriage 2316 and needles 2314. The stock metal may be stamped, then the needles bent and sharpened. The needles 2314 project upward from carriage 2316.

Figure 51:
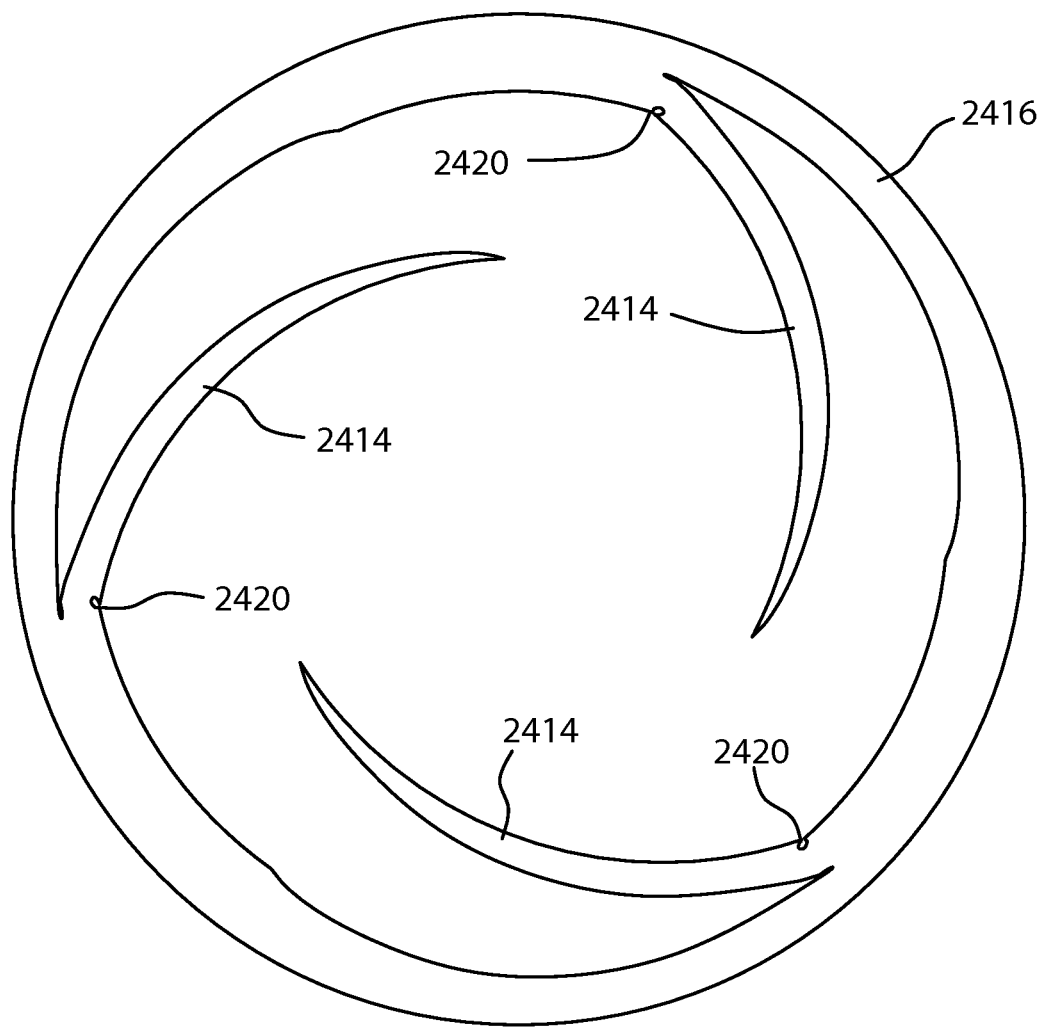
FIG. 51 is a perspective view of another carriage and needles stamped from a single piece of material.

FIG. 51 shows another carriage and needle assembly stamped from a single piece of stock. The assembly includes carriage 2416 and needles 2414. The stock metal may be stamped, then the needles bent and sharpened. The needles 2414 project inward from carriage 2416. A hinge 2420 is formed where each needle 2414 projects from carriage 2416; each hinge 2420 may be formed by cutting away portions of the material between the needle and the carriage. The hinge 2420 may be described as a living hinge. In FIGS. 50-51, the needles bend out of the plane of the carriage.

Figure 52:
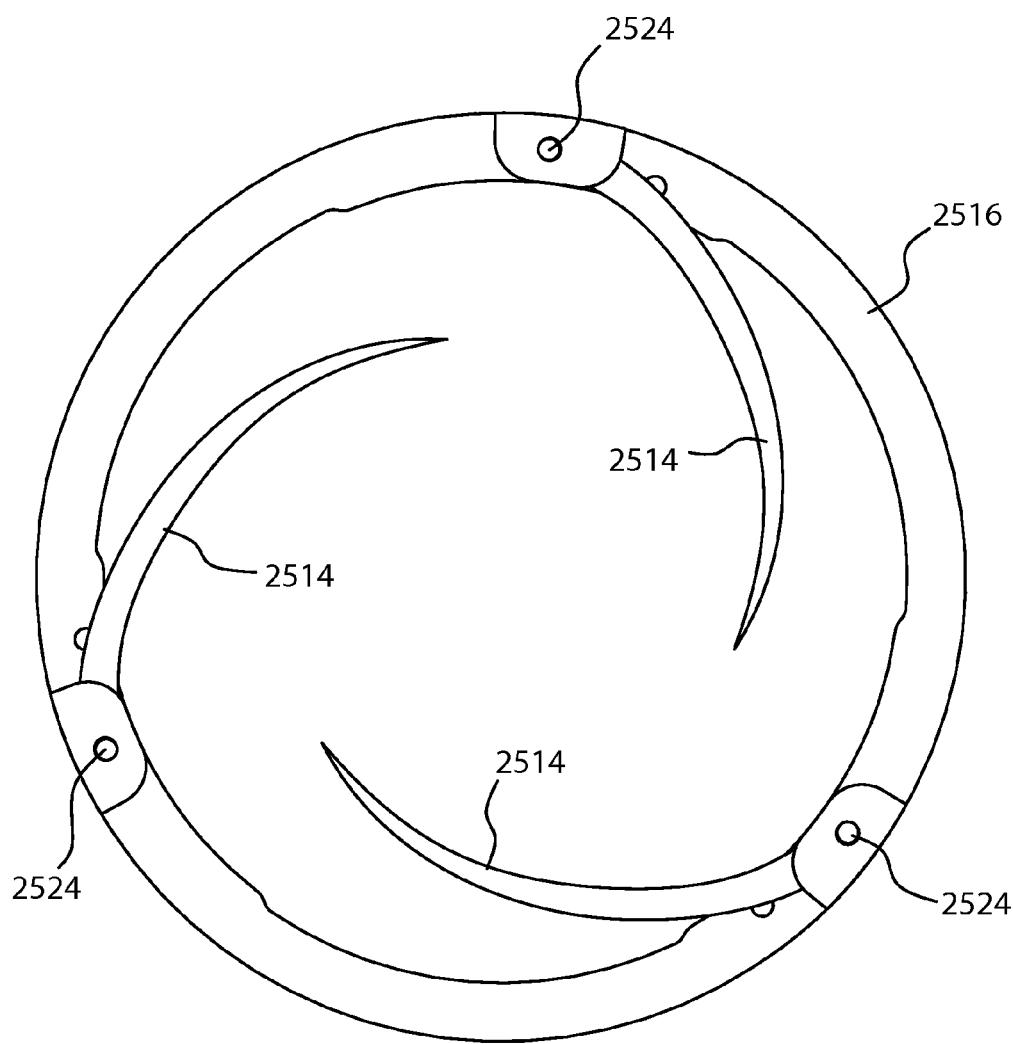
FIG. 52 is a top view of a carriage with several needles overmolded into the carriage.

FIG. 52 shows an embodiment of a carriage assembly including a carriage 2516 and needles 2514. The carriage is formed from molded material such as polymer. Pins 2524 attach the needles to the carriage. In this embodiment, the pins 2524 and needles 2514 are in place when the carriage 2516 is molded; the pins and needles are over-molded into the carriage assembly.

Figure 53:
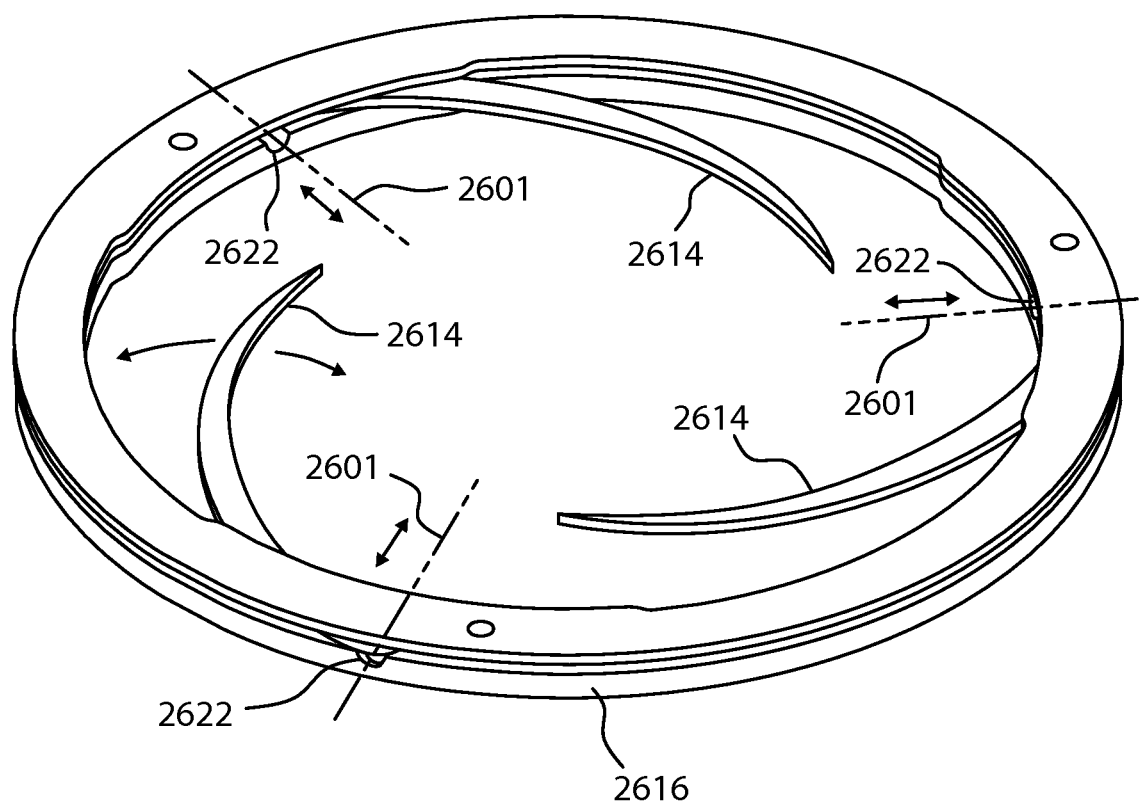
FIG. 53 is a perspective view of a carriage with needles mounted in slots in the carriage.

FIG. 53 shows an embodiment of a carriage assembly including a carriage 2616 and a needle 2614. When deployed, needle 2614 slides in a slot 2622 on carriage 2616 along axis 2601.

Figure 54:
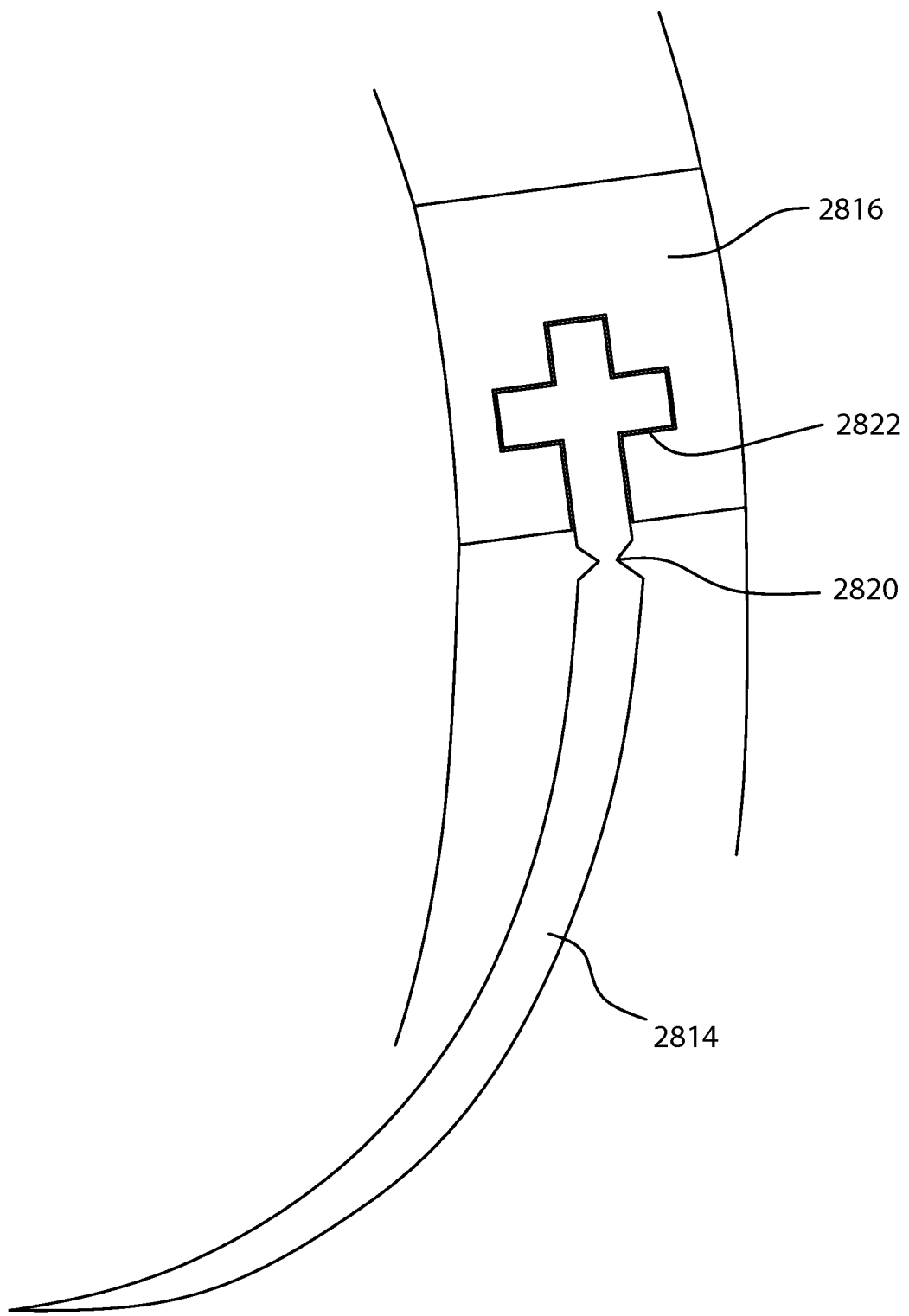
FIG. 54 is a top view of a flexible needle captured in a carriage.

FIG. 54 shows another carriage and needle assembly including carriage 2816 and needles 2814. The needles may be formed from flexible steel, and may be insert molded into the carriage. A hinge 2820 is formed where each needle 2814 projects from carriage 2816 at capture feature 2822; each hinge 2820 may be formed by cutting away portions of the needle. The hinge 2820 may be described as a living hinge, and may result in a springy needle. Capture feature 2822 may be rigid.

Figure 55:
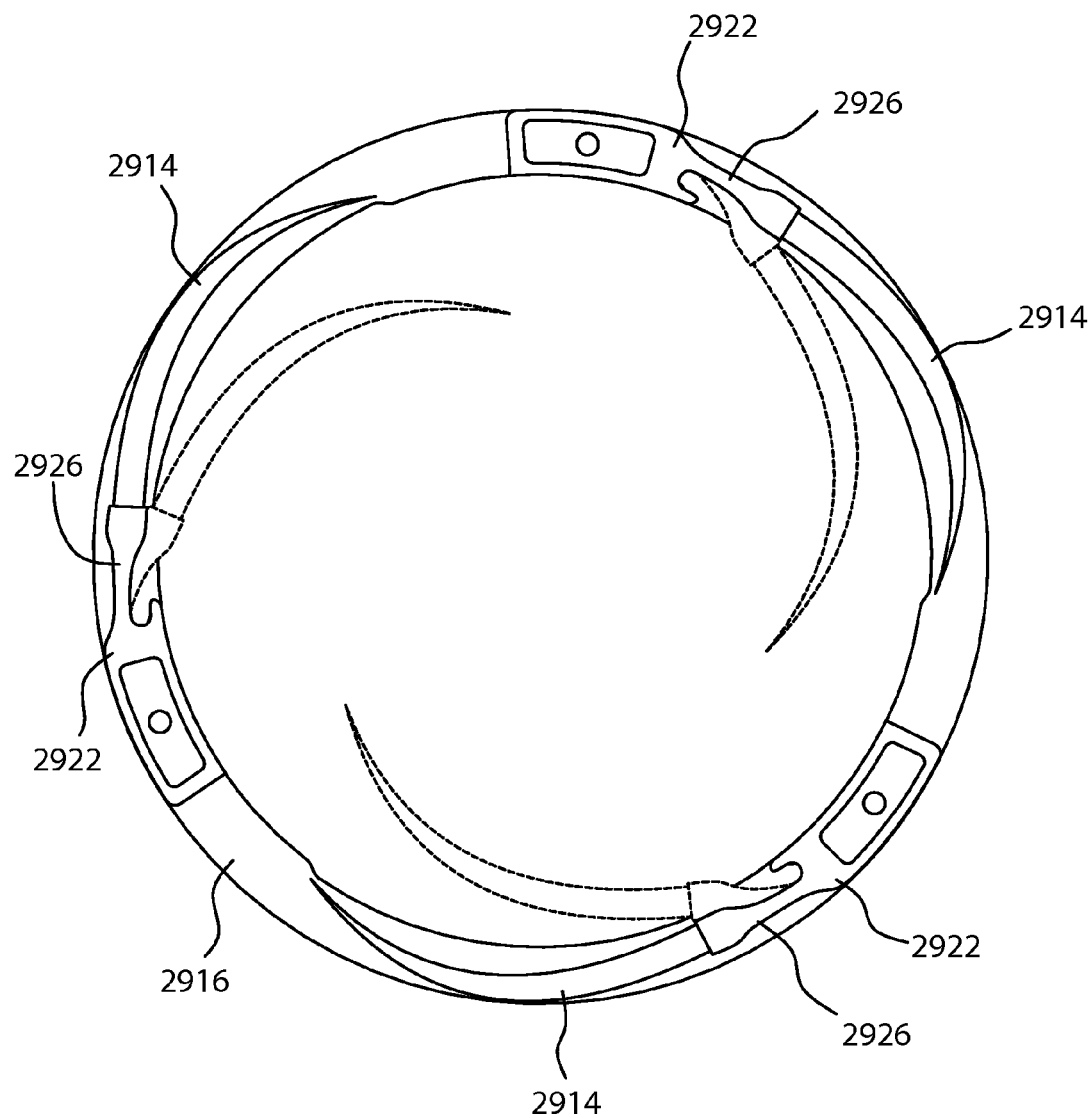
FIG. 55 is a top view of a needle carriage with needles overmolded into the carriage, hinges formed between the needles and the carriage.

FIG. 55 shows another carriage and needle assembly including carriage 2916 and needle 2914. Carriage 2916 include capture feature 2922 having a living hinge 2926. Needle 2914 is attached to the capture feature 2922 through overmolding; the needle is overmolded directly into the carriage.

Figure 56:
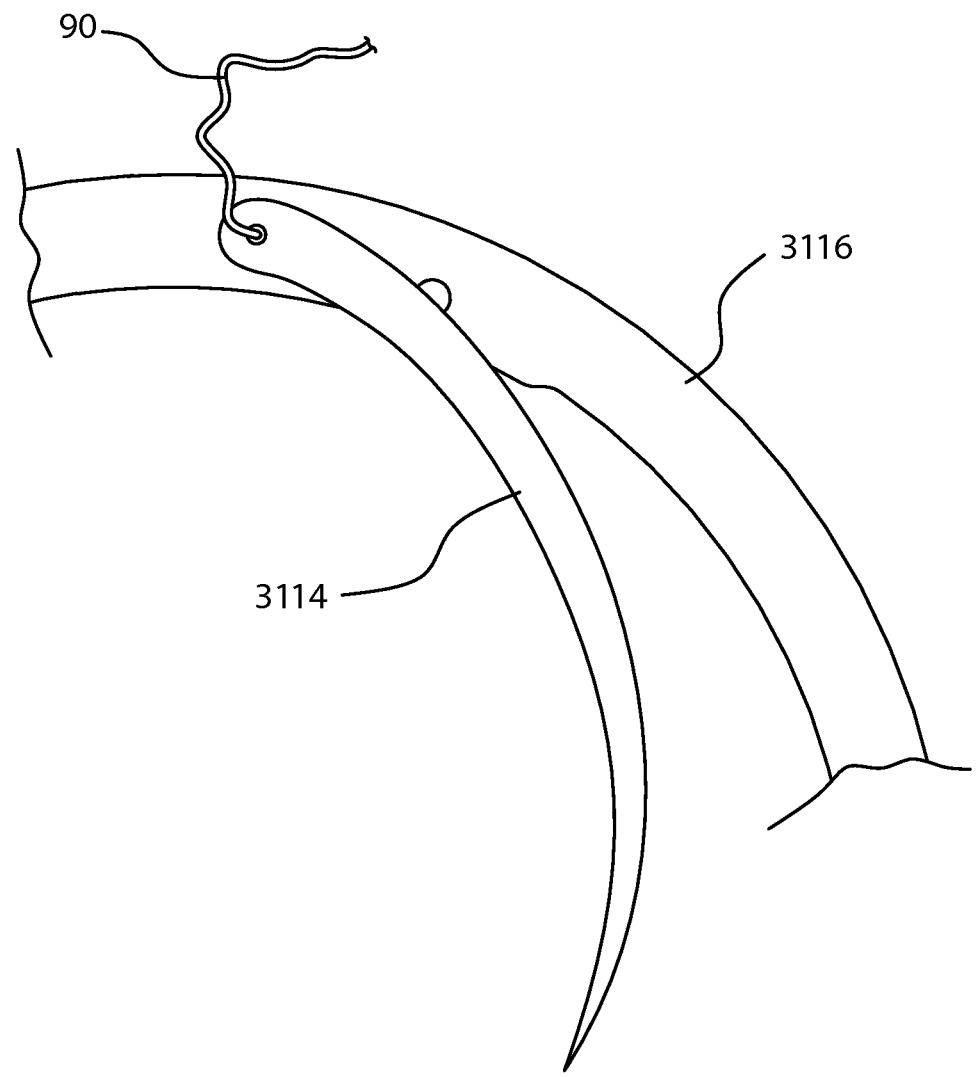
FIG. 56 is a partial top view of a carriage, a needle, and suture for deploying the needle.

FIG. 56 shows another carriage and needle assembly including carriage 3116 and at least one needle 3114. A suture 90 is attached to the needle and can be manipulated to activate the needle. In this embodiment, the carriage 3116 does not move within a housing such as housing 3012, but instead the needles 3114 are deployed by one or more sutures.

Figure 57:
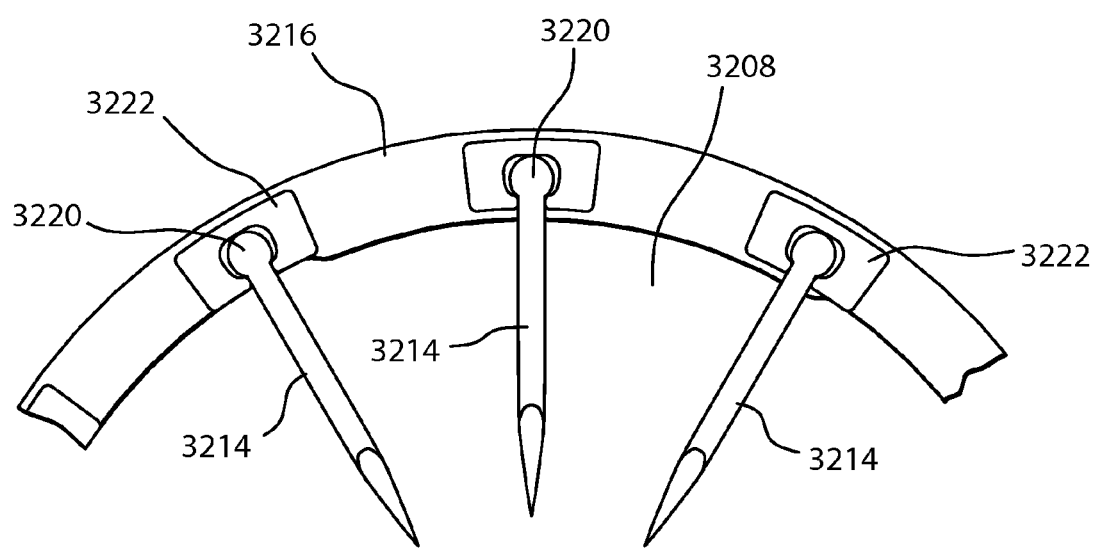
FIG. 57 is a partial top view of a carriage and a plurality of straight needles.

FIG. 57 shows another carriage and needle assembly including carriage 3216 and a plurality of needles 3214. Carriage 3222 includes a plurality of capture features 3222, and each needle includes an attachment feature 3220 which may be received in a capture feature. Unlike other embodiments herein, needles 3214 are straight. When deployed, the needles rotate approximately 90° and project straight into a center opening 3208 of the carriage 3216. When retracted, the needles may point up.

Figure 58:
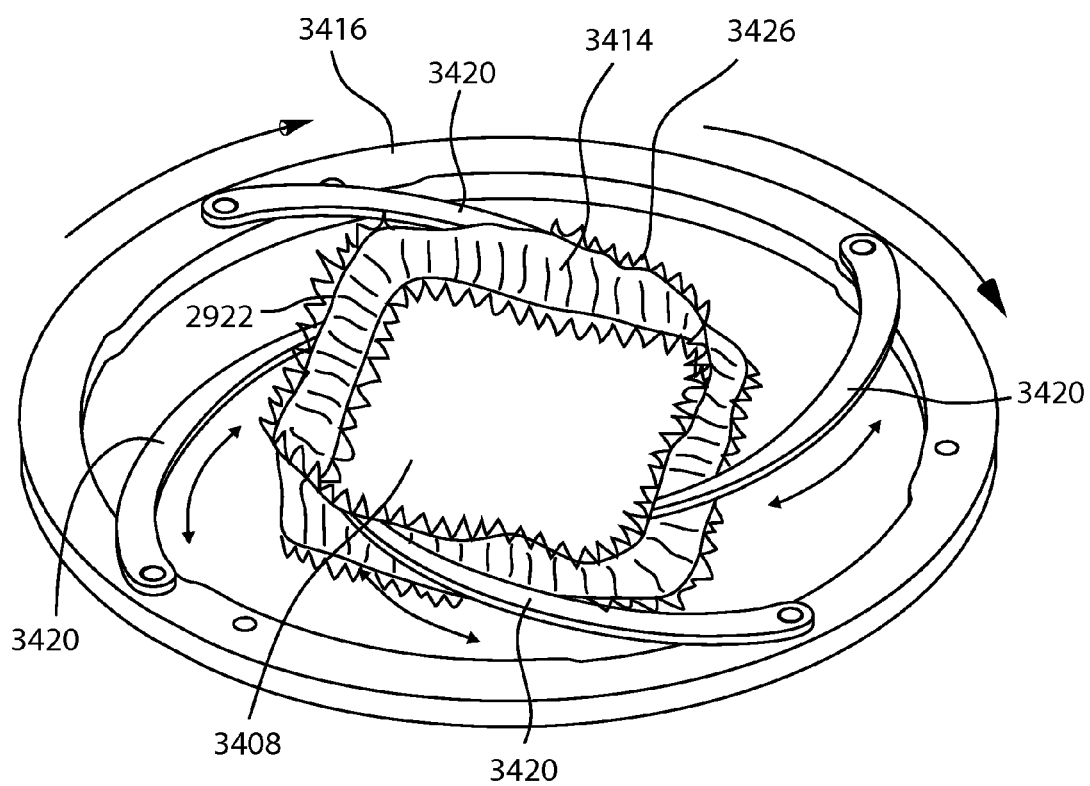
FIG. 58 is a perspective view of a carriage and an expandable capture member.

FIG. 58 shows a tissue fixation carriage 3416 with a tissue fixation member 3414 attached to the carriage by a plurality of attachment features 3420. Tissue fixation member 3414 is expandable and may include an expandable mesh which encircles a central opening 3408. Small teeth or barbs 3426 are formed on the edges of the fixation member 3414. When carriage 3416 is rotated in a first direction, fixation member 3414 expands and tissue may be positioned in the central opening 3408. When the carriage 3416 is rotated in a second direction, fixation member 3414 contracts and the tissue is captured in the opening 3408. The barbs 3426 help prevent withdrawal of the tissue.

Figure 59A:
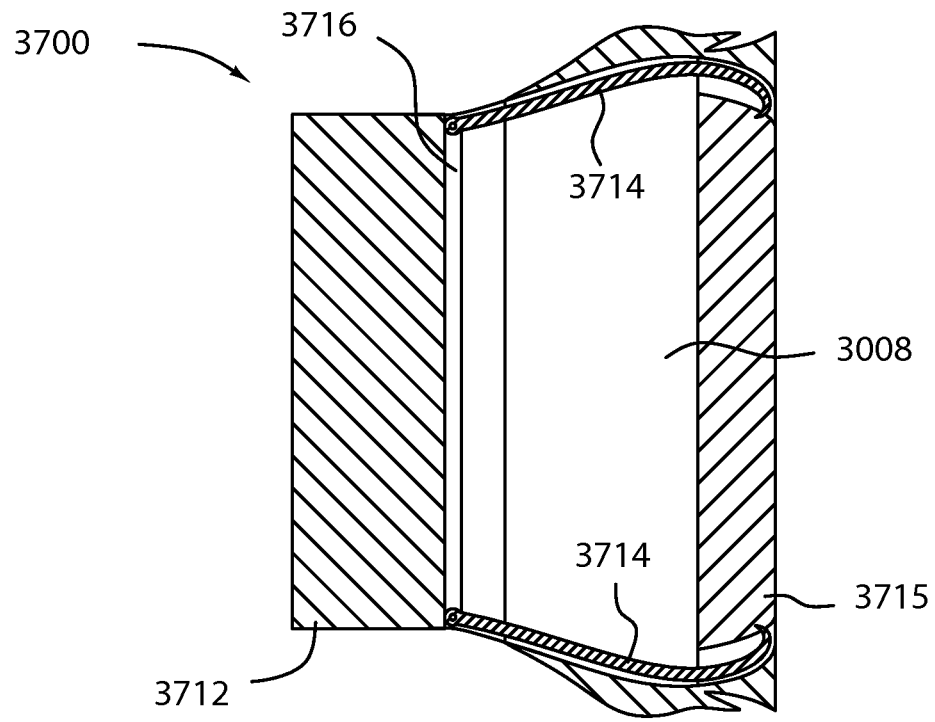
FIG. 59A is a side cross-sectional view of a tissue fixation device with two needles.
Figure 59B:
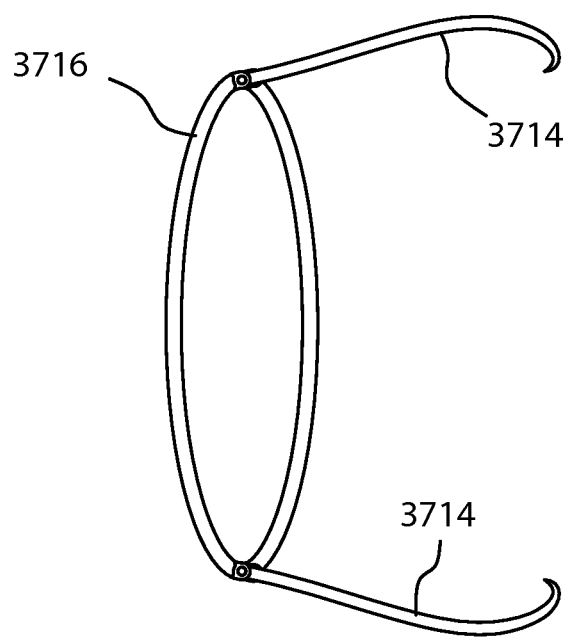
FIG. 59B is a perspective view of the needles and a carriage of FIG. 59A.

FIGS. 59A and 59B are views of a tissue fixation device 3700 including housing 3712, cap 3715, and two needles 3714 captured in needle carriage 3716. Instead of deploying circumferentially inward, when deployed the needles drop down into the center opening 3008 of the device, capturing tissue positioned therein.

Figure 60:
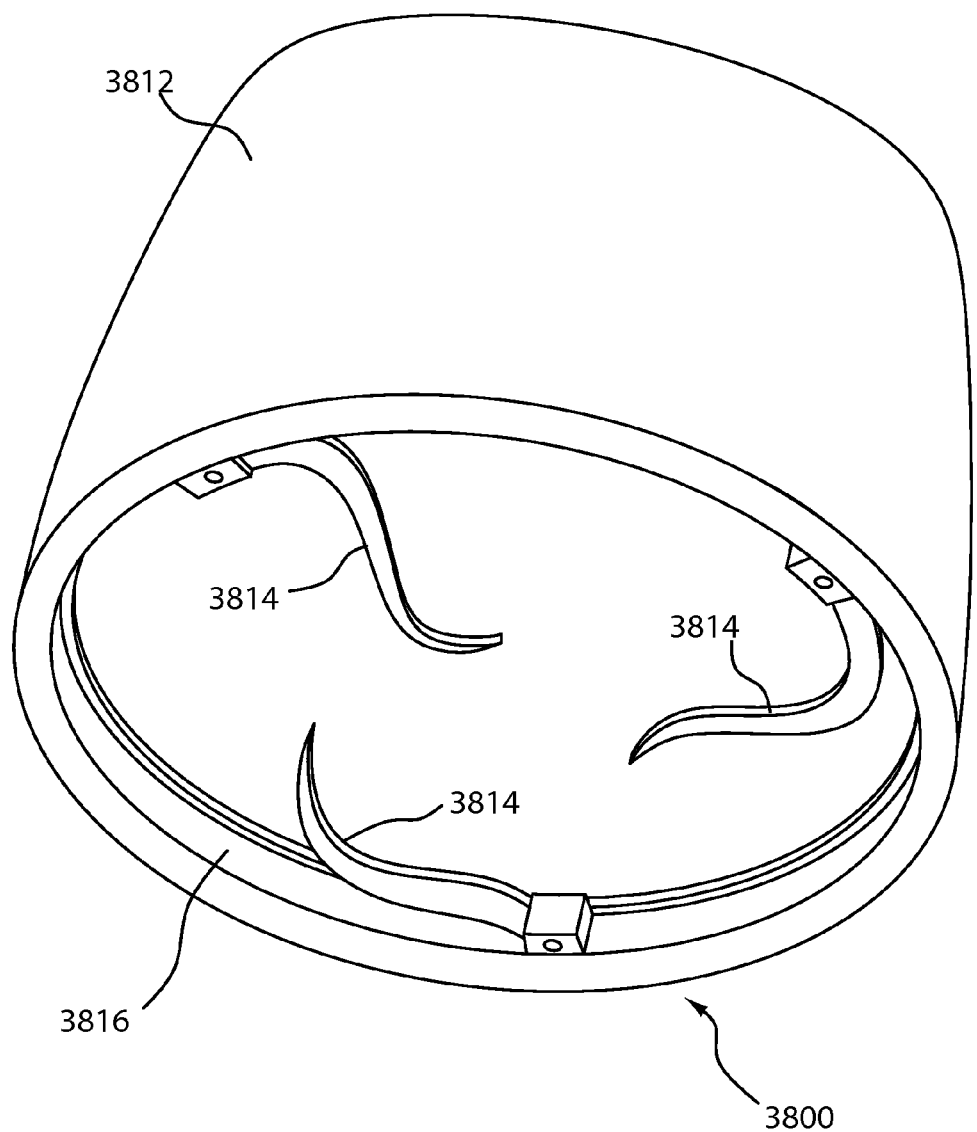
FIG. 60 is a perspective view of a tissue fixation device having needles with compound curvature.

FIG. 60 shows a tissue fixation device 3800 including housing 3812, and several needles 3814 captured in needle carriage 3816. Each needle 3814 is compoundly curved, having at least one convex portion and one concave portion. When deployed, needles 3814 trap tissue between the needle 3814 and the carriage 3816.

It should be understood that the present apparatuses and methods are not intended to be limited to the particular forms disclosed. Rather, they are intended to include all modifications, equivalents, and alternatives falling within the scope of the claims. They are further intended to include embodiments which may be formed by combining features from the disclosed embodiments, and variants thereof.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

The present invention may be embodied in other specific forms without departing from its spirit or essential characteristics. It is appreciated that various features of the above-described examples can be mixed and matched to form a variety of other alternatives. For example, fixation members, needles, hooks or barbs may be interchangeable in any of the embodiments set forth herein, as may the actuation means for deployment. As such, the described embodiments are to be considered in all respects only as illustrative and not restrictive. Similarly, manufacturing, assembly methods, and materials described for one device may be used in the manufacture or assembly of another device. The scope of the invention is, therefore, indicated by the appended claims rather than by the foregoing description. All changes which come within the meaning and range of equivalency of the claims are to be embraced within their scope.

The invention claimed is:

1. A tissue fixation device, comprising:
a housing having an inner space configured to receive tissue therein and an enclosed section, wherein the enclosed section completely encloses at least one planar surface and surrounds the inner space;
a cap detachable from the housing;
at least one fixation member movable between a retracted configuration in which the at least one fixation member is retracted relative to the inner space and a deployed configuration in which the at least one fixation member protrudes into the inner space; and
a fixation member carriage captured between the cap and the housing, the fixation member carriage engaged with the at least one fixation member and configured to move the at least one fixation member between the deployed configuration and the retracted configuration;
wherein the housing and the fixation member carriage are substantially circular, and wherein rotational movement of the fixation member carriage along a circle defined by the housing moves the at least one fixation member between the retracted and deployed configurations; and
wherein the at least one fixation member is deflected by the cap as it moves to the deployed configuration.

2. The tissue fixation device of claim 1, further comprising a plurality of tabs and a plurality of slots, wherein the tabs are received in the slots to attach the cap to the housing.

3. The tissue fixation device of any of claim 1, further comprising a first line and a second line, the first and second lines connected to the fixation member carriage, wherein pulling the first line moves the fixation member carriage in a first direction to deploy the at least one fixation member, and wherein pulling the second line moves the fixation member carriage in a second direction to retract the at least one fixation member.

4. The tissue fixation device of claim 3, wherein the at least one fixation member is deployed inwardly toward a lengthwise central axis of the housing in a plane substantially perpendicular to the lengthwise central axis.

5. The tissue fixation device of claim 1, wherein the at least one fixation member is curved with an arch shape that substantially lies in a single plane.

6. The tissue fixation device of claim 5, further comprising three fixation members, each of the three fixation members being substantially coplanar with each other.

7. The tissue fixation device of claim 1, wherein the at least one fixation member is connected to the fixation member carriage by a hinge type connection, about which the fixation member pivots.

8. The tissue fixation device of claim 1, wherein the housing is frustoconical in shape.

9. A tissue fixation device, comprising:
a housing having an inner space configured to receive tissue therein and an enclosed section, wherein the enclosed section completely encloses at least one planar surface and surrounds the inner space;
at least one fixation member movable between a retracted configuration in which the at least one fixation member is retracted relative to the inner space and a deployed configuration in which the at least one fixation member protrudes into the inner space;
a fixation member carriage, the fixation member carriage engaged with the at least one fixation member and configured to move the at least one fixation member between the deployed configuration and the retracted configuration; and a first line and a second line, the first and second lines connected to the fixation member carriage, wherein pulling the first line moves the fixation member carriage in a first direction to deploy the at least one fixation member, and wherein pulling the second line moves the fixation member carriage in a second direction to retract the at least one fixation member.

10. The tissue fixation device of claim 9, wherein the at least one fixation member is deployed inwardly toward a lengthwise central axis of the housing in a plane substantially perpendicular to the lengthwise central axis.

11. The tissue fixation device of claim 10, wherein the at least one fixation member is connected to the fixation member carriage by a hinge type connection, about which the fixation member pivots.

12. The tissue fixation device of claim 9, wherein the at least one fixation member is curved with an arch shape that substantially lies in a single plane.

13. The tissue fixation device of claim 12, wherein the at least one fixation member has a sharp point capable of piercing tissue.

14. The tissue fixation device of claim 12, further comprising three fixation members, each of the three fixation members being substantially coplanar with each other.

15. A tissue fixation device, comprising:
a housing having an inner space configured to receive tissue therein and an enclosed section, wherein the enclosed section completely encloses at least one planar surface and surrounds the inner space;
a cap detachable from the housing;
at least one fixation member movable between a retracted configuration in which the at least one fixation member is retracted relative to the inner space and a deployed configuration in which the at least one fixation member protrudes into the inner space; and
a fixation member carriage captured between the cap and the housing, the fixation member carriage engaged with the at least one fixation member and configured to move the at least one fixation member between the deployed configuration and the retracted configuration;
wherein the at least one fixation member is deflected by the cap as it moves to the deployed configuration.

16. The tissue fixation device of claim 15, wherein the housing and the fixation member carriage are substantially circular, and wherein rotational movement of the fixation member carriage along a circle defined by the housing moves the at least one fixation member between the retracted and deployed configurations.

17. The tissue fixation device of claim 16, wherein the at least one fixation member is curved, and wherein the diameter of the curvature of the at least one fixation member is less than the diameter of the circle.

18. The tissue fixation device of claim 15, wherein the at least one fixation member is deflected inwardly by the cap toward a lengthwise central axis of the housing in a plane substantially perpendicular to the lengthwise central axis.

19. The tissue fixation device of claim 18, wherein the at least one fixation member is curved with an arch shape that substantially lies in the plane.

20. The tissue fixation device of claim 19, further comprising three fixation members, each of the three fixation members being substantially coplanar with each other.

* * * * *